United States Patent
Buerki et al.

(10) Patent No.: US 12,378,610 B2
(45) Date of Patent: Aug. 5, 2025

(54) SYSTEMS AND METHODS FOR PREPROCESSING TARGET DATA AND GENERATING PREDICTIONS USING A MACHINE LEARNING MODEL

(71) Applicants: Veracyte SD, Inc., South San Francisco, CA (US); Mayo Foundation for Medical Education and Research, Rochester, MN (US)

(72) Inventors: Christine Buerki, Vancouver (CA); Anamaria Crisan, Vancouver (CA); Elai Davicioni, La Jolla, CA (US); Nicholas George Erho, Vancouver (CA); Mercedeh Ghadessi, New Westminster (CA); Robert B. Jenkins, Rochester, MN (US); Ismael A. Vergara Correa, West Vancouver (CA)

(73) Assignees: Veracyte SD, Inc., South San Francisco, CA (US); Mayo Foundation for Medical Education and Research, Rochester, MN (US)

( * ) Notice: Subject to any disclaimer, the term of this patent is extended or adjusted under 35 U.S.C. 154(b) by 32 days.

(21) Appl. No.: 18/506,690

(22) Filed: Nov. 10, 2023

(65) Prior Publication Data
US 2025/0156731 A1    May 15, 2025

Related U.S. Application Data

(62) Division of application No. 17/346,106, filed on Jun. 11, 2021, now abandoned, which is a division of
(Continued)

(51) Int. Cl.
*G06N 5/01*    (2023.01)

(52) U.S. Cl.
CPC .................................... *G06N 5/01* (2023.01)

(58) Field of Classification Search
CPC ........ G06N 20/00; G06N 3/045; G06N 20/20; G06N 5/01; G06N 20/10; G06N 5/04;
(Continued)

(56) References Cited

U.S. PATENT DOCUMENTS 3,645,691 A    2/1972   Guenter et al.
3,687,808 A    8/1972   Thomas, Jr. et al.
(Continued)

FOREIGN PATENT DOCUMENTS

EP    0 684 315    11/1995
EP    1 409 727    11/2005
(Continued)

OTHER PUBLICATIONS

US 5,962,233 A, 10/1999, Livak et al. (withdrawn)
(Continued)

*Primary Examiner* — Luis A Sitiriche
(74) *Attorney, Agent, or Firm* — Foley & Lardner LLP

(57) ABSTRACT

In some embodiments, a machine learning model may be accessed and used to generate a likelihood score related to a condition. In some embodiments, pre-computed vectors may be derived from a training dataset used to build the machine learning model, and the pre-computed vectors may be used to generate processed data from target data derived from a target sample. The machine learning model may then be used on the processed data to generate the likelihood score related to the condition. As an example, subsets of the training dataset may be randomly selected, and the pre-computed vectors may be derived from the randomly-selected subsets of the training dataset. The pre-computed vectors may be applied to the target data to generate the processed data. In one use case, for example, the target data may be normalized using the pre-computed vectors.

19 Claims, 7 Drawing Sheets

Related U.S. Application Data application No. 13/968,838, filed on Aug. 16, 2013, now Pat. No. 11,035,005.

(60) Provisional application No. 61/783,124, filed on Mar. 14, 2013, provisional application No. 61/764,365, filed on Feb. 13, 2013, provisional application No. 61/684,066, filed on Aug. 16, 2012.

(58) Field of Classification Search
CPC .......... G06N 7/01; G06N 3/044; G06N 3/047; G06N 3/08; G06N 3/086; G06N 5/02; G06N 3/088; G06N 3/126; G06N 10/60; G06N 3/0464; G06N 5/022; G06N 5/045; G06N 3/02; G06N 3/04; G06N 3/0499; G06N 3/082; G06N 3/084; G06N 3/09; G06N 3/0409; G06N 5/025; G06N 5/027; G06N 5/046; G06N 5/048; G16B 20/00; G16B 40/20; G16B 25/10; G16B 40/10; G16B 40/30; A61B 2503/04; A61B 2503/06; A61B 5/0205; A61B 5/021; A61B 5/02116; A61B 5/14546; A61B 5/318; A61B 5/346; A61B 5/7264; A61B 5/7275

See application file for complete search history.

(56) References Cited

U.S. PATENT DOCUMENTS

| | | |
|---|---|---|
| 4,323,546 A | 4/1982 | Crockfor et al. |
| 4,683,195 A | 7/1987 | Mullis et al. |
| 4,683,202 A | 7/1987 | Mullis et al. |
| 4,800,159 A | 1/1989 | Mullis et al. |
| 4,965,188 A | 10/1990 | Mullis et al. |
| 5,130,238 A | 7/1992 | Malek et al. |
| 5,143,854 A | 9/1992 | Pinung et al. |
| 5,225,326 A | 7/1993 | Bresser et al. |
| 5,270,184 A | 12/1993 | Walker et al. |
| 5,283,174 A | 2/1994 | Arnold et al. |
| 5,288,514 A | 2/1994 | Ellman |
| 5,384,261 A | 1/1995 | Winkle et al. |
| 5,399,491 A | 3/1995 | Kacian et al. |
| 5,455,166 A | 10/1995 | Walker |
| 5,480,784 A | 1/1996 | Kacian et al. |
| 5,494,810 A | 2/1996 | Barany et al. |
| 5,538,848 A | 7/1996 | Livak et al. |
| 5,545,524 A | 8/1996 | Trent et al. |
| 5,604,839 A * | 2/1997 | Acero ............... G10L 15/02 704/224 |
| 5,677,195 A | 10/1997 | Winkler et al. |
| 5,705,365 A | 1/1998 | Ryder et al. |
| 5,710,029 A | 1/1998 | Ryder et al. |
| 5,711,029 A | 1/1998 | Ryder et al. |
| 5,744,305 A | 4/1998 | Fodor et al. |
| 5,814,447 A | 9/1998 | Ishiguro et al. |
| 5,824,518 A | 10/1998 | Kacian et al. |
| 5,830,711 A | 11/1998 | Barany et al. |
| 5,846,717 A | 12/1998 | Brow et al. |
| 5,854,033 A | 12/1998 | Lizardi |
| 5,854,206 A | 12/1998 | Twardzik et al. |
| 5,888,779 A | 3/1999 | Kacian et al. |
| 5,925,517 A | 7/1999 | Tyagi et al. |
| 5,928,862 A | 7/1999 | Morrison |
| 5,965,360 A | 10/1999 | Zain et al. |
| 5,985,557 A | 11/1999 | Prudent et al. |
| 5,989,815 A | 11/1999 | Skolnick et al. |
| 5,994,069 A | 11/1999 | Hall et al. |
| 6,001,567 A | 12/1999 | Brow et al. |
| 6,022,692 A | 2/2000 | Coulie et al. |
| 6,027,887 A | 2/2000 | Zavada et al. |
| 6,034,218 A | 3/2000 | Reed et al. |
| 6,090,543 A | 7/2000 | Prudent et al. |
| 6,121,489 A | 9/2000 | Dorner et al. |
| 6,136,182 A | 10/2000 | Dolan et al. |
| 6,150,097 A | 11/2000 | Tyagi et al. |
| 6,198,107 B1 | 3/2001 | Seville |
| 6,218,523 B1 | 4/2001 | French |
| 6,225,051 B1 | 5/2001 | Sugiyama et al. |
| 6,251,639 B1 | 6/2001 | Kurn |
| 6,262,245 B1 | 7/2001 | Xu et al. |
| 6,268,142 B1 | 7/2001 | Duff et al. |
| 6,303,305 B1 | 10/2001 | Wittwer et al. |
| 6,410,278 B1 | 6/2002 | Notomi et al. |
| 6,436,642 B1 | 8/2002 | Gould-Rothberg et al. |
| 6,541,205 B1 | 4/2003 | Yokoyama et al. |
| 6,573,043 B1 | 6/2003 | Cohen et al. |
| 6,630,358 B1 | 10/2003 | Wagner et al. |
| 6,723,506 B2 | 4/2004 | Fletcher et al. |
| 6,828,429 B1 | 12/2004 | Srivastava et al. |
| 7,008,765 B1 | 3/2006 | Bussemakers et al. |
| 7,186,514 B2 | 3/2007 | Zavada et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,280,922 B2 | 10/2007 | Mei et al. |
| 7,300,788 B2 | 11/2007 | Matsuzaki et al. |
| 7,319,011 B2 | 1/2008 | Riggins et al. |
| 7,323,305 B2 | 1/2008 | Leamon et al. |
| 7,335,762 B2 | 2/2008 | Rothberg et al. |
| 7,358,061 B2 | 4/2008 | Yamamoto et al. |
| 7,361,488 B2 | 4/2008 | Fan et al. |
| 7,378,233 B2 | 5/2008 | Sidransky et al. |
| 7,407,755 B2 | 8/2008 | Lubinski et al. |
| 7,541,169 B2 | 6/2009 | Freimuth et al. |
| 7,598,052 B2 | 10/2009 | Giordanos et al. |
| 7,662,553 B2 | 2/2010 | Lenz et al. |
| 7,767,391 B2 | 8/2010 | Scott et al. |
| 7,901,881 B2 | 3/2011 | Libutti et al. |
| 7,901,888 B2 | 3/2011 | Kebebew |
| 7,914,988 B1 | 3/2011 | Chudin et al. |
| 7,927,826 B2 | 4/2011 | Riggins et al. |
| 8,008,009 B2 | 8/2011 | Choquet-Kastylevsky et al. |
| 8,202,692 B2 | 6/2012 | Giordano et al. |
| 8,273,539 B2 | 9/2012 | Klee et al. |
| 8,293,880 B2 | 10/2012 | Cote et al. |
| 8,299,233 B2 | 10/2012 | Andre et al. |
| 8,338,109 B2 | 12/2012 | Vasmatzis et al. |
| 8,354,228 B2 | 1/2013 | Ron |
| 8,465,914 B2 | 6/2013 | Brown et al. |
| 8,541,170 B2 | 9/2013 | Kennedy et al. |
| 8,568,971 B2 | 10/2013 | Brown et al. |
| 8,669,057 B2 | 3/2014 | Kennedy et al. |
| 8,802,599 B2 | 8/2014 | Aharonov et al. |
| 8,828,656 B2 | 9/2014 | Bullerdiek et al. |
| 8,877,445 B2 | 11/2014 | Shackney |
| 8,945,829 B2 | 2/2015 | Keutgen et al. |
| 9,040,286 B2 | 5/2015 | Zon et al. |
| 9,074,258 B2 | 7/2015 | Davicion et al. |
| 9,096,906 B2 | 8/2015 | Aharonov et al. |
| 9,157,123 B2 | 10/2015 | Xing |
| 9,175,352 B2 | 11/2015 | Keutgen et al. |
| 9,206,481 B2 | 12/2015 | Srivastava et al. |
| 9,206,482 B2 | 12/2015 | Davicioni et al. |
| 9,234,244 B2 | 1/2016 | Zeiger et al. |
| 9,435,812 B2 | 9/2016 | Pestano et al. |
| 9,495,515 B1 | 11/2016 | Giulia et al. |
| 9,534,249 B2 | 1/2017 | Vasmatzis et al. |
| 9,587,279 B2 | 3/2017 | Fahey, III et al. |
| 9,617,604 B2 | 4/2017 | Davicion et al. |
| 9,631,239 B2 | 4/2017 | Perou |
| 9,708,667 B2 | 7/2017 | Yanai et al. |
| 9,714,452 B2 | 7/2017 | Davicioni et al. |
| 9,856,537 B2 | 1/2018 | Kennedy et al. |
| 9,994,907 B2 | 6/2018 | Davicioni et al. |
| 10,114,924 B2 | 10/2018 | Kennedy et al. |
| 10,407,731 B2 | 9/2019 | Klee et al. |
| 10,407,735 B2 | 9/2019 | Chinnaiyan et al. |
| 10,422,009 B2 | 9/2019 | Davicioni et al. |
| 10,494,677 B2 | 12/2019 | Vasmatzis et al. |
| 10,513,737 B2 | 12/2019 | Davicioni et al. |
| 10,865,452 B2 | 12/2020 | Davicioni |
| 11,035,005 B2 | 6/2021 | Buerki et al. |

(56) References Cited

U.S. PATENT DOCUMENTS

| | | |
|---|---|---|
| 11,078,542 B2 | 8/2021 | Davicioni et al. |
| 11,208,697 B2 | 12/2021 | Davicioni et al. |
| 2001/0051344 A1 | 12/2001 | Shalon et al. |
| 2002/0076735 A1 | 6/2002 | Williams et al. |
| 2002/0090633 A1 | 7/2002 | Becker et al. |
| 2002/0119463 A1 | 8/2002 | Fads |
| 2002/0168638 A1 | 11/2002 | Schlegel et al. |
| 2002/0169137 A1 | 11/2002 | Reiner et al. |
| 2002/0182586 A1 | 12/2002 | Morris et al. |
| 2003/0119168 A1 | 6/2003 | Madison et al. |
| 2003/0152980 A1 | 8/2003 | Golub et al. |
| 2003/0175736 A1 | 9/2003 | Chinnaiyan et al. |
| 2003/0185830 A1 | 10/2003 | Xu et al. |
| 2003/0186248 A1 | 10/2003 | Erlander et al. |
| 2003/0190602 A1 | 10/2003 | Pressman et al. |
| 2003/0194734 A1 | 10/2003 | Jatkoe |
| 2003/0224399 A1 | 12/2003 | Reed et al. |
| 2003/0235820 A1 | 12/2003 | Mack et al. |
| 2004/0009481 A1 | 1/2004 | Schlegel et al. |
| 2004/0018493 A1 | 1/2004 | Anastasio et al. |
| 2004/0019466 A1 | 1/2004 | Minor et al. |
| 2004/0029114 A1 | 2/2004 | Mack et al. |
| 2004/0058378 A1 | 3/2004 | Kong et al. |
| 2004/0259086 A1 | 12/2004 | Schlegel et al. |
| 2005/0042222 A1 | 2/2005 | Yamamoto et al. |
| 2005/0042638 A1 | 2/2005 | Arnold et al. |
| 2005/0048533 A1 | 3/2005 | Sidransky et al. |
| 2005/0048547 A1* | 3/2005 | Zhao ............... G16B 40/10 702/20 |
| 2005/0064455 A1 | 3/2005 | Baker et al. |
| 2005/0118625 A1 | 6/2005 | Mounts |
| 2005/0137805 A1 | 6/2005 | Lewin et al. |
| 2005/0202442 A1 | 9/2005 | Morris et al. |
| 2005/0227917 A1 | 10/2005 | Williams et al. |
| 2005/0240357 A1 | 10/2005 | Minor |
| 2005/0250125 A1 | 11/2005 | Novakoff |
| 2005/0260646 A1 | 11/2005 | Baker et al. |
| 2005/0266443 A1 | 12/2005 | Croce et al. |
| 2005/0266459 A1 | 12/2005 | Poulsen |
| 2006/0019256 A1 | 1/2006 | Clarke et al. |
| 2006/0019615 A1 | 1/2006 | Ditmer |
| 2006/0035244 A1 | 2/2006 | Riggins et al. |
| 2006/0046253 A1 | 3/2006 | Nakao |
| 2006/0046265 A1 | 3/2006 | Becker et al. |
| 2006/0083744 A1 | 4/2006 | Chen et al. |
| 2006/0088851 A1 | 4/2006 | Erlander et al. |
| 2006/0094061 A1 | 5/2006 | Brys et al. |
| 2006/0105360 A1 | 5/2006 | Croce et al. |
| 2006/0127907 A1 | 6/2006 | Matsubara et al. |
| 2006/0134663 A1 | 6/2006 | Harkin et al. |
| 2006/0204989 A1 | 9/2006 | Kopreski |
| 2006/0211017 A1 | 9/2006 | Chinnaiyan et al. |
| 2007/0010469 A1 | 1/2007 | Chan |
| 2007/0020657 A1 | 1/2007 | Grebe et al. |
| 2007/0031873 A1 | 2/2007 | Wang et al. |
| 2007/0037165 A1 | 2/2007 | Venter et al. |
| 2007/0037186 A1 | 2/2007 | Jiang et al. |
| 2007/0048738 A1 | 3/2007 | Donkena et al. |
| 2007/0065827 A1 | 3/2007 | Pauloski et al. |
| 2007/0065833 A1 | 3/2007 | Gupta |
| 2007/0083334 A1 | 4/2007 | Mintz et al. |
| 2007/0099197 A1 | 5/2007 | Afar et al. |
| 2007/0099209 A1 | 5/2007 | Clarke et al. |
| 2007/0105133 A1 | 5/2007 | Clarke et al. |
| 2007/0148667 A1 | 6/2007 | Williams et al. |
| 2007/0148687 A1 | 6/2007 | Bedingham et al. |
| 2007/0161004 A1 | 7/2007 | Brown et al. |
| 2007/0172841 A1 | 7/2007 | Wang |
| 2007/0172844 A1 | 7/2007 | Lancaster et al. |
| 2007/0212702 A1 | 9/2007 | Tomlins et al. |
| 2007/0220621 A1 | 9/2007 | Clarke et al. |
| 2007/0238119 A1 | 10/2007 | Yu et al. |
| 2007/0259352 A1 | 11/2007 | Bentwich et al. |
| 2007/0275915 A1 | 11/2007 | Hallenbeck et al. |
| 2008/0009001 A1 | 1/2008 | Bettuzzi et al. |
| 2008/0028302 A1 | 1/2008 | Meschkat |
| 2008/0044824 A1 | 2/2008 | Giordano et al. |
| 2008/0076674 A1 | 3/2008 | Litman et al. |
| 2008/0124344 A1 | 5/2008 | Combs et al. |
| 2008/0131892 A1 | 6/2008 | Becker et al. |
| 2008/0145841 A1 | 6/2008 | Libutti et al. |
| 2008/0254470 A1 | 10/2008 | Berlkin |
| 2008/0269157 A1 | 10/2008 | Srivastava et al. |
| 2008/0274457 A1 | 11/2008 | Eng et al. |
| 2008/0281568 A1 | 11/2008 | Kao et al. |
| 2009/0020433 A1 | 1/2009 | Cohen et al. |
| 2009/0036415 A1 | 2/2009 | Rubin et al. |
| 2009/0062144 A1 | 3/2009 | Guo |
| 2009/0075921 A1 | 3/2009 | Ikegawa |
| 2009/0149333 A1 | 6/2009 | Knudsen et al. |
| 2009/0191535 A1 | 7/2009 | Connelly et al. |
| 2009/0204333 A1 | 8/2009 | Friend et al. |
| 2009/0239221 A1 | 9/2009 | Chinnaiyan et al. |
| 2009/0280490 A1 | 11/2009 | Baker et al. |
| 2009/0298082 A1 | 12/2009 | Klee et al. |
| 2010/0055704 A1 | 3/2010 | Giordano et al. |
| 2010/0075384 A1 | 3/2010 | Kong et al. |
| 2010/0099093 A1 | 4/2010 | Weaver et al. |
| 2010/0131286 A1 | 5/2010 | Houlgatte et al. |
| 2010/0131432 A1 | 5/2010 | Kennedy et al. |
| 2010/0137164 A1 | 6/2010 | Rubin et al. |
| 2010/0178653 A1 | 7/2010 | Aharonov et al. |
| 2010/0184093 A1* | 7/2010 | Donovan ............... G16B 25/00 435/287.1 |
| 2010/0021538 A1 | 8/2010 | Iljin et al. |
| 2010/0215638 A1 | 8/2010 | Ijin et al. |
| 2010/0257617 A1 | 10/2010 | Ami et al. |
| 2010/0279327 A1 | 11/2010 | Ossovskaya |
| 2010/0285979 A1 | 11/2010 | Zeiger et al. |
| 2011/0009286 A1 | 1/2011 | Andre et al. |
| 2011/0045462 A1 | 2/2011 | Fu et al. |
| 2011/0092375 A1 | 4/2011 | Zamore et al. |
| 2011/0136683 A1 | 6/2011 | Davicioni |
| 2011/0152110 A1 | 6/2011 | Vierlinger et al. |
| 2011/0166838 A1 | 7/2011 | Gehrmann |
| 2011/0178163 A1 | 7/2011 | Chowdhury |
| 2011/0212855 A1 | 9/2011 | Rafnar et al. |
| 2011/0229894 A1 | 9/2011 | Levy et al. |
| 2011/0230372 A1 | 9/2011 | Willman et al. |
| 2011/0236903 A1 | 9/2011 | McClelland |
| 2011/0287946 A1 | 11/2011 | Gudmundsson et al. |
| 2011/0294123 A1 | 12/2011 | Nakamura et al. |
| 2011/0312520 A1 | 12/2011 | Kennedy et al. |
| 2012/0015839 A1 | 1/2012 | Chinnaiyan |
| 2012/0015843 A1 | 1/2012 | Von et al. |
| 2012/0041274 A1 | 2/2012 | Stone et al. |
| 2012/0108453 A1 | 5/2012 | Smit et al. |
| 2012/0115743 A1 | 5/2012 | Davicioni et al. |
| 2012/0122698 A1 | 5/2012 | Stacey et al. |
| 2012/0122718 A1 | 5/2012 | Reisman |
| 2012/0157334 A1 | 6/2012 | Beaudenon-Huibregtse et al. |
| 2012/0172243 A1 | 7/2012 | Davicioni et al. |
| 2012/0214165 A1 | 8/2012 | Walfish et al. |
| 2012/0220474 A1 | 8/2012 | Kennedy et al. |
| 2012/0304318 A1 | 11/2012 | Ohnuma et al. |
| 2013/0004974 A1 | 1/2013 | Klee et al. |
| 2013/0023434 A1 | 1/2013 | Van |
| 2013/0142728 A1 | 6/2013 | Beaudenon-Huibregtse et al. |
| 2013/0143206 A1* | 6/2013 | McCaffrey ........... C12Q 1/6869 435/6.1 |
| 2013/0150257 A1 | 6/2013 | Abdueva et al. |
| 2013/0172203 A1 | 7/2013 | Yeatman et al. |
| 2013/0184999 A1 | 7/2013 | Ding |
| 2013/0196866 A1 | 8/2013 | Pestano et al. |
| 2013/0225662 A1 | 8/2013 | Kennedy et al. |
| 2013/0231258 A1 | 9/2013 | Wilde et al. |
| 2013/0273543 A1 | 10/2013 | Gudmundsson et al. |
| 2013/0302808 A1 | 11/2013 | Vasmatzis |
| 2013/0302810 A1 | 11/2013 | Latham et al. |
| 2013/0303826 A1 | 11/2013 | Jurisica et al. |
| 2014/0030714 A1 | 1/2014 | Paschke et al. |
| 2014/0080731 A1 | 3/2014 | Davicioni et al. |
| 2014/0087961 A1 | 3/2014 | Sulem et al. |
| 2014/0099261 A1 | 4/2014 | Keutgen et al. |

(56) References Cited

U.S. PATENT DOCUMENTS

| | | | |
|---|---|---|---|
| 2014/0121126 A1 | 5/2014 | Bivona et al. |
| 2014/0143188 A1 | 5/2014 | Mackey et al. |
| 2014/0228237 A1 | 8/2014 | Kennedy et al. |
| 2014/0243240 A1 | 8/2014 | Soldin et al. |
| 2014/0302042 A1 | 10/2014 | Chin et al. |
| 2014/0303002 A1 | 10/2014 | Shak et al. |
| 2014/0303034 A1 | 10/2014 | Gascoyne et al. |
| 2014/0315199 A1 | 10/2014 | Rhodes et al. |
| 2014/0315739 A1 | 10/2014 | Aharonov et al. |
| 2014/0349856 A1 | 11/2014 | Schnabel et al. |
| 2014/0349864 A1 | 11/2014 | Kennedy et al. |
| 2014/0371096 A1 | 12/2014 | Umbright et al. |
| 2015/0038376 A1 | 2/2015 | Tian et al. |
| 2015/0099665 A1 | 4/2015 | Rosenfeld et al. |
| 2015/0141470 A1 | 5/2015 | Garraway et al. |
| 2015/0253331 A1 | 9/2015 | Zijlstra |
| 2015/0275306 A1 | 10/2015 | Bernards et al. |
| 2015/0292030 A1 | 10/2015 | McConkey |
| 2015/0299808 A1 | 10/2015 | Gonzalez et al. |
| 2015/0307947 A1 | 10/2015 | Basu et al. |
| 2015/0329915 A1 | 11/2015 | Davicioni et al. |
| 2015/0368724 A1 | 12/2015 | Aharonov et al. |
| 2016/0024586 A1 | 1/2016 | Delfour et al. |
| 2016/0032395 A1 | 2/2016 | Davicioni et al. |
| 2016/0032400 A1 | 2/2016 | Gomis et al. |
| 2016/0068915 A1 | 3/2016 | Kennedy et al. |
| 2016/0076108 A1 | 3/2016 | Davicioni et al. |
| 2016/0115546 A1 | 4/2016 | Rosenfeld et al. |
| 2016/0120832 A1 | 5/2016 | Rabinowitz et al. |
| 2016/0251729 A1 | 9/2016 | Chinnaiyan |
| 2016/0312294 A1 | 10/2016 | Walker |
| 2016/0312305 A1 | 10/2016 | Kennedy et al. |
| 2016/0312306 A1 | 10/2016 | Kennedy et al. |
| 2016/0312307 A1 | 10/2016 | Kennedy et al. |
| 2016/0312308 A1 | 10/2016 | Kennedy et al. |
| 2017/0016076 A1 | 1/2017 | Barnett-Itzhaki et al. |
| 2017/0145513 A1 | 5/2017 | Kennedy et al. |
| 2017/0166980 A1 | 6/2017 | Fahey, III et al. |
| 2017/0218455 A1 | 8/2017 | Steelman |
| 2017/0329894 A1 | 11/2017 | Kennedy et al. |
| 2018/0016642 A1 | 1/2018 | Kennedy et al. |
| 2018/0030540 A1 | 2/2018 | Davicioni et al. |
| 2018/0068058 A1 | 3/2018 | Abdueva et al. |
| 2018/0112275 A1 | 4/2018 | Davicioni et al. |
| 2018/0122508 A1 | 5/2018 | Wilde et al. |
| 2018/0127832 A1 | 5/2018 | Kennedy et al. |
| 2018/0282817 A1 | 10/2018 | You |
| 2018/0291459 A1 | 10/2018 | Al-Deen Ashab et al. |
| 2019/0204322 A1 | 7/2019 | Alshalalfa et al. |
| 2019/0218621 A1 | 7/2019 | Davicioni |
| 2020/0165682 A1 | 5/2020 | Chinnaiyan et al. |
| 2020/0181710 A1 | 6/2020 | Steelman |
| 2020/0191773 A1 | 6/2020 | Kitano et al. |
| 2020/0224276 A1 | 7/2020 | Chinnaiyan et al. |
| 2021/0130902 A1 | 5/2021 | Da Vicioni |
| 2021/0317531 A1 | 10/2021 | Da Vicioni |
| 2022/0177974 A1 | 6/2022 | Davicioni |
| 2022/0213557 A1 | 7/2022 | De Jong |
| 2023/0115828 A1 | 4/2023 | De Jong |
| 2023/0151429 A1 | 5/2023 | Davicioni |
| 2023/0220485 A1 | 7/2023 | Davicioni |
| 2024/0002944 A1 | 1/2024 | Schaeffer |

FOREIGN PATENT DOCUMENTS

| | | | |
|---|---|---|---|
| EP | 1 777 523 | 4/2007 | |
| EP | 2 366 800 | 9/2011 | |
| WO | WO 90/015070 | 12/1990 | |
| WO | WO 92/010092 | 6/1992 | |
| WO | WO 93/009668 | 5/1993 | |
| WO | WO 93/022684 | 11/1993 | |
| WO | WO 98/045420 | 10/1998 | |
| WO | WO 01/060860 | 8/2001 | |
| WO | WO 01/066753 | 9/2001 | |
| WO | WO 02/000929 | 1/2002 | |
| WO | WO 02/083921 | 10/2002 | |
| WO | WO 03/012067 | 2/2003 | |
| WO | WO 04/037972 | 5/2004 | |
| WO | WO 05/040396 | 5/2005 | |
| WO | WO 05/085471 | 9/2005 | |
| WO | WO 05/100608 | 10/2005 | |
| WO | WO 06/047484 | 5/2006 | |
| WO | WO 06/091776 | 8/2006 | |
| WO | WO 06/110264 | 10/2006 | |
| WO | WO 06/127537 | 11/2006 | |
| WO | WO 06/135596 | 12/2006 | |
| WO | WO 07/056049 | 5/2007 | |
| WO | WO 07/070621 | 6/2007 | |
| WO | WO 07/081720 | 7/2007 | |
| WO | WO 07/081740 | 7/2007 | |
| WO | WO 08/023087 | 2/2008 | |
| WO | WO 08/046911 | 4/2008 | |
| WO | WO 08/086478 | 7/2008 | |
| WO | WO 08/112283 | 9/2008 | |
| WO | WO 09/009432 | 1/2009 | |
| WO | WO 09/020521 | 2/2009 | |
| WO | WO 09/020905 | 2/2009 | |
| WO | WO 09/029266 | 3/2009 | |
| WO | WO 09/045115 | 4/2009 | |
| WO | WO 09/074968 | 6/2009 | |
| WO | WO 09/108860 | 9/2009 | |
| WO | WO 09/143603 | 12/2009 | |
| WO | WO 10/018601 | 2/2010 | |
| WO | WO 10/056374 | 5/2010 | |
| WO | WO 10/073248 | 7/2010 | |
| WO | WO 10/099598 | 9/2010 | |
| WO | WO 10/123626 | 10/2010 | |
| WO | WO 10/124372 | 11/2010 | |
| WO | WO-2010151842 A2 * | 12/2010 | ........... C12Q 1/6837 |
| WO | WO 11/150453 | 12/2011 | |
| WO | WO 12/031008 | 3/2012 | |
| WO | WO 12/068383 | 5/2012 | |
| WO | WO 12/135008 | 10/2012 | |
| WO | WO 13/006495 | 1/2013 | |
| WO | WO 13/088457 | 6/2013 | |
| WO | WO 13/116472 | 8/2013 | |
| WO | WO 13/116742 | 8/2013 | |
| WO | WO 14/028884 | 2/2014 | |
| WO | WO-2014022826 A2 * | 2/2014 | ........... C12Q 1/6886 |
| WO | WO 14/043803 | 3/2014 | |
| WO | WO 14/085666 | 5/2014 | |
| WO | WO 14/138101 | 9/2014 | |
| WO | WO 14/151764 | 9/2014 | |
| WO | WO 15/024942 | 2/2015 | |
| WO | WO 15/071876 | 5/2015 | |
| WO | WO 15/073949 | 5/2015 | |
| WO | WO 16/141127 | 9/2016 | |
| WO | WO 17/059549 | 4/2017 | |
| WO | WO 17/062505 | 4/2017 | |
| WO | WO 18/161081 | 9/2018 | |
| WO | WO 18/165600 | 9/2018 | |
| WO | WO 19/023517 | 1/2019 | |
| WO | WO 19/133697 | 7/2019 | |

OTHER PUBLICATIONS

Abdueva et al., "Quantitative Expression Profiting in Formalin-Fixed Paraffin-Embedded Samples by Affymetrix Microarrays," Journal of Molecular Diagnostics (Jul. 2010) vol. 12, No. 4, pp. 409-417.

Adamo and Ladomery, "The Oncogene ERG: A Key Factor in Prostate Cancer," *Oncogene*(2016), 35:403-414.

Affymetrix GeneChip Human Genome U133 Array Set HG-U133A, Geo, Mar. 11, 2002, retrieved on Mar. 11, 2002.

Affymetrix, Human Exon 1.0 ST Array—Support Materials, https://www.affymetrix.com/support/technical/byproduct.affx?product=huexon-st, Jan. 1, 2006 (Jan. 1, 2006).

Affymetrix: Data Sheet, "GeneChip® Exon Array System for Human, Mouse, and Rat," Internet Citation, [Online] Jan. 25, 2012 [Retrieved from the Internet] lntp://www.biainformatics.atickland.aciaz/workshops/1O_March_2011 1Exon_EOST_Datash eet.pdf, 8 pages.

(56) References Cited

OTHER PUBLICATIONS

Agell et al., "A 12-Gene Expression Signature Is Associated with Aggressive Histological in Prostate Cancer: SEC14L1 and TCEB1 Genes Are Potential Markers of Progression," Am J Pathol (2012) vol. 181 (5), pp. 1585-1594.
Alberts et al., "Vesicular traffic in the secretory and endocytic pathways," Molecular Biology of the Cell (1994) 3rd Ed., p. 465.
Aldred et al., "Papillary and follicular thyroid carcinomas show distinctly different microarray expression profiles and can be distinguished by a minimum of five genes," J Clin Oncol. (2004) 22(17):3531-9.
Alkhateeb et al., Mar. 13, 2019, Transcriptomics signature from next-generation sequencing data reveals new transcriptomic biomarkers related to prostate cancer, Cancer Informatics, 18:1-12.
Altintas et al., Jun. 2013 Differentially expressed androgen-regulated genes in androgen-sensitive tissues reveal potential biomarkers of early prostate cancer, PLOS One, 8(6):e66278.
Amling et al.: "Long-term hazard of progression after radical prostatectomy for clinically EB localized prostate cancer continued risk of biochemical failure after 5 years," J Urol. (2000) 164:101-105.
Amundadottir et al., "A common variant associated with prostate cancer in European and African populations," Nat Genet. (2006) 38:652-658.
Amundson et al., "Integrating global gene expression and radiation survival parameters across the 60 cell lines of the National Cancer Institute Anticancer Drug Screen," Cancer Research (2008) 68(2):415-424.
Anonymous, UCSC Genome Browser on Human Mar. 2006, NCBI36/hg18) Assembly, Mar. 2006, XP055587638, Retrieved from the Internet: URL:https://genome-euro.ucsc.edu/cgi-bin/hgTracks?db=hg18&lastVirtModeType=default&lastVirtModeExtraState=&virtModeType=default&virtMode=0&nonVirtPosition=&position=chr5%3A 14025126%2D14062770&hgsid=232148223_IYIy9VS0Lh0jhldEBQ3nViBrQuB5 [retrieved on May 10, 2019].
Ateeq et al., Mar. 2, 2011, Therapeutic targeting of SPINK1-positive prostate cancer, Sci Transl Med, 3(72):1-18.
Ausubel, et al. Current Protocols in Molecular Biology. Wiley & Sons, New York (1995) Table of Contents.
Baetke et al., "Molecular Pathways Involved in Prostate Carcinogenesis: Insights from Public Microarray Datasets," PLoS One (2012) 7(11):e49831, 1-11.
Baggerly et al., "Deriving Chemosensitivity from Cell Lines: Forensic Bioinformatics and Reproducible Research in High-Throughput Biology," The Annals of Applied Sciences (2009) vol. 3, No. 4, pp. 1309-1334.
Ballman et al., "Faster cyclic loess: normalizing RNA arrays via linear models," Bioinformatics, 2004, 20 :2778-2786.
Bannert et al., "Retroelements and the human genome: new perspectives on an old relation." PNAS (Oct. 5, 2004) vol. 101, Suppl. 2, pp. 14572-14579.
Barlow et al., "Analysis of Case-Cohort Designs," J Clin Epidemiol (1999) vol. 52 (12), 1165-1172.
Bauer et al., "Identification of Markers of Taxane Sensitivity Using Proteomic and Genomic Analyses of Breast Tumor from Patients Receiving Neoadjuvant Paclitaxel and Radiation," Clin. Cancer Res. (2010) 16(2):681-690, American Association for Cancer Research.
Becht et al., Oct. 20, 2016, Estimating the population abundance of tissue-infiltrating immune and stromal cell populations using gene expression, Gemone Biology, 52(Suppl 2):218.
Benner et al., "Evolution, language and analogy in functional genomics," Trends in Genetics, (Jul. 2001) vol. 17, pp. 414-418.
Bergstralh et al., "Software for optimal matching in observation al studies," Epidemiology (1996) 7(3):331-332.
Best et al., "Molecular differentiation of high- and moderate-grade human prostate cancer by cDNA microarray analysis", Diagn Mol Pathol. (2003) 12(2):63-70.
Bhaskar et al., Oct. 1, 2003, E-selective up-regulation allows for targeted drug delivery in prostate cancer, Cancer Research 63:6387-6394.
Bibikova et al., "Expression signatures that correlated with Gleason score and relapse in prostate cancer," Genomics (2007) 89(6):666-672.
Bibikova et al., "Gene expression profiles in formalin-fixed, paraffin-embedded tissues obtained with a novel assay for microarray analysis," Clin Chem., 2004, 50:2384-2386.
Bibikova et al., "Quantitative gene expression profiling in formalin-fixed, paraffin-embedded tissues using universal bead arrays," Am J Pathol. (2004) 165:1799-1807.
Birney et al., "Identification and analysis of functional elements in 1% of the human genome by the Encode pilot project." Nature Jun. 14, 2007; 447(7146):799-816.
Bismar et al., "ERG Protein Expression Reflects Hormonal Treatment Response and is Associated with Gleason Score and Prostate Cancer Specific Mortality," *Eur. J. Cancer* (2012), 48:538-546, Elsevier Ltd.
Biton et al., Nov. 20, 2014, Independent component analysis uncovers the landscape of the bladder tumor transcriptome and reveals insights into luminal and basal subtypes, Cell Reports, 9(4):1235-1245.
Blute et al., "Use of Gleason score, prostate specific antigen, seminal vesicle and margin status to predict biochemical failure after radical prostatectomy," J Urol (2001) 165: 119-125.
Boorjian et al., "Long-term risk of clinical progression after biochemical recurrence following radical prostatectomy: the impact of time from surgery to recurrence." Eur Urol. (Jun. 2011) 59(6):893-9.
Boormans et al., "Identification of TDRD1 as a direct target gene of ERG in primary prostate cancer," Int J Cancer (2013) vol. 133 (2), pp. 335-345.
Bostwick et al., "Prognostic factors in prostate cancer: College of American Pathologists consensus statement," Arch Pathol Lab Med (2000) 124(7):995-1000.
Bott et al., "Prostate cancer management: (2) an update on locally advanced and metastatic disease", Postgrad Med J, Dec. 3, 2003, 79(937), 643-645.
Brase et al., "TMPRSS2-ERG—specific transcriptional modulation is associated with prostate cancer biomarkers and TGF-β signaling," BMC Cancer (2011) 11(507):1-8.
Breiman, "Random Forests," Machine Learning (2001) 45:5-32.
Brouha et al., "Hot L1s account for the bulk of retrotransposition in the human population." PNAS USA (Apr. 29, 2003) 100(9):5280-5.
Bueno et al., "A diagnostic test for prostate cancer from gene expression profiling data," J Urol, Feb. 2004; 171(2 Pt 1):903-6.
Bull et al., "Identification of potential diagnostic markers of prostate cancer and prostatic intraepithelial neoplasia using cDNA microarray," British J Cancer (Jun. 1, 2001) 84(11):1512-1519.
Bussemakers et al., "DD3: a new prostate-specific gene, highly overexpressed in prostate cancer." Cancer Res. (Dec. 1, 1999) 59(23):5975-9.
Carninci et al., "The transcriptional landscape of the mammalian genome," Science (Sep. 2, 2005) 09(5740):1559-63.
Cerutti et al. "Diagnosis of suspicious thyroid nodules using four protein biomarkers," Clin Cancer Res. (2006) 12(11 Pt 1):3311-8.
Chalitchagorn et al., "Distinctive pattern of LINE-1 methylation level in normal tissues and the association with carcinogenesis." Oncogene (Nov. 18, 2004) 23(54):8841-6.
Che et al.: "Prognostic Value of Abnormal p53 Expression in Locally Advanced Prostate Cancer Treated With Androgen Deprivation and Radiotherapy: A Study Based on RTOG 9202"; International Journal of Radiation: Oncology Biology Physics (Nov. 15, 2007) vol. 69, No. 4, pp. 1117-1123.
Chen et al., "Deregulation of a Hox Protein Regulatory Network Spanning Prostate Cancer Initiation and Progression," Clin Cancer Res (Jun. 2012) 18(16):4291-4302.
Chen et al., "Hepsin and maspin are inversely expressed in laser capture microdissectioned prostate cancer," J Urol. (Apr. 2003) 169(4):1316-1319.
Chen et al., "Significance of noninvasive diagnosis of prostate cancer with cytologic examination of prostatic fluid," J Nippon Med Sch. (Jun. 2006) 73(3):129-135.

(56) References Cited

OTHER PUBLICATIONS

Chen et al., 2002, Discordant protein and mRNA expression in lung adenocarcinomas, Molecular & Cellular Proteomics 1.4, pp. 304-313.
Chen et al.: "Molecular determinants of resistance to antiandrogen therapy"; Nature Medicine, Nature Publishing Group, New York, NY (Jan. 1, 2004) vol. 10, No. 1, pp. 33-39.
Cheng et al. "Cell Proliferation in Prostate Cancer Patients with Lymph Node Metastasis", Clin Cancer Res (Oct. 1999) 5(10): 2820-2823.
Cheung et al., "Natural variation in human gene expression assessed in lymphoblastoid cells," Nature Genetics (2003) vol. 33, pp. 422-425.
Cheville et at., "Gene Panel Model Predictive of Outcome in Men at High-Risk of Systemic Progression and Death From Prostate Cancer After Radical Retropubic Prostatectomy," Journal of Clinical Oncology (Aug. 20, 2008) vol. 26, No. 24.
Chifman et al., "Conservation of immune gene signatures in solid tumors and prognostic implications," BMC Cancer (2016) 16:911, pp. 1-17. DOI 10.1186/S12885-016-2948-Z.
Cho et al., "Hypermethylation of CpG island loci and hypomethylation of LINE-1 and Alu repeats in prostate adenocarcinoma and their relationship to clinicopathological features", J Pathol (Feb. 2007) 211(3):269-77.
Choi et al., Feb. 2014, Identification of distinct basal and luminal subtypes of muscle-invasive bladder cancer with different sensitivities to frontline chemotherapy, Cancer Cell, 25(2):152-165.
Choi et al., Jun. 24, 2014, Intrinsic basal and luminal subtypes of muscle-invasive bladder cancer, Nature Reviews Urology, 11(7):400-410.
Chow et al., "LINE-1 activity in facultative heterochromatin formation during X chromosome inactivation," Cell (Jun. 11, 2010) 141(6):956-69.
Cibas, et al. "The Bethesda System for Reporting Thyroid Cytopathology," Am J Clin Pathol. (Nov. 2009) 132(5):658-65. doi: 10.1309/AJCPPHLWMI3JV4LA.
Clancy et al., "Profiling networks of distinct immune-cells in tumors," BMC Bioinformatics (2016) 17:263, pp. 1-15. DOI 10.1186/s12859-016-1141-3.
Clark-Langone et al. "Biomarker discovery for colon cancer using a 761 gene RT-PCR assay 2007," BMC Genomics (2007) 8:279 pp. 1-18.
Cologne et al., "Optimal Case-Control Matching in Practice," Epidemiology Resources Inc. (1995) 6(3):271-275.
Cooper et al., "Mechanisms of Disease: biomarkers and molecular targets from microarray gene expression studies in prostate cancer ," Nat Clin Pract Urol. (2007) Dee:4(12):677-87.
Cooperberg et al., "The CAPRA-S score: A straightforward tool for improved prediction of outcomes after radical prostatectomy," Cancer (2011) vol. 117 (22), pp. 5039-5046.
Cordaux et al., "The impact of retrotransposons on human genome evolution." Nat Rev Genet. (Oct. 2009) 10(10):691-703.
Cordon-Cardo et al., "Improved prediction of prostate cancer recurrence through systems pathology," The Journal of Clinical Investigation (Jul. 2007) vol. 117, No. 7, pp. 1876-1883.
Couzin-Frankel, Jennifer, "As Questions Grow, Duke Halts Trials, Launches Investigation," Science (Aug. 6, 2010) vol. 329, pp. 614-615.
Cuzik et al., "Prognostic value of an RNA expression signature derived from cell cycle proliferation genes in patients with prostate cancer: a retrospective study," thelancet.com/oncology (Mar. 2011) vol. 12, pp. 245-255.
Dahlman et al., "Effect of androgen deprivation therapy on the expression of prostate cancer biomarkers MSMB and MSMB-binding protein CRISP3," Prostate Cancer and Prostatic Diseases (2010) 13:369-375.
Dalela et a., Jun. 20, 2017, Genomic classifier augments the role of pathological features in identifying optimal candidates for adjuvant radiation therapy in patients with prostate cancer: development and internal validation of a multivariable prognostic model, Journal of Clinical Oncology, 35(18):1982-1990.
Dalela et al., "Contemporary Role of the Decipher Test in Prostate Cancer Management: Current Practice and Future Perspectives," Rev. Urol. (2016), 18(1):1-9, MedReviews®, LLC.
Dalsgaard Sorensen et al.: "Discovery of prostate cancer biomarkers by microarray gene expression profiling"; Expert Review of Molecular Diagnostics, vol. 10, No. 1, Jan. 1, 2010, pp. 49-64.
D'Amico et al., "Cancer-specific mortality after surgery or radiation for patients with clinically localized prostate cancer managed during the prostate-specific antigen era," J Clin Oncol. (2003) 21:2163-2172.
D'Amico et al., "Determinants of prostate cancer-specific survival after radiation therapy for patients with clinically localized prostate cancer," J Clin Oncol. (2002) 20:4567-4573.
Damrauer et al., Feb. 25, 2014, Intrinsic subtypes of high-grade bladder cancer reflect the hallmarks of breast cancer biology, Proc Natl Acad Sci USA, 111(8):3110-3115.
Dawood, Shaheenah, "Novel Biomarkers of Metastatic Cancer," Expert Rev. Mo/. Diagn. (2010) 10(5):581-590, Expert Reviews Ltd.
Day et al., "Estimating enrichment of repetitive elements from high-throughput sequence data." Genome Biol. (2010) 11 (6):R69.
De Klein et al., "A cellular oncogene is translocated to the Philadelphia chromosome in chronic myelocytic leukaemia." Nature (Dec. 23, 1982) 300(5894):765-7.
De Marzo et al., "Pathological and molecular mechanisms of prostate carcinogenesis: implications for diagnosis, detection, prevention, and treatment," J Cell Biochem. (Feb. 15, 2004) 91(3):459-477.
Dechassa et al., "Architecture of the SWI/SNF-nucleosome complex," Mol Cell Biol. (Oct. 2008) vol. 28, No. 19, pp. 6010-6021.
Demichelis et al., "TMPRSS2:ERG gene fusion associated with lethal prostate cancer in a watchful waiting cohort," Oncogene (2007) 26:4596-4599.
Den et al., Mar. 10, 2015, Genomic classifier identifies men with adverse pathology after racial prostatectomy who benefit from adjuvant radiation therapy, Journal of Clinical Oncology, 33(8):944-951.
Dhanasekaran et al., "Delineation of prognostic biomarkers in prostate cancer," Nature (2001) 412:822-826.
Dhani et al., 2011, Phase II study of cytarabine in men with docetaxel-refractory, castration-resistant prostate cancer with evaluation of TMPRSS2-ERG and SPINK1 as serum biomarkers, BJUI, 110:840-845.
Dougherty, "The fundamental role of pattern recognition for gene-expression/microarray data in bioinformatics," Pattern recognition (2005) 38:2226-2228.
Droz et al., Aug. 2014, Management of prostate cancer in older patients: updated recommendations of a working group of the International Society of Geriatric Oncology, The Lancet, 15:e404-e414.
Eder et al., "Genes differentially expressed in prostate cancer," BJU Int. (May 2004) 93(8): 1151-1155.
Edwards et al., "Expression analysis onto microarrays of randomly selected cDNA clones highlights HOXB13 as a marker of human prostate cancer," Br J Cancer. (Jan. 31, 2005) 92(2):376-381.
Edwards et al.: "MicroRNAs and Ultraconserved Genes as Diagnostic Markers and Therapeutic Targets in Cancer and Cardiovascular Diseases", Journal of Cardiovascular Translational Research (May 5, 2010) vol. 3, No. 3, pp. 271-279.
Englisch, et al., "Chemically Modified Oligonucleotides as Probes and Inhibitors," Angew. Chem. Int. Ed. Eng. (1991) 30:613-629.
Epstein et al., "Prognostic factors and reporting of prostate carcinoma in radical AU prostatectomy and pelvic lymphadenectomy specimens," Scand. J. Urol. Nephrol. Suppl. (2005) 216:34-63.
Erho et al., "Discovery and Validation of a Prostate Cancer Genomic Classifier that Predicts Early Metastasis Following Radical Prostatectomy," PLoS One (2013) 8(6):e66855, 1-12.
Ernst et al., "Decrease and gain of gene expression are equally discriminatory markers for prostate carcinoma: a gene expression analysis on total and microdissected prostate tissue," Am J Pathol. (Jun. 2002) 160(6):2169-2180.

(56) References Cited

OTHER PUBLICATIONS

Etzioni et al. "The case for early detection", Nature Reviews | Cancer (Apr. 2003) vol. 3, pp. 1-10.
Fan et al., "Concordance among gene-expression-based predictors for breast cancer," N Engl J Med. (2006) 355:560-569.
Feng et al., "Luminal and basal subtyping of prostate cancer," *J Clin Oncol* (Feb. 20, 2017) 35(6).
Feroze-Merzoug et al., "Molecular profiling in prostate cancer," Cancer Metastasis Rev. 1 (2001) 20(3-4):165-71.
Fine et al., "A Proportional Hazards Model for the Subdistribution of a Competing Risk," Journal of the American Statistical Association (1999) vol. 94 (446), pp. 496-509.
Finley et al., "Advancing the molecular diagnosis of thyroid nodules: defining benign lesions by molecular profiling," Thyroid (2005) 15(6):562-8.
Finley et al., "Discrimination of benign and malignant thyroid nodules by molecular profiling," Ann Surg. (2004) 240(3):425-36; discussion 436-7.
Fischer et al., Sep. 2, 2019, A radiogenomic approach for decoding molecular mechanisms underlying tumor progression prostate cancer, Cancers, 11(9), 18 pp.
Fodor et al., "Light-directed, spatially addressable parallel chemical synthesis," Science (Feb. 15, 1991) 251(4995):767-773.
Foley et al., "Molecular pathology of prostate cancer: the key to identifying new biomarkers of disease," Endocrine-Related Cancer (2004) 11:477-488.
Fontaine, et al., "Increasing the number of thyroid lesions classes in microarray analysis improves the relevance of diagnostic markers," PLoS One (Oct. 29, 2009) 4(10):e7632. doi: 10.1371/journal.pone.0007632.
Forker et al. 2015, Biomarkers of Tumour Radiosensitivity and Predicting Benefit from Radiotherapy, 27: 561-569.
Fridman et al., Jul. 25, 2017, The immune contexture in cancer prognosis and treatment, Nature Reviews Clinical Oncology, 14:717-734.
Fryknas et al., "Molecular markers for discrimination of benign and malignant follicular thyroid tumors," Tumour Biol. (2006) 27(4):211-20.
Fu et al., "Regulation of apoptosis by a prostate-specific and prostate cancer-associated noncoding gene, PCGEM1." DNA Cell Biol. (Mar. 2006) 25(3): 135-41.
Fujarewicz et al., "A multi-gene approach to differentiate papillary thyroid carcinoma from benign lesions: gene selection using support vector machines with bootstrapping," Endocr Relat Cancer (Sep. 2007) 14(3):809-26.
Gait. Chapter 16: Oligoribonucleotides. Antisense Research and Applications, Crooke and Lebleu Eds., CRC Press (1993) pp. 289-302.
Galamb et al., "Diagnostic mRNA Expression Patterns of Inflamed, Benign, and Malignant Colorectal Biopsy Specimen and their Correlation with Peripheral Blood Results," Cancer Epidemiology, Biomarkers & Prevention (Oct. 2008) 17(10):2835-2845.
Galavotti et al., Apr. 2012, The autophagy-associated factors DRAM1 and p62 regulate cell migration and invasion in glioblastoma stem cells, Oncogene, 32:699-712.
Gao et al. 2019, DeepCC: a novel deep learning-based framework for cancer molecular subtype classification. Oncogenesis, 8(44):1-12.
Gao et al., "Vista is an inhibitory immune checkpoint that is increased after ipilimumab therapy in patients with prostate cancer," Nat Med. (May 2017) 23(5):551-555.
Garber et al., "Diversity of gene expression in adenocarcinoma of the lung," PNAS (Nov. 20, 2001) vol. 98, No. 24, pp. 13784-13789.
Genevieve de Saint Basile et al., "Severe Combined Immunodeficiency Caused by Deficiency in Either the Ii or the E Subunit of CD3," Journal of Clinical Investigation (2004) vol. 114, No. 10. p. 1512-1517.
Gentles et al., Jul. 20, 2015, The prognostic landscape of genes and infiltrating immune cells across human cancers, Nature Medicine, 21(8):938-945.
Gibb et al., "The functional role of long non-coding RNA in human carcinomas", Molecular Cancer, Biomed Central, London, GB (Apr. 13, 2011) vol. 10, No. 1, p. 38.
Giordano et al., "Organ-Specific Molecular Classification of Primary Lung, Colon, and Ovarian Adenocarcinomas Using Gene Expression Profiles," Am J Pathol (2001) 159(4):1231-1238.
Gleason: "Histologic grading and clinical staging of prostatic carcinoma", Urologic pathology: the prostate, (Tannenbaum, ed.) (1977) Lea & Febiger, Philadelphia, PA, pp. 171-197.
Gleason: "Histologic grading of prostate cancer: a perspective"; Hum. Pathol. (1992) 23(3):273-279.
Gleave et al., "Randomized comparative study of 3 versus 8-month neoadjuvant hormonal therapy before radical prostatectomy : biochemical and pathological effects," J Urol. (2001) 166:500-507.
Glinsky et al., "Gene expression profiling predicts clinical outcome of prostate cancer," J Clin Investigation (2004) 113(6):913-923.
Glinsky et al., "Microarray analysis identifies a death-from-cancer signature predicting therapy i failure in patients with multiple types of cancer," J Clin Invest. (2005) 115: 1503-1521.
Gonzalgo et al: "Molecular pathways to prostate cancer"; J Urol. (2003) 170(6 Pt 1):2444-2452.
Gore et al., Aug. 1, 2017, Decipher test impacts decision making among patients considering adjuvant and salvage treatment after radical prostatectomy: interim results from the multicenter prospective Pro-Impact study, Cancer, pp. 2850-2959.
Grambsch et al., "Proportional Hazards Tests and Diagnostics Based on Weighted Residuals," Biometrika (2013) vol. 81 (3), pp. 515-526.
Greenbaum et al.: "Comparing protein abundance and mRNA expression levels on a genomic scale"; Genome Biology (2003) 4(9):117.1-117.8.
Griffith et al., "Meta-analysis and meta-review of thyroid cancer gene expression profiling studies identifies important diagnostic biomarkers," J Clin Oncol. (2006) 24(31):5043-51.
Griffith, et al. Biomarker panel diagnosis of thyroid cancer: a critical review. Expert Rev Anticancer Ther. (Sep. 2008) 8(9):1399-413. doi: 10.1586/14737140.8.9.1399.
Gupta et al., "Long non-coding RNA Hotair reprograms chromatin state to promote cancer metastasis," Nature (Apr. 15, 2010) 464(7291): 1071-6.
Guttman et al., "Ab initio reconstruction of transcriptomes of pluripotent and lineage committed cells reveals gene structures of thousands of lincRNAs," Nat Biotechnol. (May 2010) 28(5):503-10.
Guttman et al., "Chromatin signature reveals over a thousand highly conserved large non-coding RNAs in mammals", Nature (Mar. 12, 2009) 458(7235):223-7.
Ha et al., Nov. 12, 2009, Comparison of affymetrix gene array with the exon array shows potential application for detection of transcript isoform variation, BMC Genomics, 19(1):519.
Haiman et al.: "Multiple regions within 8q24 independently affect risk for prostate cancer"; Nat Genet. (2007) 39:638-644.
Halvorson et al., 2018, Interpreting GLM results: making sense of some odd ratios: a tutorial and improvements to present practices in reporting and visualizing quantities of interest for binary and count outcome models, National Research Service Award, NIH, pp. 1-39.
Hamada et al., "Diagnostic usefulness of PCR profiling of the differentially expressed marker genes in thyroid papillary carcinomas," Cancer Lett. (Jun. 28, 2005) 224(2):289-301. Epub Nov. 18, 2004.
He et al., "The antisense transcriptomes of human cells", Science (Dec. 19, 2008) 322(5909): 1855-7.
Heagerty et al., "Time-Dependent ROC Curves for Censored Survival Data and a Diagnostic Marker," Biometrics (2000) vol. 56 (2), pp. 337-344.
Heemers, H. V. et al.: "Identification of a Clinically Relevant Androgen-Dependent Gene Signature in Prostate Cancer"; Cancer Research, vol. 71, No. 5 (2011) pp. 1978-1988.
Heidenreich et al., "EAU Guidelines on Prostate Cancer. Part 1: Screening, Diagnosis, and Treatment of Clinically Localised Disease," European Urology (2011) vol. 59, pp. 61-71.
Henrotin et al.: "Type II collagen peptides for measuring cartilage degradation," Biorheology (2004) 41 (3-4): Abstract.

(56) References Cited

OTHER PUBLICATIONS

Henshall et al., "Survival Analysis of Genome-Wide Gene Expression Profiles of Prostate cancers Identifies New Prognostic Targets of Disease Relapse," Cancer Research (Jul. 15, 2003) 63, 14196-4203.
Holzbeierlein et al., "Gene expression analysis of human prostate carcinoma during hormonal therapy identifies androgen-responsive genes and mechanisms of therapy resistance," Am. J . Pathol. (Jan. 2004) 164(1):217-227.
Hornberger et al., "A Multigene Prognostic Assay for Selection of Adjuvant Chemotherapy in Patients with T3, Stage II Colon Cancer: Impact on Quality-Adjusted Life Expectancy and Costs," Value in Health 15 (2012) pp. 1014-1021.
Huarte et al., "Large non-coding RNAs: missing links in cancer?" Human Molecular Genetics (Oct. 15, 2010) 19(2): R152-R161.
Hughes et al., "Molecular pathology of prostate cancer," J Clin Pathol. (Jul. 2005) 58(7):673-684.
Hughes et al., "Topoisomerase II—a expression increases with increasing Gleason score and with hormone insensitivity in prostate carcinoma," J Clin Pathol. (Jul. 2006) 59(7): 721-724.
Humphrey et al: "Histologic grade, DNA ploidy, and intraglandular tumor extent as indicators of tumor progression of clinical Stage B prostatic carcinoma"; Am J Surg Pathol (1991) 15(12):1165-1170.
Ida et al., "Topoisomerase II alpha protein expression Is predictive of outcome in Gleason score 7 prostate cancer patients treated surgically and is dependent on ERG status." Mod Pathol. (Feb. 2010) Abstract 1895, 23 : 424A-425A.
Iljin et al., Nov. 1, 2006, TMPRSS2 fusions with oncogenic ETS factors in prostate cancer involve unbalanced genomic rearrangements and are associated with HDAC1 and epigenetic reprogramming, Cancer Res., 66(21):10242-10246.
Inamura, Apr. 2018, Bladder Cancer: new insights into its molecular pathology, Cancers (Basel), 10(4):100.
Ito et al., "Linkage of elevated ets-2 expression to hepatocarcinogenesis," Anticancer Research (2002) 22(4):2385-2389.
Jemal et al.: "Cancer statistics," CA Cancer J Clin. (2005) 55:10-30.
Jenkins et al., "Prognostic significance of ailetic imbalance of chromosome arms 71, 8p, 16q, and 18q in stage T3NOMO prostate cancer," Genes, Chromosomes & Cancer (1998) 21:131-143.
Jhavar et al., "Integration of ERG gene mapping and gene-expression profiling identifies distinct categories of human prostate cancer," BJUI (2008) vol. 103 (9), pp. 1256-1269.
Jhavar et al., "Technical Advance: Detection of TMPRSS2-ERG Translocations in Human Prostate Cancer by Expression Profiling Using GeneChip Human Exon 1.0 ST Arrays," J Mol. Diag (Jan. 2008) vol. 10, No. 1, pp. 50-57.
Jones et al., "Frequent mutations of chromatin remodeling gene ARID1A in ovarian clear cell carcinoma" Science (Oct. 8, 2010) 330(6001):228-31.
Kaikkonen et al., 2018, ANO7 is associated with aggressive prostate cancer, Int. J. Cancer, 143:479-2487.
Kanehisa, "Use of statistical criteria for screening potential homologies in nucleic acid sequences," Nucleic Acids Res. (Jan. 11, 1984) 12(1 Pt 1):203-13.
Karan et al., "Current status of the molecular genetics of human prostatic adenocarcinomas," Int J Cancer, 2003, 103(3):285-293.
Karayi et al., "Molecular biology of prostate cancer," Prostate Cancer Prostatic Dis. (2004) 7(1):6-20.
Karnes et al., "Radical prostatectomy for high-risk prostate cancer," Jpn. J. Clin. Oneal. (Oct. 19, 2009) 40 (1): 3-9, Epub.
Karnes et al., "The ability of biomarkers to predict systemic progression in men with high-risk prostate cancer treated surgically is dependent on ERG status," Cancer Res. (Nov. 9, 2010) 70(22):8994-9002, Epub.
Kasraeian, et al. , "A comparison of fine-needle aspiration, core biopsy, and surgical biopsy in the diagnosis of extremity soft tissue masses," Clin Orthop Relat Res. (Nov. 2010) 468(11):2992-3002.
Kawamorita et al., "Radical prostatectomy for high-risk prostate cancer: Biochemical outcome," International Journal of Urology (2009) 16:733-738.

Kebebew et al., "Diagnostic and extent of disease multigene assay for malignant thyroid neoplasms," Cancer (2006) 106(12):2592-7.
Kelly et al., 2012, Agreement in Risk Prediction Between the 21-Gene Recurrence Score Assay (Oncotype DX) and the PAM50 Breast Cancer Intrinsic Classifier™ in Early-Stage Estrogen Receptor-Positive Breast Cancer, The Oncologist, 17:492-498.
Kestin, "Potential survival advantage with early androgen deprivation for biochemical failure after external beam radiotherapy: the importance of accurately defining biochemical disease status," Int J Rad Oncol Biol Phys. (2004) 60:453-62.
Khor et al.: "Bcl-2 and Bax Expression Predict Prostate Cancer Outcome in Men Treated with Androgen Deprivation and Radiotherapy on Radiation Therapy Oncology Group Protocol 92-02"; Clinical Cancer Research (Jun. 15, 2007) vol. 13, No. 12, pp. 3585-3590.
Kiessling, et al., "D-TMPP: A novel androgen-regulated gene preferentially expressed in prostate and prostate cancer that is the first characterized member of an eukaryotic gene family," The Prostate (2005) 64:387-400.
Kikuchi et al., "Expression profiles of non-small cell lung cancers on cDNA microarrays: identification of genes for prediction of lymph-node metastasis and sensitivity to anti-cancer drugs," Oncogene (2003) 22, pp. 2192-2205.
Kishi et al., "Expression of the surviving gene in prostate cancer: correlation with clinicopathological characteristics, proliferative activity and apoptosis," J Urol. (May 2004) 171(5): 1855-1860.
Klee et al., "Candidate Serum Biomarkers for Prostate Adenocarcinoma identified by mRNA Differences in Prostate Tissue and Verified with Protein Measurements in Tissue and Blood," Clinical Chemistry (2012) 58(3):599-609.
Knowles et al., Dec. 23, 2014, Molecular biology of bladder cancer: new insights into pathogenesis and clinical diversity, Nature Reviews Cancer, 15(1):25-41.
Kosari et al., "Identification of biomarkers for prostate cancer," Clin. Cancer Res. (2008) 1734-1743.
Koshkin et al., "LNA (locked nucleic acids): An RNA mimic forming exceedingly stable LNA," LNA duplexes. J Am Chem Soc (1998) 120:13252-13253.
Koshkin et al., "LNA (locked nucleic acids): synthesis of the adenine, cytosine, guanine 5-methylcytosine, thymine and uracil bicyclonucleoside monomers, oligomerisation, and unprecedented nucleic acid recognition," Tetrahedron (1998) 54(14):3607-3630.
Kronick, 2004, Creation of the whole human genome microarray, Expert Review of Proteomics, 1:19-28.
Kroschwitz the Concise Encyclopedia of Polymer Science and Engineering (1990) (pp. 858-859).
Kube et al., "Optimization of laser capture microdissection and RNA amplification for gene expression profiling of prostate cancer," BMC Mol. Biol. (2007) 8:25.
Kumar, et al., "The first analogues of LNA (locked nucleic acids): phosphorothioate-LNA and 2'-thio-LNA," Bioorg Med Chem Lett. (Aug. 18, 1998) 8(16):2219-22.
Kumar-Sinha et al., "Molecular markers to identify patients al risk for recurrence after primary treatment for prostate cancer," Urology, 62 Suppl 1:19-35, Dec. 29, 2003.
Kunarso et al., "Transposable elements have rewired the core regulatory network of human embryonic stem cells," Nat Genet (Jul. 2010) 42(7):631-4.
Landers et al.: "Use of multiple biomarkers for a molecular diagnosis of prostate cancer"; Int. J. Cancer (May 10, 2005) 114 pp. 950-956.
Lapointe et al., "Gene expression profiling identifies clinically relevant subtypes of prostate cancer," PNAS USA (2004) 101:811-816.
Latulippe et al., "Comprehensive Gene Expression Analysis of Prostate Cancer Reveals Distinct Transcriptional Programs Associated with Metastatic Disease," Cancer Res. (2002) 62:4499-4506.
Lawton et al., "Updated results of the phase III Radiation Therapy Oncology Group (RTOG) trial 85-31 evaluating the potential benefit of androgen suppression following standard radiation therapy for unfavorable prognosis carcinoma of the prostate," Int J Rad Oncol Biol Phys. (2001) 49:937-946.

(56) References Cited

OTHER PUBLICATIONS

Leyten et al., "Identification of a Candidate Gene Panel for the Early Diagnosis of Prostate Cancer," Clinical Cancer Research (2015) 21(13):3061-3070.
Lin et al., "Cox Regression with Incomplete Covariate Measurements," Journal of the American Statistical Association (1993) vol. 88 (424), pp. 1341-1349.
Lin et al., "Nuclear receptor-induced chromosomal proximity and DNA breaks underlie specific translocations in cancer," Cell (Dec. 11, 2009) 139(6):1069-83.
Liong et al., "Blood-Based Biomarkers of Aggressive Prostate Cancer," PLoS One (Sep. 2012) vol. 7, Issue 7, e45802, pp. 1-7.
Litwin et al., Jun. 27, 2017, The diagnosis and treatment of prostate cancer: a review, JAMA, 317(24):2532-2542.
Liu et al., 2014, Synergistic killing of lung cancer cells by cisplatin and radiation via autophagy and apoptosis, Oncology Letters, 7:1903-1910.
Livingston et al., "*Homo sapiens* CDC20 Cell Division Cycle 20 Homolog (CDC20)," Gene (Apr. 24, 2006).
Lockstone, "Exon array data analysis using Affymetrix power tools and R statistical software," Briefings in bioinformatics (2011) vol. 12 (6), pp. 634-644.
Lunardi et al., "A co-clinical approach identified mechanisms and potential therapies for androgen deprivation resistance in prostate cancer," Nature Genetics (Jul. 2013) vol. 45, No. 7, pp. 747-757.
Luo et al., "Gene expression analysis of prostate cancers," Molecular Carcinogenesis (Jan. 2002) 33(1):25-35.
Luo et al., "Human Prostate Cancer and Benign Prostatic Hyperplasia : Molecular Dissection by Gene Expression Profiling," Cancer Res. (2001) 61:4683-4688.
Magee et al., "Expression Profiling Reveals Hepsin Overexpression in Prostate Cancer," Cancer Res. (2001) 61:5692-5696.
Martens-Uzunova, E. S. et al.: "Diagnostic and prognostic signatures from the small non-coding RNA transcriptome in prostate cancer", Oncogene (Jul. 18, 2011) vol. 31, No. 8, pp. 978-991.
Martin, "A New Access to 2'-O-Alkylated Ribonucleosides and Properties of 2'-O-Alkylated Oligoribonucleotides," Helv. Chim. Acta. (1995) 78:486-504. (in German with English abstract).
Marx et al., Jan.-Mar. 2021, Reduced anoctamin 7 (ANO7) expression is a strong and independent predictor of poor prognosis in prostate cancer, Cancer Biol Med, 18(1):245-255.
Mazzanti, et al., "Using gene expression profiling to differentiate benign versus malignant thyroid tumors," Cancer Res. (Apr. 15, 2004) 64(8):2898-903.
McArdle et al., 2004, The relationship between T-lymphocyte subset infiltration and survival in patients with prostate cancer, British Journal of Cancer, 91:541-543.
McCall et al., "Frozen robust multiarray analysis (fRMA)", Biostatistics (2010) vol. 11 (2), 242-253.
McConkey et al., Apr. 2015, Therapeutic opportunities in the intrinsic subtypes of muscle-invasive bladder cancer, Hematology/Oncology Clinics of North America, 29(2):377-394.
McConkey et al., May 2016, A prognostic gene expression signature in the molecular classification of chemotherapy-naïve urothelial cancer is predictive of clinical outcomes from neoadjuvant chemotherapy: a phase 2 trial of dose-dense methotrexate, vinblastine, doxorubicin, and cisplatin with bevacizumab in urothelial cancer, European Urology, 69(5):855-862.
Mendiratta et al., "Genomic signatures associated with the development, progression, rand outcome of prostate cancer," Molecular diagnosis & therapy (2007) 11(6):345-54.
Mercer, DW, "Use of multiple markers to enhance clinical utility", Immunol Ser. (1990) 53: 39-54.
Metsala et al., 2023, Progression-association with an aggressive phenotype? Cancer Res., 83(11_Supplement):A010.
Michiels et al. 2005, Prediction of cancer outcome with microarrays: a multiple random validation strategy, Lancet, 365:488-492.
Mineva et al., "Differential expression of alphaB-crystallin and Hsp27-1 in anaplastic thyroid carcinomas because of tumor-specific alphaB-crystallin gene (CRYAB) silencing," Cell Stress Chaperones (Autumn 2005) 10(3):171-84.
Mitelman, "Recurrent chromosome aberrations in cancer," Mutation Research (2000) 462: 247-253.
Montironi et al., "Carcinoma of the prostate: inherited susceptibility, somatic gene defects and androgen receptors," Virchows Arch. (Jun. 2004) 444(6):503-508.
Moul et al., "Early versus delayed hormonal therapy for prostate specific antigen only recurrence of prostate cancer after radical prostatectomy," J Urol. (2004) 171:1141-1147.
Moul, "Prostate specific antigen only progression of prostate cancer," J Urol. (2000) 163:1632-42.
Mühlenbruch et al., "Multiple imputation was a valid approach to estimate absolute risk from a prediction model based on case-cohort data," Journal of Clinical Epidemiology (2017) 84:130-141.
Nakagawa et al., "A Tissue Biomarker Panel Predicting Systemic Progression after PSA Recurrence Post-Definitive Prostate Cancer Therapy," PLos One (2008) 3(5):e2318, 14 pages.
Nelson, "Predicting prostate cancer behavior using transcript profiles," J Urol. (Nov. 2004) 172(5 Pt 2):S28-32; discussion S33.
Nevins et al., Aug. 2007, Mining gene expression profiles: expression signatures as cancer phenotypes, Genetics, 8:601-609.
Newman et al., May 2015, Robust enumeration of cell subsets form tissue expression profiles, Nature Methods, 12(5):453-457 with online methods.
Newson, Roger, "Confidence intervals for rank statistics: Somers' D and extensions," The Stata Journal (Sep. 2006) 6(3):309-334.
Nielsen et al., "Sequence-selective recognition of DNA by strand displacement with a thymine-substituted polyamide," Science (1991) 254: 1497-1500.
Noordzij et al. "The prognostic value of CD44 isoforms in prostate cancer patients treated by radical prostatectomy", Clin Cancer Res (May 1997) 3(5): 805-815.
Norman, James, "Thyroid Nodule Ultrasound", Endocrine website (Updated Oct. 13, 2010) http://www.endocrineweb.com/noduleus.html.
Ohl et al., "Gene expression studies in prostate cancer tissue: which reference gene should be selected for normalization?," J. Mol. Med . (2005) 83(12):1014-1024.
Ong et al., "Expression Profiling Identifies a Novel-Methylacyl-CoA Racemase Exon with Fumarate Hydratase Homology," Cancer Research (Jun. 15, 2003) 63:3296-3301.
Oosumi et al., "Mariner transposons in humans", Nature (Dec. 14, 1995) 378 (6558): 672.
Ozen et al., Sep. 24, 2007, Widespread deregulation of microRNA expression in human prostate cancer, Oncogene, 27:1788-1793.
Parker et al., "High expression levels of surviving protein independently predict a poor outcome for patients who undergo surgery for clear cell renal cell carcinoma," Cancer (2006) 107:37-45.
Parker et al., Mar. 10, 2009, Supervised risk predictor of breast cancer based on intrinsic subtypes, Journal of Clinical Oncology, 27(8):1160-1167 with appendix Figure A3.
Pascal et al., "Correlation of mRNA and protein levels: Cell type-specific gene expression of cluster designation antigens in the prostate," BMC Genomics (2008) 9:246 (13 pages).
Patel et al., "Preoperative PSA velocity is an independent prognostic factor for relapse after radical prostatectomy," J Clin Oncol. (2005) 23:6157-6162.
Paulo et al., "Molecular Subtyping of Primary Prostate Cancer Reveals Specific and Shared Target Genes of Different ETS Rearrangements," *Neoplasia* (Jul. 2012) 14(7):600-611.
Penney et al., "mRNA Expression Signature of Gleason Grade Predicts Lethal Prostate Cancer," J Clin Oncol (Jun. 10, 2011) vol. 29, No. 17, pp. 2391-2396 and Appendix.
Pereira et al, "Coagulation factor V and VIIIN ratio as predictors of outcome in paracetamol induced fulminant hepatic failure: relation to other prognostic indicators," Gut (1992) 33:98-102.
Perez et al., "Long, abundantly expressed non-coding transcripts are altered in cancer," Human Molecular Genetics (2008) vol. 17, No. 5, pp. 642-655. Published online Nov. 15, 207.

(56) References Cited

OTHER PUBLICATIONS

Pienta et al. "The current state of preclinical prostate cancer animal models"; Prostate (2008) 69: 629-639.
Pilepich et al., "Phase III radiation therapy oncology group (RTOG) trial 86-10 of androgen deprivation adjuvant to definitive radiotherapy in locally advanced carcinoma of the prostate," Int. J. Radiation Oncology Biol. Phys. (2001) vol. 50, No. 5, pp. 1243-1252.
Pinover et al., "Validation of a treatment policy for patients with prostate specific antigen failure after three-dimensional conformal prostate radiation therapy," Cancer (Feb. 15, 2003) vol. 97, No. 4, pp. 1127-1133.
Pittoni et al., "The Dark Side of Mast Cell-Targeted Therapy in Prostate Cancer," Cancer Res. (2012) 72(4):831-835.
Porkka et al., "RAD21 and KIAA0196 at 8q24 are amplified and overexpressed in prostate cancer," Genes Chromosomes Cancer (2007) 39:1-10.
Porkka et al: Molecular mechanisms of prostate cancer; Eur Urol. (2004) 45(6):683-691.
Pound et al., "Natural history of progression after PSA elevation following radical prostatectomy," JAMA (1999) 281:1591-1597.
Prasad et al., "Identification of genes differentially expressed in benign versus malignant thyroid tumors," Clin Cancer Res. (2008) 14(11):3327-37.
Prat et al. 2012, PAM50 assay and the three-gene model for identifying the major and clinically relevant molecular subtypes of breast cancer. Breast Cancer Res Treat, 135:301-306.
Prensner et al., "Transcriptome Sequencing Identifies PCAT-1, a Novel lincRNA Implicated in Prostate Cancer Progression," (2012) 29 (8): 742-749.
Prensner et al., Dec. 2014, RNA biomarkers associated with metastatic progression in prostate cancer: a multi-institutional high-throughput analysis of SChLAP1, The Lancet/Oncology, 15:1469-1480.
Probe Set Listing for the Affymetrix Human Genome U133 Plus 2.0 array (Accessed from https://www.affymetrix.com/analysis/index.affx on Jul. 1, 2015) (Year: 2015).
Puskas, et al., "Gene profiling identifies genes specific for well-differentiated epithelial thyroid tumors," Cell Mol Biol (Noisy-le-grand) (Sept. 5, 2005) 51(2):177-86.
Rabbits, "Chromosomal translocations in human cancer", Nature (Nov. 10, 1994) 372: 143-149.
Reddy et al., "Clinical utility of microarray-derived genetic signatures in predicting outcomes in prostate cancer," Clinical Genitourinary Cancer (2006) 5(3):187-189.
Reis et al., "Antisense intronic non-coding RNA levels correlate to the degree of tumor differentiation in prostate cancer," Oncogene (2004) 23(39):6684-6692.
Rhodes et al., "Large-scale meta-analysis of cancer microarray data identifies common transcriptional profiles of neoplastic transformation and progression," Proc Nat Acad Sci USA (2004) 101:9309-9314.
Rhodes et al., "Multiplex biomarker approach for determining risk of prostate specific antigen-defined recurrence of prostate cancer," J Nat Cancer Inst. (May 7, 2003) vol. 95, No. 9, pp. 661-668.
Rhodes et al., "Oncomine: A Cancer Microarray Database and Integrated Data-Mining Platform," Neoplasia (2004) 6:1-6.
Rinn et al., "Functional demarcation of active and silent chromatin domains in human HOX loci by noncoding RNAs," Cell (Jun. 29, 2007) 129(7):1311-23.
Roberts et al., "The SWI/SNF complex-chromatin and cancer." Nat Rev Cancer (Feb. 2004) 4(2):133-42.
Robertson et al., "DNA in radical prostatectomy specimens. Prognostic value of tumor ploidy," Acta Oncologica (1991) 30(2):205-207.
Robertson et al., "Reconstructing the ancient mariners of humans." Nat Genet. (Apr. 1996) 12(4):360-1.
Robinson et al., "A dynamic programming approach for the alignment of signal peaks in multiple gas chromatography-mass spectrometry experiments," BMC Bioinformatics (2007) 8.1:419.
Robinson, et al., "A comparison of Affymetrix gene expression arrays," BMC Bioinformatics (Nov. 15, 2007) 8:449.
Romanuik et al., "LNCaP Atlas: Gene expression associated with in vivo progression to castration-recurrent prostate cancer," GMB Medical Genomics (2010) 3:43, pp. 1-19.
Ross et al., "Tissue-based Genomics Augments Post-prostatectomy Risk Stratification in a Natural History Cohort of Intermediate- and High-Risk Men," European Urology 69 (2016) pp. 157-165.
Rotblat et al., "A Possible Role for Long Non-Coding RNA in Modulating Signaling Pathways," Med. Hvnotheses (2011) 77:962-965, Elsevier.
Rotunno et al., "A Gene Expression Signature from Peripheral Whole Blood for Stage I Lung Adenocarcinoma," Cancer Prevention Research (Jul. 8, 2011) 4(10) 1599-1607.
Rowley, "A new Consistent Chromosomal Abnormality in Chronic Myelogenous Leukaemia Identified by Quinacrine fluorescence and Giemsa Staining," Nature (Jun. 1, 1973) 243:290-293.
Rowley, "Chromosome translocations: dangerous liaisons revisited," Nature Reviews: Cancer (Dec. 2001) 1):245-250.
Rubin et al., "Molecular genetics of human prostate cancer," Modern Pathol. (2004) 17(3):380-388.
Saito-Hisaminato et al., "Genome-Wide Profiling of Gene Expression in 29 Normal Human Tissues with a cDNA Microarray," DNA Research (2002) vol. 9, pp. 35-45.
Saligan et al., "Supervised Classification by Filter Methods and Recursive Feature Elimination Predicts Rick of Radiotherapy-Related Fatigue in Patients with Prostate Cancer," Cancer Informatics (2014) 13: 141-152.
Sandler et al., "Overall survival after prostate-specific-antigen-detected recurrence following conformal radiation therapy," Int J Rad Oncol Biol Phys. (2000) 48:629-633.
Sanghvi, "Heterocyclic base modifications in nucleic acids and their applications in antisense oligonucleotides in Antisense Research and Applications," Crooke, S. T. and Lebleu, B., ed., CRC Press. (1993) Ch 15 274-285.
Saramaki et al., "Amplification of EIF3S3 gene is associated with advanced stage in prostate cancer," Am J Pathol. (2001) 159:2089-2094.
Sato et al., "Clinical significance of alterations of chromosome 8 in high-grade, advanced, nonmetastatic prostate carcinoma," J Natl Cancer Inst. (1999) 91:1574-1580.
Savinainen et al., "Expression and copy number analysis of TRPS 1, EIF3S3 and MYC genes in breast and prostate cancer," Br J Cancer (2004) 90: 1041-1046.
Savinainen et al., "Over expression of EIF3S3 promotes cancer cell growth," The Prostate (2006) 66: 1144-1150.
Schlomm et al., "Molecular staging of prostate cancer in the year 2007," World .J. Urol. (Mar. 2007) 25(1):19-30.
Schmidt et al., "Lack of interferon consensus sequence binding protein (ICSBP) transcripts in human myeloid leukemias," Blood (1998) 91:22-29.
Schumacher et al., "A Common 8q24 Variant in Prostate and Breast Cancer from a Large Nested Case-Control Study," Cancer Res. (2007) 67:2951-2956.
Seiler et al., Oct. 2017, Impact of molecular subtypes in muscle-invasive bladder cancer on predicting response and survival after neoadjuvant chemotherapy, European Urology, 72(4):544-554.
Setlur et al., 2008, Estrogen-dependent signaling in a molecularly distinct subclass of aggressive prostate cancer, Journal of the National Cancer Institute, 100:815-813.
Severi et al., "The Common Variant rs1447295 on Chromosome 8q24 and Prostate Cancer Risk: Results from an Australian Population-based Case-Control Study", Cancer Epidemiology, Biomarkers & Prevention (2007) 16:610-611.
Shariat et al., "An updated catalog of prostate cancer predictive tools," Cancer (2008) 113(11):3062-6.
Shariat et al., "Surviving expression is associated with features of biologically aggressive prostate carcinoma," Cancer (2004) 100(4): 751-757.
Shen et al., "The SWI/SNF ATPase Brm is a gatekeeper of proliferative control in prostate cancer," Cancer Res. (Dec. 15, 2008) 68(24):10154-62.

(56) References Cited

OTHER PUBLICATIONS

Shibru et al., "Does the 3-gene diagnostic assay accurately distinguish benign from malignant thyroid neoplasms?" Cancer (Sep. 1, 2008) 113(5):930-5. doi: 10.1002/cncr.23703.
Shipley et al., "Radiation therapy for clinically localized prostate cancer: a multi-institutional pooled analysis," JAMA (1999) 281:1598-1604.
Simmons et al., "Natural history of biochemical recurrence after radical prostatectomy: risk assessment for secondary therapy," Eur Urol. (May 2007) 51(5):1175-84.
Singh et al., "Gene expression correlates of clinical prostate cancer behavior," Cancer Cell (Mar. 2002) vol. 1, pp. 1203-1209.
Singh et al., "LNA (locked nucleic acids): synthesis and high-affinity nucleic acid recognition," Chem Commun (1998) 4:455-456.
Singh et al., "Synthesis of 2'-amino-LNA: A novel conformationally restricted high-affinity oligonucleotide analogues with a handle," J Org Chem (1998) 63:10035-10039.
Sinnott et al., 2016, Prognostic utility of a new mRNA expression signature of Gleason score, Clinical Cancer Research 23(1):81-87.
Slotkin et al., "Transposable elements and the epigenetic regulation of the genome." Nat Rev Genet. (Apr. 2007) 8(4):272-85.
Smit et al., "High-Resolution ERG-Expression Profiling on GeneChip Exon 1.0 ST Arrays in Primary and Castration-Resistant Prostate Cancer," *BJU International* (2013), 111(5):836-842, BJU International.
Solo et al., "Prevalence of prostate cancer (PC) clinical states (CS) in the United States: Estimates using a dynamic progression model," ASCO Annual Meeting, Journal of Clinical Oncology (May 20, 2011) vol. 29, No. 15, Abstract 4637.
Sparano et al., 2015, Prospective Validation of a 21-Gene Expression Assay in Breast Cancer New Eng. J. Med. 373:20 2005-2014.
Srikantan et al., "PCGEM1, a prostate-specific gene, is overexpressed in prostate cancer," PNAS (Oct. 24, 2000) 97(22): 12216-12221.
Stamey et al., "Molecular genetic profiling of Gleason grade 415 prostate cancers compared to benign prostatic hyperplasia," J Urol. (2001) 166(6):2171-2177.
Stanbrough et al., "Increased Expression of Genes Converting Adrenal Androgens to Testosterone in Androgen-Independent Prostate Cancer," Cancer Res (Mar. 1, 2006) 66(5):2815-2825.
Stavenhagen et al., "An ancient provirus has imposed androgen regulation on the adjacent mouse sex-limited protein Jene." Cell (Oct. 21, 1988) 55(2):247-54.
Stephenson et al., "Integration of gene expression profiling and clinical variables to predict prostate carcinoma recurrence after radical prostatectomy," Cancer (Jul. 15, 2005) 104(2):290-298.
Stephenson et al., "Postoperative Nomogram Predicting the 10-Year Probability of Prostate Cancer Recurrence After Radical Prostatectomy," J Clin Oncol (2008) vol. 23 (28), pp. 7005-7012.
Subramanian et al., "Gene set enrichment analysis: A knowledge-based approach for interpreting genome-wide expression profiles," PNAS USA (2005) 102:15545-15550.
Sun et al., "Aberrant expression of SWI/SNF catalytic subunits BRG1/BRM is associated with tumor development and increased invasiveness in prostate cancers," Prostate (Feb. 1, 2007) 67(2):203-13.
Taft et al., "Non-coding RNAs: regulators of disease," J Pathol. (Jan. 2010) 220(2):126-39.
Takayama et al., "TACC2 Is an Androgen-Responsive Cell Cycle Regulator Promoting Androgen-Mediated and Castration-Resistant Growth of Prostate Cancer," Mol Endocrinol (May 2012) 26(5):748-761.
Talantov et al., "Gene Based Prediction of Clinically Localized Prostate Cancer Progression After Radical Prostatectomy," The Journal of Urology (Oct. 2010) vol. 184, 1521-1528.
Taylor et al., "Integrative genomic profiling of human prostate cancer," Cancer Cell (Jul. 13, 2010) vol. 18 (1), pp. 11-22.
Thompson et al., "Adjuvant and Salvage Radiotherapy After Prostatectomy: AUA/ASTRO Guideline," J Urol. (2013) 190(2):441-449.
Thompson et al., "Is the GPSM scoring algorithm for patients with prostate cancer valid in the contemporary era?" J Urol. (Aug. 2007) vol. 178 (2), 459-463.
Thorsen et al., "Alternative Splicing in Colon, Bladder, and Prostate Cancer Identified by Exon Array Analysis," Molecular & Cellular Proteomics (Mar. 18, 2008) vol. 7, No. 7, pp. 1214-1224.
Tockman et al., "Considerations in bringing a cancer biomarker to clinical application," Cancer Research (1992) 52:2711-2718.
Tollefson et al., "Stratification of Patient Risk Based on Prostate-Specific Antigen Doubling Time After Radical Retropubic Prostatectomy," Mayo Clin Proc. (2007) 82:422-427.
Tomlins et al., "Distinct classes of chromosomal rearrangements create oncogenic ETS gene fusions in prostate cancer," Nature (Aug. 2, 2007) 448(7153):595-9.
Tomlins et al., "Integrative molecular concept modeling of prostate cancer progression," Nat Genet. (2007) 39:41-51.
Tomlins et al., "Recurrent Fusion of TMPRSS2 and ETS Transcription Factor Genes in Prostate Cancer," Science (2005) 310(5748):644-648.
Tomlins et al., "TMPRSS2:ETV4 Gene Fusions Define a Third Molecular Subtype of Prostate Cancer," Cancer Res. (2006) 66:3396-3400.
Tricoli et al., "Detection of prostate cancer and predicting progression: current and future diagnostic markers," Clinical Cancer Research (Jun. 15, 2004) 10:3943-3953.
True et al., "A molecular correlate to the Gleason grading system for prostate adenocarcinoma," PNAS (Jul. 18, 2006) vol. 103, No. 29, pp. 10991-10996.
Tsuchiya et al., "Clinical significance in situ hybridization analysis in pathologic of alterations of chromosome 8 detected by fluorescence organ-confined prostate cancer," Genes Chromosomes Cancer (2002) 34:363-371.
Tsuchiya et al., "Mapping and gene expression profile of the minimally overrepresented 8q24 region in prostate cancer," Am J Pathol. (May 2002) 160(5):1799-1806.
Vainio, 2011, High-throughput screening for novel prostate cancer drug targets, dissertation, Turun Yliopisot, University of Turku, Finland, 74 pp.
Vanaja et al., "PDLIM4 Repression by Hypermethylation as a Potential Biomarker for Prostate Cancer," Clin. Cancer Res. (2006) 12(4):1128-1136.
Vanaja et al., "Transcriptional Silencing of Zinc Finger Protein 185 Identified Profiling Is Associated with Prostate Cancer Progression," Cancer Research (Jul. 15, 2003) 63:3877-3882.
Varambally et al., "Integrative Genomic and Proteomic Analysis of Prostate Cancer Reveals Signatures of Metastatic Progression," Cancer Cell (Nov. 2005) 8(5):393-406.
Varela et al., "Exome sequencing identifies frequent mutation of the SWI/SNF complex gene PBRM1 in renal carcinoma," Nature (Jan. 27, 2011) 469(7331):539-42.
Varricchi et al., "Are Mast Cells MASTers in Cancer?" Front Immunol. ePub (Apr. 12, 2017) 8:424.
Versteege et al., "Truncating mutations of hSNF5/INI1 in aggressive paediatric cancer." Nature (Jul. 9, 1998) 394 6689):203-6.
Vickers et al., "Extensions to decision curve analysis, a novel method for evaluating diagnostic tests, prediction models and molecular markers," BMC Medical Informatics and Decision Making, (2008) 8(53):1-17.
Visakorpi, "The molecular genetics of prostate cancer," Urology (2003) 62(5 Suppl 1):3-10.
Wang et al., "RNA-Seq: a revolutionary tool for transcriptomics," Nature Reviews/Genetics (Jan. 2009) vol. 10, pp. 57-63.
Wang et al., "Two common chromosome 8q24 variants are associated with increased risk for prostate cancer," Cancer Res. (2007) 67:2944-2950.
Warrick et al., 2016, FOXA1, GATA3 and PPARγ cooperate to drive luminal subtype in bladder cancer: a molecular analysis of established human cell lines, Scientific Reports, 6:38531, DOI: 10.1038, 15 pp.
Watson et al., "Future opportunities for the diagnosis and treatment of prostate cancer," Prostate Cancer Prostatic Dis. (2004) 7:S8-S13.
Weber et al., "The prognostic value of expression of HIF1[alpha], EGFR and VEGF-A, in localized prostate cancer for intermediate-

(56) References Cited

OTHER PUBLICATIONS and high-risk patients treated with radiation therapy with or without androgen deprivation therapy," Radiation Oncology (Apr. 30, 2012) vol. 7, No. 66, 8 pages.
Welsh et al., "Analysis of Gene Expression Identifies Candidate Markers and Pharmacological Targets in Prostate Cancer," Cancer Res. (Aug. 15, 2001) 61:5974-5978.
Wiegand et al., "ARID1A mutations in endometriosis-associated ovarian carcinomas," N Engl J Med. (Oct. 14, 2010) 363 (16):1532-43.
Willman et al., "Immunohistochemical staining for DNA topoisomerase II-alpha in benign, premalignant, and malignant lesions of the prostate," Prostate (Mar. 1, 2000) 42(4):280-286.
Winkler et al.: "Stage D1 prostatic adenocarcinoma: significance of nuclear DNA ploidy patterns studied by flow cytometry," Mayo Clin Proc. (1988) 63(2): 103-112.
Wyatt et al., "Heterogeneity in the inter-tumor transcriptome of high risk prostate cancer," *Genome Biology* (Aug. 26, 2014) vol. 15, No. 8, pp. 2-14.
Xiong et al., Dec. 2017, Low CCL17 expression associated with unfavorable postoperative prognosis of patients with clear cell renal cll carcinoma, BMC Cancer, 17(1):117.
Yap et al., "Molecular interplay of the noncoding RNA ANRIL and methylated histone H3 lysine 27 by polycomb CBX7 n transcriptional silencing of INK4a," Mol Cell. (Jun. 11, 2010) 38(5):662-74.
Yates et al., "X:Map: annotation and visualization of genome structure for Affymetrix exon array analysis," Nucleic Acids Res. (2008) vol. 36:D780-D786.
Yeager et al., "Genome-wide association study of prostate cancer identifies a second risk locus at 8q24," Nat Genet (2007) 39:645-649.
Yegnasubramanian et al., "DNA hypomethylation arises later in prostate cancer progression than CpG island hypermethylation and contributes to metastatic tumor heterogeneity," Cancer Res. (Nov. 1, 2008) 68(21): pp. 8954-8967.
Yeliin et al., "Widespread occurrence of antisense transcription in the human genome," Nat Biotechnol. (2003) 21(4):379-86.
You et al., Jun. 14, 2016, Integrated classification of prostate cancer reveals a novel luminal subtype with poor outcome, Cancer Research 76(17):4948-4958.
Yu et al., "An integrated network of androgen receptor, polycomb, and TMPRSS2-ERG gene fusions in prostate cancer progression," Cancer Cell. (May 18, 2010) 17(5):443-54.
Yu et al., "Gene expression alterations in prostate cancer predicting tumor aggression and preceding development of malignancy," J Clin Oncol. (Jul. 15, 2004) 22(14):2790-2799.
Yukinawa et al., "A multi-class predictor based on a probabilistic model: application to gene expression profiling-based diagnosis of thyroid tumors," BMC Genomics (Jul. 27, 2006) 7:190.
Zanetta et al., "Flow-cytometric analysis of deoxyribonucleic acid content in advanced ovarian carcinoma: its importance in long-term survival," Am J Obstet Gynecol (1996) 175(5): 1217-1225.
Zelefsky et al., "High dose radiation delivered by intensity modulated conformal radiotherapy improves the outcome of localized prostate cancer," The Journal of Urology (Sep. 2001) 166(3):876-881.
Zelefsky et al., "Neoadjuvant hormonal therapy improves the therapeutic ratio in patients with bulky prostatic cancer treated with three-dimensional conformal radiation therapy," Int J Radiat Oncol Biol Phys. (1994) 29:755-761.
Zhang et al. Apr. 2019, 21-Gene Recurrence Score Assay Could Not Predict Benefit of Post-mastectomy Radiotherapy in T1-2 N1mic ER-Pos ve HER2 Negative Breast Cancer, Frontiers in Oncology, 9(270): 8 pp.
Zhang et al., Sep. 18, 2014, Proteogenomic characterization of human colon and rectal cancer, Nature, 513(7518):382-387.
Zhao et al., "Development and validation of a 24-gene predictor of response to postoperative radiotherapy in prostate cancer: a matched, retrospective analysis," Lancet Oncol (2016) 17, pp. 1612-1620.
GenBank Accession No. AA462934 dated Jun. 10, 1997, 2 pages.
GenBank Accession No. AA920095 dated Apr. 20, 1998, 2 pages.
GenBank Accession No. AB028840 dated Jan. 12, 2000, 2 pages.
GenBank Accession No. AB030836 dated Oct. 23, 1999, 2 pages.
GenBank Accession No. AB036741 dated Dec. 22, 2000, 3 pages.
GenBank Accession No. AF077349 dated Dec. 14, 2000, 2 pages.
GenBank Accession No. AF077351 dated Dec. 20, 2000, 3 pages.
GenBank Accession No. AF115517 dated Nov. 23, 2005, 4 pages.
GenBank Accession No. AI413910 dated Feb. 9, 1999, 2 pages.
GenBank Accession No. AI414999 dated Feb. 9, 1999, 2 pages.
GenBank Accession No. AI425960 dated Mar. 9, 1999, 2 pages.
GenBank Accession No. AI851940 dated Jul. 15, 1999, 2 pages.
GenBank Accession No. AK018022 dated Sep. 19, 2008, 4 pages.
GenBank Accession No. AK019341 dated Sep. 19, 2008, 3 pages.
GenBank Accession No. AK019342 dated Sep. 19, 2008, 3 pages.
GenBank Accession No. AK034387 dated Sep. 19, 2008, 4 pages.
GenBank Accession No. AK038229 dated Sep. 19, 2008, 4 pages.
GenBank Accession No. AK038434 dated Sep. 19, 2008, 4 pages.
GenBank Accession No. AK041534 dated Sep. 19, 2008, 4 pages.
GenBank Accession No. AK042683 dated Sep. 19, 2008, 4 pages.
GenBank Accession No. AK136096 dated Sep. 19, 2008, 4 pages.
GenBank Accession No. AK136101 dated Sep. 19, 2008, 4 pages.
GenBank Accession No. AK142768 dated Sep. 19, 2008, 3 pages.
GenBank Accession No. AL591433 dated Jan. 15, 2009, 56 pages.
GenBank Accession No. BC004702 dated Jul. 15, 2006, 3 pages.
GenBank Accession No. BC055737 dated Jul. 15, 2006, 2 pages.
GenBank Accession No. BC086799 dated Sep. 21, 2006, 3 pages.
GenBank Accession No. BF449664 dated Dec. 1, 2000, 1 page.
GenBank Accession No. BG063957 dated Jan. 26, 2001, 2 pages.
GenBank Accession No. BG077309 dated Dec. 17, 2003, 2 pages.
GenBank Accession No. BM114282 dated Jan. 30, 2002, 2 pages.
GenBank Accession No. BY023910 dated Dec. 6, 2002, 2 pages.
GenBank Accession No. CN724527 dated May 18, 2004, 2 pages.
GenBank Accession No. NM_000130 dated Oct. 18, 2009, 6 pages.
GenBank Accession No. NM_000493 dated Mar. 15, 2009, 4 pages.
GenBank Accession No. NM_000598, GI No. 62243067, dated Jun. 6, 2010, 5 pages.
GenBank Accession No. NM_000688, GI No. 40316942, dated Apr. 11, 2010, 5 pages.
GenBank Accession No. NM_001013398; GI No. 62243247, dated Jun. 6, 2010, 5 pages.
GenBank Accession No. NM_001034 dated Oct. 5, 2009, 5 pages.
GenBank Accession No. NM_001039573, GI No. 221316683, dated Mar. 4, 2010, 5 pages.
GenBank Accession No. NM_001049 dated Jun. 21, 2009, 4 pages.
GenBank Accession No. NM_001067 dated Oct. 18, 2009, 5 pages.
GenBank Accession No. NM_001098533, GI No. 237858579, dated May 7, 2010, 5 pages.
GenBank Accession No. NM_001130851; GI No. 195927024, dated Mar. 5, 2010, 4 pages.
GenBank Accession No. NM_001136154 dated Jan. 8, 2012, 6 pages.
GenBank Accession No. NM_001136155 dated Jan. 8, 2012, 6 pages.
GenBank Accession No. NM_001143998, GI No. 221316675, dated Mar. 4, 2010, 5 pages.
GenBank Accession No. NM_001143999, GI No. 221316679, dated Mar. 5, 2010, 5 pages.
GenBank Accession No. NM_001144001, GI No. 221316686, dated Mar. 4, 2010, 5 pages.
GenBank Accession No. NM_001160367, GI No. 237858581, dated May 7, 2010, 5 pages.
GenBank Accession No. NM_001786 dated Nov. 1, 2009, 4 pages.
GenBank Accession No. NM_001844 dated Sep. 28, 2009, 7 pages.
GenBank Accession No. NM_003003, GI No. 221316681, dated Mar. 4, 2010, 5 pages.
GenBank Accession No. NM_003014; GI No. 170784837, dated Mar. 13, 2010, 5 pages.
GenBank Accession No. NM_003184; GI No. 115527086, dated Mar. 4, 2010, 7 pages.
GenBank Accession No. NM_003873.3 dated Oct. 18, 2009, 4 pages.
GenBank Accession No. NM_004336; GI No. 211938448, dated Mar. 14, 2010, 6 pages.

(56) References Cited

OTHER PUBLICATIONS

GenBank Accession No. NM_004449 dated Jan. 8, 2012, 6 pages.
GenBank Accession No. NM_005025.2 dated Jul. 12, 2009, 4 pages.
GenBank Accession No. NM_005192, GI No. 195927023, dated Mar. 4, 2010, 4 pages.
GenBank Accession No. NM_005651.1 datedOct. 27, 2009, 3 pages.
GenBank Accession No. NM_006265, GI No. 208879448, dated Apr. 11, 2010, 6 pages.
GenBank Accession No. NM_006558 dated 812109, 3 pages.
GenBank Accession No. NM_006727 dated Oct. 18, 2009, 3 pages.
GenBank Accession No. NM_006819; GI No. 110225356, dated 517/2010, 5 pages.
GenBank Accession No. NM_012152; GI No. 183396778, dated Apr. 5, 2010, 5 pages.
GenBank Accession No. NM_014846; GI No. 120952850, dated Mar. 4, 2010, 6 pages.
GenBank Accession No. NM_016623; GI No. 42734437, dated Mar. 29, 2009, 4 pages.
GenBank Accession No. NM_018930 dated Feb. 10, 2008, _ pages.
GenBank Accession No. NM_031966 GI No. 34304372, dated Jun. 6, 2010, 5 pages.
GenBank Accession No. NM_032334; GI No. 223468686, dated Mar. 5, 2010, 3 pages.
GenBank Accession No. NM_052987, GI No. 237858574, dated May 17, 2010, 5 pages.
GenBank Accession No. NM_052988, GI No. 237858573, dated May 17, 2010, 5 pages.
GenBank Accession No. NM_080546; GI No. 112363101, dated May 17, 2010, 6 pages.
GenBank Accession No. NM_080607 dated Sep. 3, 2009, 2 pages.
GenBank Accession No. NM_133445 dated Sep. 20, 2009, 5 pages.
GenBank Accession No. NM_138455; GI No. 34147546, dated May 7, 2010, 3 pages.
GenBank Accession No. NM_182918 dated Jan. 8, 2012, 6 pages.
GenBank Accession No. NM_199166, GI No. 40316938, dated Apr. 11, 2010, 5 pages.
GenBank Accession No. NP_001058 dated Dec. 25, 2011, 9 pages.
GenBank Accession No. W34764 dated May 13, 1996, 2 pages.
Supplemental Table 1 of U.S. Appl. No. 61/057,698, filed May 30, 2008, 13 pages.
Supplemental Table 2 of U.S. Appl. No. 61/057,698, filed May 30, 2008, 15 pages.
Supplemental Table 3 of U.S. Appl. No. 61/057,698, filed May 30, 2008, 21 pages.
Supplemental Table 4 of U.S. Appl. No. 61/057,698, filed May 30, 12008, 1 page.
Supplemental Table 5 of U.S. Appl. No. 61/057,698, filed May 30, 12008, 2 pages.
Supplemental Table 6 of U.S. Appl. No. 61/057,698, filed May 30, 2008, 1 page.
Australian 2nd Office Action dated Feb. 18, 2019 for Application No. AU 2013302365—GENDX.007AU.
Australian Office Action of AU Appl. No. 2015242941, dated May 18, 2017, 4 pages.
Australian Examination Report issued on Oct. 4, 2016, regarding AU 2014274499.
Australian Notice of Acceptance dated Jul. 11, 2018 for AU 2012352153.
Canadian Office Action dated Sep. 25, 2018 for CA 2,858,581 (GENDX.006CA).
Canadian Office Action dated Mar. 17, 2017 for CA 2,725,978. GENDX.005C1.
European Search Report dated Nov. 3, 2011, regarding EP 09753364 6 pages.
Supplementary European Search Report issued on Aug. 31, 2015 regarding EP 12 85 7492.
Extended European Search Report dated Apr. 4, 2016 for European Patent Application No. 13 829 137.
Extended European Search Report dated Apr. 22, 2016 for European Patent Application No. 13838743.6.
Supplementary Partial European Search Report issued on Feb. 1, 2017, regarding EP 14 77 4066.6.
EP Search Report for EP 18 155 318.1 mailed Apr. 24, 2018.
IEP Examination dated Jun. 19, 2018 for EP 18 838 743.6.
EP Search Report for EP 18 155 318.0 mailed Aug. 24, 2018??
EP Extended Search Report dated Nov. 23, 2018 for EP 18 179 289.6.
International Written Opinion of the International Searching Authority for PCT/CA2010/000621, mailed Aug. 11, 2010.
International Search Report of PCT application No. PCT/US2011/061204, mailed Jun. 19, 2012, 11 pages.
International Search Report/Written Opinion in PCT/US2007 /079423 mailed Feb. 27, 2008, 12 pages.
International Preliminary Report on Patentability for PCT/US2011I/043703, 4 pages, issued Jan. 22, 2013.
International Preliminary Report on Patentability in PCT/US2007 /079423 mailed Apr. 9, 2009, 6 pages.
International Preliminary Report on Patentability in PCT/US2007/83504 mailed May 5, 2009, 4 pages.
International Search Report and Written Opinion dated Nov. 18, 2013 for International PCT Patent Application No. PCT/CA2013/050686.
International Search Report and Written Opinion dated Dec. 21, 2018 for PCT/US18/45058—GENDX.016WO –.
International Search Report and Written Opinion for PCT/US20111/043703, 5 pages, issued Mar. 27, 2012.
International Search Report and Written Opinion of PCT/CA2018/050563 mailed Aug. 13, 2018.
International Search Report dated Mar. 13, 2014 for PCT/US2013/055429.
International Search Report dated Oct. 14, 2009, regarding PCTICA2009/000694, 5 pages.
International Search Report for PCT/CA2010/000266, mailed Jul. 12, 2010.
International Search Report for PCT/CA2010/000621, completed Jul. 14, 2010.
International Search Report/Written Opinion in PCT/US2007/079423 mailed Feb. 27, 2008, 10 pages.
International Search Report/Written Opinion in PCT/US2007/83504 mailed Apr. 14, 2008, 3 pages.
Invitation—dated Oct. 15, 2018—PCT/US18/45058—GENDX.016WO.
Invitation to Pay Additional Fees dated Oct. 15, 2018 for PCT/US18/45058.
Office Action for U.S. Appl. No. 14/772,348, GENDX.011NP Dec. 13, 2018.
Office action from U.S. Appl. No. 12/474,879, dated Jan. 6, 2012, 15 pages.
U.S. Final O.A. Dec. 11, 2018—5/156,936 GENDX.008P1C1.
U.S. Final O.A. Dec. 31, 2018—U.S. Appl. No. 15/064,266 GENDX.008C1.
Final Office Action from U.S. Appl. No. 12/442,685, dated Oct. 13, 2011, 8 pages.
Sequence Alignment Search for Seq ID No. 457. Jan. 28, 2014. 2 pages.
Sequence Alignment Search for Seq ID No. 1904. Jan. 28, 2014. 1 page.

* cited by examiner

SYSTEMS AND METHODS FOR PREPROCESSING TARGET DATA AND GENERATING PREDICTIONS USING A MACHINE LEARNING MODEL

CROSS-REFERENCE TO RELATED APPLICATIONS

This application is a division of U.S. patent application Ser. No. 17/346,106, filed Jun. 11, 2021, which is a division of U.S. patent application Ser. No. 13/968,838, filed Aug. 16, 2013, which claims the benefit of priority of U.S. Provisional Application No. 61/684,066, filed Aug. 16, 2012, U.S. Provisional Application No. 61/764,365, filed Feb. 13, 2013, and U.S. Provisional Application No. 61/783,124, filed Mar. 14, 2013. The content of the foregoing applications is incorporated herein in its entirety by reference.

SUMMARY

In some embodiments, a machine learning model may be accessed and used to generate a likelihood score related to a condition. In some embodiments, pre-computed vectors for preprocessing target data may be derived from a training dataset (e.g., used to build the machine learning model), and the pre-computed vectors may be used to generate processed data from target data derived from a target sample. The machine learning model may then be used on the processed data to generate the likelihood score related to the condition. As an example, subsets of the training dataset may be randomly selected, and the pre-computed vectors may be derived from the randomly-selected subsets of the training dataset. The pre-computed vectors may be applied to the target data to generate the processed data. In one use case, for example, the target data may be normalized using the pre-computed vectors.

In some embodiments, features of the machine learning model may be determined and configured for the machine learning model based on the training dataset (e.g., statistical significance of each feature with respect to a predicted condition and control data, variable importance of each feature, etc.). In some embodiments, the statistical significance of the differential expression observed between a first group associated with the predicted condition and a control group may be assessed for each feature. As an example, features with a p-value greater than 0.05 may be removed. In some embodiments, a random forest variable importance may be determined and used to remove features. As an example, features with mean decrease gini (or MDG) less than or equal to 0 may be discarded, and features with MDG greater than 6.5e-3 and mean decrease in accuracy (or MDA) greater than 0 may be selected for the machine learning model, where MDA is the average difference in accuracy of the true variable compared with the variable randomized for trees in the forest, and MDG is the mean of the change in gini between a parent node and a child node when splitting on a variable across the whole forest.

In some embodiments, each feature of the features of the machine learning model has a non-zero co-efficient greater than a predetermined threshold in multiple bootstrapping processes performed on different subsets of the training dataset. In some embodiments, the machine learning model may include a random forest having decision trees, and the features may be selected for the random forest based on the features having a non-zero co-efficient greater than a p-value threshold in multiple bootstrapping processes performed on different subsets of the training dataset.

DETAILED DESCRIPTION

Figure 1:
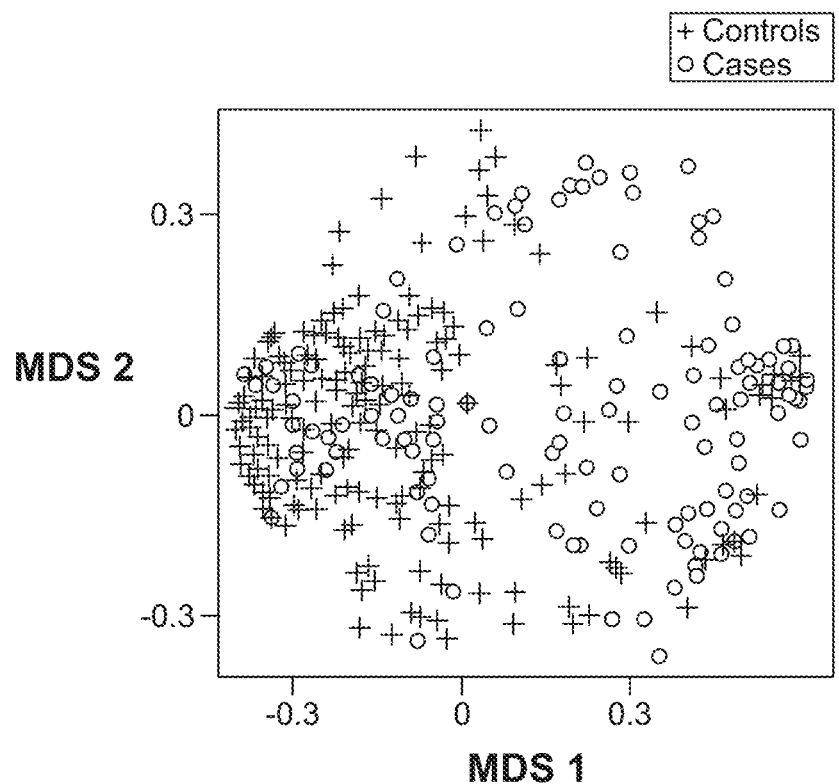
FIGS. 1 and 2 show a multidimensional scaling plot of (1) training and (2) testing sets (validation sets), respectively, where controls are indicated as '+' and cases are indicated as circles.

Unless defined otherwise or the context clearly dictates otherwise, all technical and scientific terms used herein have the same meaning as commonly understood by one of ordinary skill in the art to which this invention belongs. In describing the present invention, the following terms may be employed, and are intended to be defined as indicated below.

As used herein, "having" is an open-ended phrase like "comprising" and "including," and includes circumstances where additional elements are included and circumstances where they are not.

As used herein, "optional" or "optionally" means that the subsequently described event or circumstance may or may not occur, and that the description includes instances where the event or circumstance occurs and instances in which it does not.

As used herein, the term "about" refers to approximately a +/−10% variation from a given value. It is to be understood that such a variation is always included in any given value provided herein, whether or not it is specifically referred to.

Use of the singular forms "a," "an," and "the" include plural references unless the context clearly dictates otherwise. Thus, for example, reference to "a polynucleotide" includes a plurality of polynucleotides, reference to "a target" includes a plurality of such targets, reference to "a normalization method" includes a plurality of such methods, and the like. Additionally, use of specific plural references, such as "two," "three," etc., read on larger numbers of the same subject, unless the context clearly dictates otherwise.

Terms such as "connected," "attached," "linked" and "conjugated" are used interchangeably herein and encompass direct as well as indirect connection, attachment, linkage or conjugation unless the context clearly dictates otherwise.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values, which are about the same quantity or amount as the recited value, are also within the scope of the invention, as are ranges based thereon. Where a combination is disclosed, each sub-combination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

In some embodiments, a machine learning model may be accessed and used to generate a likelihood score related to a condition. In some embodiments, pre-computed vectors for preprocessing target data may be derived from a training dataset used to build the machine learning model, and the pre-computed vectors may be used to generate processed data from target data derived from a target sample. The machine learning model may then be used on the processed data to generate the likelihood score related to the condition. As an example, subsets of the training dataset may be randomly selected, and the pre-computed vectors may be derived from the randomly-selected subsets of the training dataset. The pre-computed vectors may be applied to the target data to generate the processed data. In one use case, for example, the target data may be normalized using the pre-computed vectors.

In some embodiments, features of the machine learning model may be determined and configured for the machine learning model based on the training dataset (e.g., statistical significance of each feature with respect to a predicted condition and control data, variable importance of each feature, etc.). In some embodiments, the statistical significance of the differential expression observed between a first group associated with the predicted condition and a control group may be assessed for each feature. As an example, features with a p-value greater than 0.05 may be removed. In some embodiments, a random forest variable importance may be determined and used to remove features. As an example, features with mean decrease gini (or MDG) less than or equal to 0 may be discarded, and features with MDG greater than 6.5e-3 and mean decrease in accuracy (or MDA) greater than 0 may be selected for the machine learning model, where MDA is the average difference in accuracy of the true variable compared with the variable randomized for trees in the forest, and MDG is the mean of the change in gini between a parent node and a child node when splitting on a variable across the whole forest.

Figure 2:
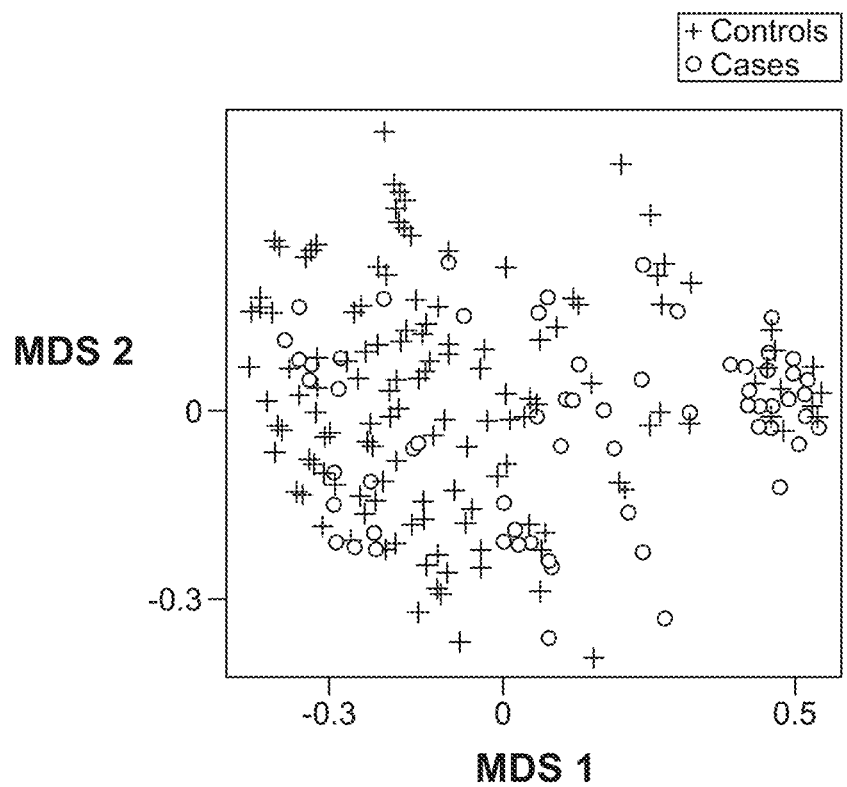

In some embodiments, the training dataset may include both data for controls (e.g., individuals without a given condition) and cases (e.g., individuals with the condition). As an example, FIGS. 1 and 2 show a multidimensional scaling plot of (1) training and (2) testing/validation sets, respectively, where controls are indicated as '+' and cases are indicated as circles. In both the training and validation sets, the controls tend to cluster on the left of the plot and the cases on the right of the plot. In this manner, most of the biological differences are expressed in the first dimension of the scaling. In one scenario, random forest proximity was used to measure the 22-marker distance between samples (e.g., see examples herein with respect to 22-marker use cases).

Although some embodiments describe the use of a machine learning model that include a random forest, it should be noted that, in other embodiments, the machine learning model may additionally or alternatively include use of one or more other machine learning algorithms. Such other machine learning algorithms may include one or more supervised learning algorithms, unsupervised learning algorithms, reinforcement learning algorithms, or other algorithms.

Examples of supervised learning algorithms may include Average One-Dependence Estimators (AODE), Artificial neural network (e.g., Backpropagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

Examples of unsupervised learning algorithms may include artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering. Examples of reinforcement learning algorithms include temporal difference learning, Q-learning and Learning Automata. Alternatively, the machine learning algorithm may comprise Data Pre-processing.

It should be noted that additional and alternative embodiments and examples are described in U.S. Pat. No. 11,035,005, filed Aug. 16, 2013, which is incorporated herein by reference in its entirety.

Coding and Non-Coding Targets

The methods disclosed herein often comprise assaying the expression level of a plurality of targets. The plurality of targets may comprise coding targets and/or non-coding targets of a protein-coding gene or a non-protein-coding gene. A protein-coding gene structure may comprise an exon and an intron. The exon may further comprise a coding sequence (CDS) and an untranslated region (UTR). The protein-coding gene may be transcribed to produce a pre-mRNA and the pre-mRNA may be processed to produce a mature mRNA. The mature mRNA may be translated to produce a protein.

A non-protein-coding gene structure may comprise an exon and intron. Usually, the exon region of a non-protein-coding gene primarily contains a UTR. The non-proteincoding gene may be transcribed to produce a pre-mRNA and the pre-mRNA may be processed to produce a non-coding RNA (ncRNA).

A coding target may comprise a coding sequence of an exon. A non-coding target may comprise a UTR sequence of an exon, intron sequence, intergenic sequence, promoter sequence, non-coding transcript, CDS antisense, intronic antisense, UTR antisense, or non-coding transcript antisense. A non-coding transcript may comprise a non-coding RNA (ncRNA). In some instances, the plurality of targets may be differentially expressed. In some instances, a plurality of probe selection regions (PSRs) is differentially expressed.

Probes/Primers

The present invention provides for a probe set for diagnosing, monitoring and/or predicting a status or outcome of a cancer in a subject comprising a plurality of probes, wherein (i) the probes in the set are capable of detecting an expression level of at least one non-coding target; and (ii) the expression level determines the cancer status of the subject with at least about 40% specificity.

The probe set may comprise one or more polynucleotide probes. Individual polynucleotide probes comprise a nucleotide sequence derived from the nucleotide sequence of the target sequences or complementary sequences thereof. The nucleotide sequence of the polynucleotide probe is designed such that it corresponds to, or is complementary to the target sequences. The polynucleotide probe can specifically hybridize under either stringent or lowered stringency hybridization conditions to a region of the target sequences, to the complement thereof, or to a nucleic acid sequence (such as a cDNA) derived therefrom.

The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the invention, the polynucleotide probe is complementary to a region of a target mRNA derived from a target sequence in the probe set. Computer programs can also be employed to select probe sequences that may not cross hybridize or may not hybridize non-specifically.

In some instances, microarray hybridization of RNA, extracted from prostate cancer tissue samples and amplified, may yield a dataset that is then summarized and normalized by the fRMA technique. The 5,362,207 raw expression probes are summarized and normalized into 1,411,399 probe selection regions ("PSRs"). After removal (or filtration) of cross-hybridizing PSRs, highly variable PSRs (variance above the 90th percentile), and PSRs containing more than 4 probes, approximately 1.1 million PSRs remain. Following fRMA and filtration, the data can be decomposed into its principal components and an analysis of variance model is used to determine the extent to which a batch effect remains present in the first 10 principal components.

These remaining 1.1 million PSRs can then be subjected to filtration by a T-test between CR (clinical recurrence) and non-CR samples. Using a p-value cut-off of 0.01, 18,902 features remained in analysis for further selection. Feature selection was performed by regularized logistic regression using the elastic-net penalty. The regularized regression was bootstrapped over 1000 times using all training data; with each iteration of bootstrapping features that have non-zero co-efficient following 3-fold cross validation were tabulated. In some instances, features that were selected in at least 25% of the total runs were used for model building.

One skilled in the art understands that the nucleotide sequence of the polynucleotide probe need not be identical to its target sequence in order to specifically hybridize thereto. Methods of determining sequence identity are known in the art and can be determined, for example, by using the BLASTN program of the University of Wisconsin Computer Group (GCG) software or provided on the NCBI website. The nucleotide sequence of the polynucleotide probes of the present invention may exhibit variability by differing (e.g. by nucleotide substitution, including transition or transversion) at one, two, three, four or more nucleotides from the sequence of the coding target or non-coding target.

Other criteria known in the art may be employed in the design of the polynucleotide probes of the present invention. For example, the probes can be designed to have <50% G content and/or between about 25% and about 70% G+C content. Strategies to optimize probe hybridization to the target nucleic acid sequence can also be included in the process of probe selection.

Hybridization under particular pH, salt, and temperature conditions can be optimized by taking into account melting temperatures and by using empirical rules that correlate with desired hybridization behaviors. Computer models may be used for predicting the intensity and concentration-dependence of probe hybridization.

The system of the present invention further provides for primers and primer pairs capable of amplifying target sequences defined by the probe set, or fragments or subsequences or complements thereof. The nucleotide sequences of the probe set may be provided in computer-readable media for in silico applications and as a basis for the design of appropriate primers for amplification of one or more target sequences of the probe set.

A label can optionally be attached to or incorporated into a probe or primer polynucleotide to allow detection and/or quantitation of a target polynucleotide representing the target sequence of interest. The target polynucleotide may be the expressed target sequence RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different targets may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the invention described herein include any substance which can be detected when bound to or incorporated into the biomolecule of interest. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a polynucleotide may comprise a biotin-binding species, and an optically detectable label may be conjugated to biotin and then bound to the labeled polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Coding schemes may optionally be used, comprising encoded particles and/or encoded tags associated with different polynucleotides of the invention. A variety of different coding schemes are known in the art, including fluorophores, including SCNCs, deposited metals, and RF tags.

Polynucleotides from the described target sequences may be employed as probes for detecting target sequences expression, for ligation amplification schemes, or may be used as primers for amplification schemes of all or a portion of a target sequences. When amplified, either strand produced by amplification may be provided in purified and/or isolated form.

The polynucleotides may be provided in a variety of formats, including as solids, in solution, or in an array. The polynucleotides may optionally comprise one or more labels, which may be chemically and/or enzymatically incorporated into the polynucleotide.

In one embodiment, solutions comprising polynucleotide and a solvent are also provided. In some embodiments, the solvent may be water or may be predominantly aqueous. In some embodiments, the solution may comprise at least two, three, four, five, six, seven, eight, nine, ten, twelve, fifteen, seventeen, twenty or more different polynucleotides, including primers and primer pairs, of the invention. Additional substances may be included in the solution, alone or in combination, including one or more labels, additional solvents, buffers, biomolecules, polynucleotides, and one or more enzymes useful for performing methods described herein, including polymerases and ligases. The solution may further comprise a primer or primer pair capable of amplifying a polynucleotide of the invention present in the solution.

In some embodiments, one or more polynucleotides provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, SiO2, SiN4, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica-based substrates (e.g. glass, quartz, or the like), or crystalline substrates used in, e.g., the semiconductor and microprocessor industries, such as silicon, gallium arsenide, indium doped GaN and the like, and include semiconductor nanocrystals.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

Diagnostic Samples

Diagnostic samples for use with the systems and in the methods of the present invention comprise nucleic acids suitable for providing RNAs expression information. In principle, the biological sample from which the expressed RNA is obtained and analyzed for target sequence expression can be any material suspected of comprising cancer tissue or cells. The diagnostic sample can be a biological sample used directly in a method of the invention. Alternatively, the diagnostic sample can be a sample prepared from a biological sample.

In one embodiment, the sample or portion of the sample comprising or suspected of comprising cancer tissue or cells can be any source of biological material, including cells, tissue or fluid, including bodily fluids. Non-limiting examples of the source of the sample include an aspirate, a needle biopsy, a cytology pellet, a bulk tissue preparation or a section thereof obtained for example by surgery or autopsy, lymph fluid, blood, plasma, serum, tumors, and organs. In some embodiments, the sample is from urine. Alternatively, the sample is from blood, plasma or serum. In some embodiments, the sample is from saliva.

The samples may be archival samples, having a known and documented medical outcome, or may be samples from current patients whose ultimate medical outcome is not yet known.

In some embodiments, the sample may be dissected prior to molecular analysis. The sample may be prepared via macrodissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Helv solution, osmic acid solution and Carnoy solution.

Crosslinking fixatives can comprise any agent suitable for forming two or more covalent bonds, for example an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion; see methods.

One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek® V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFMFM, Cryo-Gel™, and OCT Compound (Electron Microscopy Sciences, Hatfield, Pa.). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

RNA Extraction

RNA can be extracted and purified from biological samples using any suitable technique. A number of techniques are known in the art, and several are commercially available (e.g., FormaPure nucleic acid extraction kit, Agencourt Biosciences, Beverly Mass., High Pure FFPE RNA Micro Kit, Roche Applied Science, Indianapolis, Ind.). RNA can be extracted from frozen tissue sections using TRIzol (Invitrogen, Carlsbad, Calif.) and purified using RNeasy Protect kit (Qiagen, Valencia, Calif.). RNA can be further purified using DNAse I treatment (Ambion, Austin, Tex.) to eliminate any contaminating DNA. RNA concentrations can be made using a Nanodrop ND-1000 spectrophotometer (Nanodrop Technologies, Rockland, Del.). RNA can be further purified to eliminate contaminants that interfere with cDNA synthesis by cold sodium acetate precipitation. RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

Kits

Kits for performing the desired method(s) are also provided, and comprise a container or housing for holding the components of the kit, one or more vessels containing one or more nucleic acid(s), and optionally one or more vessels containing one or more reagents. The reagents include those described in the composition of matter section above, and those reagents useful for performing the methods described, including amplification reagents, and may include one or more probes, primers or primer pairs, enzymes (including polymerases and ligases), intercalating dyes, labeled probes, and labels that can be incorporated into amplification products.

In some embodiments, the kit comprises primers or primer pairs specific for those subsets and combinations of target sequences described herein. At least two, three, four or five primers or pairs of primers suitable for selectively amplifying the same number of target sequence-specific polynucleotides can be provided in kit form. In some embodiments, the kit comprises from five to fifty primers or pairs of primers suitable for amplifying the same number of target sequence-representative polynucleotides of interest.

The reagents may independently be in liquid or solid form. The reagents may be provided in mixtures. Control samples and/or nucleic acids may optionally be provided in the kit. Control samples may include tissue and/or nucleic acids obtained from or representative of tumor samples from patients showing no evidence of disease, as well as tissue and/or nucleic acids obtained from or representative of tumor samples from patients that develop systemic cancer.

The nucleic acids may be provided in an array format, and thus an array or microarray may be included in the kit. The kit optionally may be certified by a government agency for use in prognosing the disease outcome of cancer patients and/or for designating a treatment modality.

Instructions for using the kit to perform one or more methods of the invention can be provided with the container, and can be provided in any fixed medium. The instructions may be located inside or outside the container or housing, and/or may be printed on the interior or exterior of any surface thereof. A kit may be in multiplex form for concurrently detecting and/or quantitating one or more different target polynucleotides representing the expressed target sequences.

Devices

Devices useful for performing methods of the invention are also provided. The devices can comprise means for characterizing the expression level of a target sequence of the invention, for example components for performing one or more methods of nucleic acid extraction, amplification, and/or detection. Such components may include one or more of an amplification chamber (for example a thermal cycler), a plate reader, a spectrophotometer, capillary electrophoresis apparatus, a chip reader, and or robotic sample handling components. These components ultimately can obtain data that reflects the expression level of the target sequences used in the assay being employed.

The devices may include an excitation and/or a detection means. Any instrument that provides a wavelength that can excite a species of interest and is shorter than the emission wavelength(s) to be detected can be used for excitation. Commercially available devices can provide suitable excitation wavelengths as well as suitable detection component.

Exemplary excitation sources include a broadband UV light source such as a deuterium lamp with an appropriate filter, the output of a white light source such as a xenon lamp or a deuterium lamp after passing through a monochromator to extract out the desired wavelength(s), a continuous wave (cw) gas laser, a solid-state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of a label used in an assay.

The devices typically comprise a means for identifying a given sample, and of linking the results obtained to that sample. Such means can include manual labels, barcodes, and other indicators which can be linked to a sample vessel, and/or may optionally be included in the sample itself, for example where an encoded particle is added to the sample. The results may be linked to the sample, for example in a computer memory that contains a sample designation and a record of expression levels obtained from the sample. Linkage of the results to the sample can also include a linkage to a particular sample receptacle in the device, which is also linked to the sample identity.

In some instances, the devices also comprise a means for correlating the expression levels of the target sequences being studied with a prognosis of disease outcome. In some instances, such means comprises one or more of a variety of correlative techniques, including lookup tables, algorithms, multivariate models, and linear or nonlinear combinations of expression models or algorithms. The expression levels may be converted to one or more likelihood scores, reflecting likelihood that the patient providing the sample may exhibit a particular disease outcome. The models and/or algorithms can be provided in machine readable format and can optionally further designate a treatment modality for a patient or class of patients.

The device also comprises output means for outputting the disease status, prognosis and/or a treatment modality. Such output means can take any form which transmits the results to a patient and/or a healthcare provider, and may include a monitor, a printed format, or both. The device may use a computer system for performing one or more of the steps provided.

In some embodiments, the method, systems, and kits disclosed herein further comprise the transmission of data/information. For example, data/information derived from the detection and/or quantification of the target may be transmitted to another device and/or instrument. In some instances, the information obtained from an algorithm is transmitted to another device and/or instrument. Transmission of the data/information may comprise the transfer of data/information from a first source to a second source. The first and second sources may be in the same approximate location (e.g., within the same room, building, block, campus). Alternatively, first and second sources may be in multiple locations (e.g., multiple cities, states, countries, continents, etc).

In some instances, transmission of the data/information comprises digital transmission or analog transmission. Digital transmission may comprise the physical transfer of data (a digital bit stream) over a point-to-point or point-to-multipoint communication channel. Examples of such channels are copper wires, optical fibers, wireless communication channels, and storage media. In some embodiments, the data is represented as an electromagnetic signal, such as an electrical voltage, radiowave, microwave, or infrared signal.

Analog transmission may comprise the transfer of a continuously varying analog signal. The messages can either be represented by a sequence of pulses by means of a line code (baseband transmission), or by a limited set of continuously varying wave forms (passband transmission), using a digital modulation method. The passband modulation and corresponding demodulation (also known as detection) can be carried out by modem equipment. According to the most common definition of digital signal, both baseband and passband signals representing bit-streams are considered as digital transmission, while an alternative definition only considers the baseband signal as digital, and passband transmission of digital data as a form of digital-to-analog conversion.

Amplification and Hybridization

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification and other reactions. mRNA can first be treated with reverse transcriptase and a primer to create cDNA prior to detection, quantitation and/or amplification; this can be done in vitro with purified mRNA or in situ, e.g., in cells or tissues affixed to a slide.

By "amplification" is meant any process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse translation and then optionally from further amplification reactions. The amplification product may include all or a portion of a target sequence, and may optionally be labeled. A variety of amplification methods are suitable for use, including polymerase-based methods and ligation-based methods. Exemplary amplification techniques include the polymerase chain reaction method (PCR), the lipase chain reaction (LCR), ribozyme-based methods, self-sustained sequence replication (3SR), nucleic acid sequence-based amplification (NASBA), the use of Q Beta replicase, reverse transcription, nick translation, and the like.

Asymmetric amplification reactions may be used to preferentially amplify one strand representing the target sequence that is used for detection as the target polynucleotide. In some cases, the presence and/or amount of the amplification product itself may be used to determine the expression level of a given target sequence. In other instances, the amplification product may be used to hybridize to an array or other substrate comprising sensor polynucleotides which are used to detect and/or quantitate target sequence expression.

The first cycle of amplification in polymerase-based methods typically forms a primer extension product complementary to the template strand. If the template is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that can produce an amplifiable segment; thus, each primer must hybridize so that its 3'-nucleotide is paired to a nucleotide in its complementary template strand that is located 3'-from the 3'-nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase or enzyme activity. The enzyme can be thermolabile or thermostable. Mixtures of enzymes can also be used.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

Detection and/or Quantification of Target Sequences

Any method of detecting and/or quantitating the expression of the encoded target sequences can in principle be used in the invention. The expressed target sequences can be directly detected and/or quantitated, or may be copied and/or amplified to allow detection of amplified copies of the expressed target sequences or its complement.

In some instances, target sequences may be detected by sequencing. Sequencing methods may comprise whole genome sequencing or exome sequencing. Sequencing methods such as Maxim-Gilbert, chain-termination, or high-throughput systems may also be used. Additional, suitable sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, and SOLiD sequencing.

Classification Arrays

The present invention contemplates that a probe set or probes derived therefrom may be provided in an array format. In the context of the present invention, an "array" is a spatially or logically organized collection of polynucleotide probes. An array comprising probes specific for a coding target, non-coding target, or a combination thereof may be used. Expression of these sequences may be detected alone or in combination with other transcripts. In some embodiments, an array is used which comprises a wide range of sensor probes for prostate-specific expression products, along with appropriate control sequences. In some instances, the array may comprise the Human Exon 1.0 ST Array (HuEx 1.0 ST, Affymetrix, Inc., Santa Clara, Calif.).

Typically the polynucleotide probes are attached to a solid substrate and are ordered so that the location (on the substrate) and the identity of each are known. The polynucleotide probes can be attached to one of a variety of solid substrates capable of withstanding the reagents and conditions necessary for use of the array. Examples include, but are not limited to, polymers, such as (poly)tetrafluoroethylene, (poly)vinylidenedifluoride, polystyrene, polycarbonate, polypropylene and polystyrene; ceramic; silicon; silicon dioxide; modified silicon; (fused) silica, quartz or glass; functionalized glass; paper, such as filter paper, diazotized cellulose; nitrocellulose filter; nylon membrane; and polyacrylamide gel pad. Substrates that are transparent to light are useful for arrays that may be used in an assay that involves optical detection.

Examples of array formats include membrane or filter arrays (for example, nitrocellulose, nylon arrays), plate arrays (for example, multiwell, such as a 24-, 96-, 256-, 384-, 864- or 1536-well, microtitre plate arrays), pin arrays, and bead arrays (for example, in a liquid "slurry"). Arrays on substrates such as glass or ceramic slides are often referred to as chip arrays or "chips." Such arrays are well known in the art. In one embodiment of the present invention, the Cancer Prognosticarray is a chip.

Data Analysis

In some embodiments, one or more pattern recognition methods can be used in analyzing the expression level of target sequences. The pattern recognition method can comprise a linear combination of expression levels, or a nonlinear combination of expression levels. In some embodiments, expression measurements for RNA transcripts or combinations of RNA transcript levels are formulated into linear or non-linear models or algorithms (e.g., an 'expression signature') and converted into a likelihood score. This likelihood score indicates the probability that a biological sample is from a patient who may exhibit no evidence of disease, who may exhibit systemic cancer, or who may exhibit biochemical recurrence. The likelihood score can be used to distinguish these disease states. The models and/or algorithms can be provided in machine readable format, and may be used to correlate expression levels or an expression profile with a disease state, and/or to designate a treatment modality for a patient or class of patients.

Assaying the expression level for a plurality of targets may comprise the use of an algorithm or classifier. Array data can be managed, classified, and analyzed using techniques known in the art. Assaying the expression level for a plurality of targets may comprise probe set modeling and data pre-processing. Probe set modeling and data pre-processing can be derived using the Robust Multi-Array (RMA) algorithm or variants GC-RMA, fRMA, Probe Logarithmic Intensity Error (PLIER) algorithm or variant iterPLIER. Variance or intensity filters can be applied to pre-process data using the RMA algorithm, for example by removing target sequences with a standard deviation of <10 or a mean intensity of <100 intensity units of a normalized data range, respectively.

Alternatively, assaying the expression level for a plurality of targets may comprise the use of a machine learning algorithm. The machine learning algorithm may comprise a supervised learning algorithm. Examples of supervised learning algorithms may include Average One-Dependence Estimators (AODE), Artificial neural network (e.g., Backpropagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

The machine learning algorithms may also comprise an unsupervised learning algorithm. Examples of unsupervised learning algorithms may include artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering.

In some instances, the machine learning algorithms comprise a reinforcement learning algorithm. Examples of reinforcement learning algorithms include, but are not limited to, temporal difference learning, Q-learning and Learning Automata. Alternatively, the machine learning algorithm may comprise Data Pre-processing.

Preferably, the machine learning algorithms may include, but are not limited to, Average One-Dependence Estimators (AODE), Fisher's linear discriminant, Logistic regression, Perceptron, Multilayer Perceptron, Artificial Neural Networks, Support vector machines, Quadratic classifiers, Boosting, Decision trees, C4.5, Bayesian networks, Hidden Markov models, High-Dimensional Discriminant Analysis, and Gaussian Mixture Models. The machine learning algorithm may comprise support vector machines, Naïve Bayes classifier, k-nearest neighbor, high-dimensional discriminant analysis, or Gaussian mixture models. In some instances, the machine learning algorithm comprises Random Forests.

Additional Techniques and Tests

Factors known in the art for diagnosing and/or suggesting, selecting, designating, recommending or otherwise determining a course of treatment for a patient or class of patients suspected of having cancer can be employed in combination with measurements of the target sequence expression. The methods disclosed herein may include additional techniques such as cytology, histology, ultrasound analysis, MRI results, CT scan results, and measurements of PSA levels.

Certified tests for classifying disease status and/or designating treatment modalities may also be used in diagnosing, predicting, and/or monitoring the status or outcome of a cancer in a subject. A certified test may comprise a means for characterizing the expression levels of one or more of the target sequences of interest, and a certification from a government regulatory agency endorsing use of the test for classifying the disease status of a biological sample.

In some embodiments, the certified test may comprise reagents for amplification reactions used to detect and/or quantitate expression of the target sequences to be characterized in the test. An array of probe nucleic acids can be used, with or without prior target amplification, for use in measuring target sequence expression.

The test is submitted to an agency having authority to certify the test for use in distinguishing disease status and/or outcome. Results of detection of expression levels of the target sequences used in the test and correlation with disease status and/or outcome are submitted to the agency. A certification authorizing the diagnostic and/or prognostic use of the test is obtained.

In some embodiments, portfolios are established such that the combination of genes in the portfolio exhibit improved sensitivity and specificity relative to known methods. In considering a group of genes for inclusion in a portfolio, a small standard deviation in expression measurements correlates with greater specificity. Other measurements of variation such as correlation coefficients can also be used in this capacity.

In some instances, the methods disclosed herein may comprise the use of a genomic classifier (GC) model. A general method for developing a GC model may comprise (a) providing a sample from a subject suffering from a cancer; (b) assaying the expression level for a plurality of targets; (c) generating a model by using a machine learning algorithm. In some instances, the machine learning algorithm comprises Random Forests. In another example, a GC model may developed by using a machine learning algorithm to analyze and rank genomic features. Analyzing the genomic features may comprise classifying one or more genomic features. The method may further comprise validating the classifier and/or refining the classifier by using a machine learning algorithm.

The methods disclosed herein may comprise generating one or more clinical classifiers (CC). The clinical classifier can be developed using one or more clinicopathologic variables. The clinicopathologic variables may be selected from the group comprising Lymph node invasion status (LNI); Surgical Margin Status (SMS); Seminal Vesicle Invasion (SVI); Extra Capsular Extension (ECE); Pathological Gleason Score; and the pre-operative PSA. The method may comprise using one or more of the clinicopathologic variables as binary variables. Alternatively, or additionally, the one or more clinicopathologic variables may be converted to a logarithmic value (e.g., log 10). The method may further comprise assembling the variables in a logistic regression. In some instances, the CC is combined with the GC to produce a genomic clinical classifier (GCC).

In some instances, the methods disclosed herein may comprise the use of a genomic-clinical classifier (GCC) model. A general method for developing a GCC model may comprise (a) providing a sample from a subject suffering from a cancer; (b) assaying the expression level for a plurality of targets; (c) generating a model by using a machine learning algorithm. In some instances, the machine learning algorithm comprises Random Forests.

Cancer

The systems, compositions and methods disclosed herein may be used to diagnosis, monitor and/or predict the status or outcome of a cancer. Generally, a cancer is characterized by the uncontrolled growth of abnormal cells anywhere in a body. The abnormal cells may be termed cancer cells, malignant cells, or tumor cells. Many cancers and the abnormal cells that compose the cancer tissue are further identified by the name of the tissue that the abnormal cells originated from (for example, breast cancer, lung cancer, colon cancer, prostate cancer, pancreatic cancer, thyroid cancer). Cancer is not confined to humans; animals and other living organisms can get cancer.

In some instances, the cancer may be malignant. Alternatively, the cancer may be benign. The cancer may be a recurrent and/or refractory cancer. Most cancers can be classified as a carcinoma, sarcoma, leukemia, lymphoma, myeloma, or a central nervous system cancer.

The cancer may be a sarcoma. Sarcomas are cancers of the bone, cartilage, fat, muscle, blood vessels, or other connective or supportive tissue. Sarcomas include, but are not limited to, bone cancer, fibrosancoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosancoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Alternatively, the cancer may be a carcinoma. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penic cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis. Preferably, the cancer is a prostate cancer. Alternatively, the cancer may be a thyroid cancer, bladder cancer, or pancreatic cancer.

In some instances, the cancer is a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The cancer may be a leukemia. The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic-leukemia.

In some instances, the cancer is a lymphoma. Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Cancer Staging

Diagnosing, predicting, or monitoring a status or outcome of a cancer may comprise determining the stage of the cancer. Generally, the stage of a cancer is a description (usually numbers I to IV with IV having more progression) of the extent the cancer has spread. The stage often takes into account the size of a tumor, how deeply it has penetrated, whether it has invaded adjacent organs, how many lymph nodes it has metastasized to (if any), and whether it has spread to distant organs. Staging of cancer can be used as a predictor of survival, and cancer treatment may be determined by staging. Determining the stage of the cancer may occur before, during, or after treatment. The stage of the cancer may also be determined at the time of diagnosis.

Cancer staging can be divided into a clinical stage and a pathologic stage. Cancer staging may comprise the TNM classification. Generally, the TNM Classification of Malignant Tumours (TNM) is a cancer staging system that describes the extent of cancer in a patient's body. T may describe the size of the tumor and whether it has invaded nearby tissue, N may describe regional lymph nodes that are involved, and M may describe distant metastasis (spread of cancer from one body part to another). In the TNM (Tumor, Node, Metastasis) system, clinical stage and pathologic stage are denoted by a small "c" or "p" before the stage (e.g., cT3N1MO or pT2N0).

Often, clinical stage and pathologic stage may differ. Clinical stage may be based on all of the available information obtained before a surgery to remove the tumor. Thus, it may include information about the tumor obtained by physical examination, radiologic examination, and endoscopy. Pathologic stage can add additional information gained by examination of the tumor microscopically by a pathologist. Pathologic staging can allow direct examination of the tumor and its spread, contrasted with clinical staging which may be limited by the fact that the information is obtained by making indirect observations at a tumor which is still in the body. The TNM staging system can be used for most forms of cancer.

Alternatively, staging may comprise Ann Arbor staging. Generally, Ann Arbor staging is the staging system for lymphomas, both in Hodgkin's lymphoma (previously called Hodgkin's disease) and Non-Hodgkin lymphoma (abbreviated NHL). The stage may depend on both the place where the malignant tissue is located (as located with biopsy, CT scanning and increasingly positron emission tomography) and on systemic symptoms due to the lymphoma ("B symptoms": night sweats, weight loss of >10% or fevers). The principal stage may be determined by location of the tumor. Stage I may indicate that the cancer is located in a single region, usually one lymph node and the surrounding area. Stage I often may not have outward symptoms. Stage II can indicate that the cancer is located in two separate regions, an affected lymph node or organ and a second affected area, and that both affected areas are confined to one side of the diaphragm—that is, both are above the diaphragm, or both are below the diaphragm. Stage III often indicates that the cancer has spread to both sides of the diaphragm, including one organ or area near the lymph nodes or the spleen. Stage IV may indicate diffuse or disseminated involvement of one or more extralymphatic organs, including any involvement of the liver, bone marrow, or nodular involvement of the lungs.

Modifiers may also be appended to some stages. For example, the letters A, B, E, X, or S can be appended to some stages. Generally, A or B may indicate the absence of constitutional (B-type) symptoms is denoted by adding an "A" to the stage; the presence is denoted by adding a "B" to the stage. E can be used if the disease is "extranodal" (not in the lymph nodes) or has spread from lymph nodes to adjacent tissue. X is often used if the largest deposit is >10 cm large ("bulky disease"), or whether the mediastinum is wider than ⅓ of the chest on a chest X-ray. S may be used if the disease has spread to the spleen.

The nature of the staging may be expressed with CS or PS. CS may denote that the clinical stage as obtained by doctor's examinations and tests. PS may denote that the pathological stage as obtained by exploratory laparotomy (surgery performed through an abdominal incision) with splenectomy (surgical removal of the spleen).

Therapeutic Regimens

Diagnosing, predicting, or monitoring a status or outcome of a cancer may comprise treating a cancer or preventing a cancer progression. In addition, diagnosing, predicting, or monitoring a status or outcome of a cancer may comprise identifying or predicting responders to an anti-cancer therapy. In some instances, diagnosing, predicting, or monitoring may comprise determining a therapeutic regimen. Determining a therapeutic regimen may comprise administering an anti-cancer therapy. Alternatively, determining a therapeutic regimen may comprise modifying, recommending, continuing or discontinuing an anti-cancer regimen. In some instances, if the sample expression patterns are consistent with the expression pattern for a known disease or disease outcome, the expression patterns can be used to designate one or more treatment modalities (e.g., therapeutic regimens, anti-cancer regimen). An anti-cancer regimen may comprise one or more anti-cancer therapies. Examples of anti-cancer therapies include surgery, chemotherapy, radiation therapy, immunotherapy/biological therapy, photodynamic therapy.

For patients with high test scores consistent with systemic disease outcome after prostatectomy, additional treatment modalities such as adjuvant chemotherapy (e.g., docetaxel, mitoxantrone and prednisone), systemic radiation therapy (e.g., samarium or strontium) and/or anti-androgen therapy (e.g., surgical castration, finasteride, dutasteride) can be designated. Such patients would likely be treated immediately with anti-androgen therapy alone or in combination with radiation therapy in order to eliminate presumed micrometastatic disease, which cannot be detected clinically but can be revealed by the target sequence expression signature.

Such patients can also be more closely monitored for signs of disease progression. For patients with intermediate test scores consistent with biochemical recurrence only (BCR-only or elevated PSA that does not rapidly become manifested as systemic disease only localized adjuvant therapy (e.g., radiation therapy of the prostate bed) or short course of anti-androgen therapy would likely be administered. For patients with low scores or scores consistent with no evidence of disease (NED) adjuvant therapy would not likely be recommended by their physicians in order to avoid treatment-related side effects such as metabolic syndrome (e.g., hypertension, diabetes and/or weight gain), osteoporosis, proctitis, incontinence or impotence. Patients with samples consistent with NED could be designated for watchful waiting, or for no treatment. Patients with test scores that do not correlate with systemic disease but who have successive PSA increases could be designated for watchful waiting, increased monitoring, or lower dose or shorter duration anti-androgen therapy.

Target sequences can be grouped so that information obtained about the set of target sequences in the group can be used to make or assist in making a clinically relevant judgment such as a diagnosis, prognosis, or treatment choice.

A patient report is also provided comprising a representation of measured expression levels of a plurality of target sequences in a biological sample from the patient. In some embodiments, the representation of the measured expression level(s) may take the form of a linear or nonlinear combination of expression levels of the target sequences of interest. The patient report may be provided in a machine (e.g., a computer) readable format and/or in a hard (paper) copy. The report can also include standard measurements of expression levels of said plurality of target sequences from one or more sets of patients with known disease status and/or outcome. The report can be used to inform the patient and/or treating physician of the expression levels of the expressed target sequences, the likely medical diagnosis and/or implications, and optionally may recommend a treatment modality for the patient.

Also provided are representations of the gene expression profiles useful for treating, diagnosing, prognosticating, and otherwise assessing disease. In some embodiments, these profile representations are reduced to a medium that can be automatically read by a machine such as computer readable media (magnetic, optical, and the like). The articles can also include instructions for assessing the gene expression profiles in such media. For example, the articles may comprise a readable storage form having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms can assist in the visualization of such data.

Exemplary Embodiments

Disclosed herein, in some embodiments, is a method for diagnosing, predicting, and/or monitoring a status or outcome of a cancer a subject, comprising: (a) assaying an expression level of a plurality of targets in a sample from the subject; and (b) for diagnosing, predicting, and/or monitoring a status or outcome of a cancer based on the expression levels of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a thyroid cancer. In some embodiments, the cancer is a bladder cancer. In some embodiments, the cancer is a lung cancer. In some embodiments, the method further comprises assaying an expression level of a coding target.

In some embodiments, the coding target is an exon-coding transcript. In some embodiments, the exon-coding transcript is an exonic sequence. In some embodiments, the method further comprises assaying an expression level of a non-coding target. In some instances, the non-coding target is a non-coding transcript. In other instances, the non-coding target is an intronic sequence. In other instances, the non-coding target is an intergenic sequence. In some instances, the non-coding target is a UTR sequence. In other instances, the non-coding target is a non-coding RNA transcript. In some embodiments, the target comprises a nucleic acid sequence. In some embodiments, the nucleic acid sequence is a DNA sequence. In some embodiments, the nucleic acid sequence is an RNA sequence. In other instances, the target comprises a polypeptide sequence.

In some embodiments, assaying the expression level comprises detecting and/or quantifying a nucleotide sequence of the plurality of targets. Alternatively, assaying the expression level comprises detecting and/or quantifying a polypeptide sequence of the plurality of targets. In some embodiments, assaying the expression level comprises detecting and/or quantifying the DNA levels of the plurality of targets. In some embodiments, assaying the expression level comprises detecting and/or quantifying the RNA or mRNA levels of the plurality of targets. In some embodiments, assaying the expression level comprises detecting and/or quantifying the protein level of the plurality of targets. In some embodiments, the diagnosing, predicting, and/or monitoring the status or outcome of a cancer comprises determining the malignancy of the cancer. In some embodiments, the diagnosing, predicting, and/or monitoring the status or outcome of a cancer includes determining the stage of the cancer. In some embodiments, the diagnosing, predicting, and/or monitoring the status or outcome of a cancer includes assessing the risk of cancer recurrence. In some embodiments, diagnosing, predicting, and/or monitoring the status or outcome of a cancer may comprise determining the efficacy of treatment. In some embodiments, diagnosing, predicting, and/or monitoring the status or outcome of a cancer may comprise determining a therapeutic regimen. Determining a therapeutic regimen may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen.

In some embodiments, assaying the expression level comprises detecting and/or quantifying a nucleotide sequence of the plurality of targets. In some embodiments, determining the treatment for the cancer includes determining the efficacy of treatment. Determining the treatment for the cancer may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen.

The methods use the probe sets, probes and primers described herein to provide expression signatures or profiles from a test sample derived from a subject having or suspected of having cancer. In some embodiments, such methods involve contacting a test sample with a probe set comprising a plurality of probes under conditions that permit hybridization of the probe(s) to any target nucleic acid(s) present in the test sample and then detecting any probe: target duplexes formed as an indication of the presence of the target nucleic acid in the sample. Expression patterns thus determined are then compared to one or more reference profiles or signatures. Optionally, the expression pattern can be normalized. The methods use the probe sets, probes and primers described herein to provide expression signatures or profiles from a test sample derived from a subject to classify the cancer as recurrent or non-recurrent.

In some embodiments, such methods involve the specific amplification of target sequences nucleic acid(s) present in the test sample using methods known in the art to generate an expression profile or signature which is then compared to a reference profile or signature.

In some embodiments, the invention further provides for prognosing patient outcome, predicting likelihood of recurrence after prostatectomy and/or for designating treatment modalities.

In one embodiment, the methods generate expression profiles or signatures detailing the expression of the target sequences having altered relative expression with different cancer outcomes.

In some embodiments, the methods detect combinations of expression levels of sequences exhibiting positive and negative correlation with a disease status. In one embodiment, the methods detect a minimal expression signature.

The gene expression profiles of each of the target sequences comprising the portfolio can fixed in a medium such as a computer readable medium. This can take a number of forms. For example, a table can be established into which the range of signals (e.g., intensity measurements) indicative of disease or outcome is input. Actual patient data can then be compared to the values in the table to determine the patient samples diagnosis or prognosis. In a more sophisticated embodiment, patterns of the expression signals (e.g., fluorescent intensity) are recorded digitally or graphically.

The expression profiles of the samples can be compared to a control portfolio. The expression profiles can be used to diagnose, predict, or monitor a status or outcome of a cancer. For example, diagnosing, predicting, or monitoring a status or outcome of a cancer may comprise diagnosing or detecting a cancer, cancer metastasis, or stage of a cancer. In other instances, diagnosing, predicting, or monitoring a status or outcome of a cancer may comprise predicting the risk of cancer recurrence. Alternatively, diagnosing, predicting, or monitoring a status or outcome of a cancer may comprise predicting mortality or morbidity.

In some embodiments, assaying the expression level comprises detecting and/or quantifying a nucleotide sequence of the plurality of targets. In some instances, the method may further comprise diagnosing a cancer in the subject. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a bladder cancer. In some embodiments, the cancer is a thyroid cancer. In some embodiments, the cancer is a lung cancer. In some instances, characterizing the subject comprises determining whether the subject would respond to an anti-cancer therapy. Alternatively, characterizing the subject comprises identifying the subject as a non-responder to an anti-cancer therapy. Optionally, characterizing the subject comprises identifying the subject as a responder to an anti-cancer therapy.

Further disclosed herein are methods for selecting a subject suffering from a cancer for enrollment into a clinical trial. Generally, the method comprises: (a) providing a sample from a subject; (b) assaying the expression level for a plurality of targets in the sample; and (c) characterizing the subject based on the expression level of the plurality of targets. In some embodiments, the method further comprises assaying an expression level of a coding target. In some instances, the non-coding target is a non-coding transcript. In other instances, the non-coding target is an intronic sequence. In other instances, the non-coding target is an intergenic sequence. In some instances, the non-coding target is a UTR sequence. In other instances, the non-coding target is a non-coding RNA transcript. In some embodiments, the target comprises a nucleic acid sequence. In some embodiments, the nucleic acid sequence is a DNA sequence. In some embodiments, the nucleic acid sequence is an RNA sequence.

Also disclosed herein is a method of diagnosing cancer in an individual in need thereof, comprising (a) obtaining an expression profile from a sample obtained from the individual; (b) comparing the expression profile from the sample to an expression profile of a control or standard; and (c) diagnosing a cancer in the individual if the expression profile of the sample (i) deviates from the control or standard from a healthy individual or population of healthy individuals, or (ii) matches the control or standard from an individual or population of individuals who have or have had the cancer. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the method further comprises a software module executed by a computer-processing device to compare the expression profiles. In some embodiments, the deviation is the expression level of one or more targets from the sample is at least about 30% greater than the expression level of one or more targets from a control or standard derived from a healthy individual or population of healthy individuals. In some embodiments, the deviation is the expression level of one or more targets from the sample is less than the expression level of one or more targets from a control or standard derived from a healthy individual or population of healthy individuals. In some embodiments, the deviation is the expression level of one or more targets from the sample is at least about 30% less than the expression level of one or more targets from a control or standard derived from a healthy individual or population of healthy individuals. In some embodiments, the method further comprises using a machine to isolate the target or the probe from the sample. In some embodiments, the method further comprises contacting the sample with a label that specifically binds to the target, the probe, or a combination thereof. In some embodiments, the method further comprises amplifying the target, the probe, or any combination thereof. In some embodiments, the method further comprises sequencing the target, the probe, or any combination thereof. In some embodiments, the method further comprises converting the expression levels of the target sequences into a likelihood score that indicates the probability that a biological sample is from a patient who will exhibit no evidence of disease, who will exhibit systemic cancer, or who will exhibit biochemical recurrence. In some embodiments, the target sequences are differentially expressed the cancer. In some embodiments, the differential expression is dependent on aggressiveness. In some embodiments, the expression profile is determined by a method selected from the group consisting of RT-PCR, Northern blotting, ligase chain reaction, array hybridization, and a combination thereof.

In some embodiments is a method of predicting whether an individual is susceptible to developing a cancer. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the method further comprises a software module executed by a computer-processing device to compare the expression profiles. In some embodiments, the deviation is the expression level of one or more targets from the sample is at least about 30% greater than the expression level of one or more targets from a control or standard derived from a healthy individual or population of healthy individuals. In some embodiments, the deviation is the expression level of one or more targets from the sample is less than the expression level of one or more targets from a control or standard derived from a healthy individual or population of healthy individuals. In some embodiments, the deviation is the expression level of one or more targets from the sample is at least about 30% less than the expression level of one or more targets from a control or standard derived from a healthy individual or population of healthy individuals. In some embodiments, the method further comprises using a machine to isolate the target or the probe from the sample. In some embodiments, the method further comprises contacting the sample with a label that specifically binds to the target, the probe, or a combination thereof. In some embodiments, the method further comprises amplifying the target, the probe, or any combination thereof. In some embodiments, the method further comprises sequencing the target, the probe, or any combination thereof. In some embodiments, the method further comprises converting the expression levels of the target sequences into a likelihood score that indicates the probability that a biological sample is from a patient who will exhibit no evidence of disease, who will exhibit systemic cancer, or who will exhibit biochemical recurrence. In some embodiments, the target sequences are differentially expressed the cancer. In some embodiments, the differential expression is dependent on aggressiveness. In some embodiments, the expression profile is determined by a method selected from the group consisting of RT-PCR, Northern blotting, ligase chain reaction, array hybridization, and a combination thereof.

In some embodiments is a method of predicting an individual's response to a treatment regimen for a cancer, comprising: (a) obtaining an expression profile from a sample obtained from the individual; (b) comparing the expression profile from the sample to an expression profile of a control or standard; and (c) predicting the individual's response to a treatment regimen based on (i) the deviation of the expression profile of the sample from a control or standard derived from a healthy individual or population of healthy individuals, or (ii) the similarity of the expression profiles of the sample and a control or standard derived from an individual or population of individuals who have or have had the cancer. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the method further comprises a software module executed by a computer-processing device to compare the expression profiles. In some embodiments, the deviation is the expression level of one or more targets from the sample is at least about 30% greater than the expression level of one or more targets from a control or standard derived from a healthy individual or population of healthy individuals. In some embodiments, the deviation is the expression level of one or more targets from the sample is less than the expression level of one or more targets from a control or standard derived from a healthy individual or population of healthy individuals. In some embodiments, the deviation is the expression level of one or more targets from the sample is at least about 30% less than the expression level of one or more targets from a control or standard derived from a healthy individual or population of healthy individuals. In some embodiments, the method further comprises using a machine to isolate the target or the probe from the sample. In some embodiments, the method further comprises contacting the sample with a label that specifically binds to the target, the probe, or a combination thereof. In some embodiments, the method further comprises amplifying the target, the probe, or any combination thereof. In some embodiments, the method further comprises sequencing the target, the probe, or any combination thereof. In some embodiments, the method further comprises converting the expression levels of the target sequences into a likelihood score that indicates the probability that a biological sample is from a patient who will exhibit no evidence of disease, who will exhibit systemic cancer, or who will exhibit biochemical recurrence. In some embodiments, the target sequences are differentially expressed the cancer. In some embodiments, the differential expression is dependent on aggressiveness. In some embodiments, the expression profile is determined by a method selected from the group consisting of RT-PCR, Northern blotting, ligase chain reaction, array hybridization, and a combination thereof.

A method of prescribing a treatment regimen for a cancer to an individual in need thereof, comprising (a) obtaining an expression profile from a sample obtained from the individual; (b) comparing the expression profile from the sample to an expression profile of a control or standard; and (c) prescribing a treatment regimen based on (i) the deviation of the expression profile of the sample from a control or standard derived from a healthy individual or population of healthy individuals, or (ii) the similarity of the expression profiles of the sample and a control or standard derived from an individual or population of individuals who have or have had the cancer. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the method further comprises a software module executed by a computer-processing device to compare the expression profiles. In some embodiments, the deviation is the expression level of one or more targets from the sample is at least about 30% greater than the expression level of one or more targets from a control or standard derived from a healthy individual or population of healthy individuals. In some embodiments, the deviation is the expression level of one or more targets from the sample is less than the expression level of one or more targets from a control or standard derived from a healthy individual or population of healthy individuals. In some embodiments, the deviation is the expression level of one or more targets from the sample is at least about 30% less than the expression level of one or more targets from a control or standard derived from a healthy individual or population of healthy individuals. In some embodiments, the method further comprises using a machine to isolate the target or the probe from the sample. In some embodiments, the method further comprises contacting the sample with a label that specifically binds to the target, the probe, or a combination thereof. In some embodiments, the method further comprises amplifying the target, the probe, or any combination thereof. In some embodiments, the method further comprises sequencing the target, the probe, or any combination thereof. In some embodiments, the method further comprises converting the expression levels of the target sequences into a likelihood score that indicates the probability that a biological sample is from a patient who will exhibit no evidence of disease, who will exhibit systemic cancer, or who will exhibit biochemical recurrence. In some embodiments, the target sequences are differentially expressed the cancer. In some embodiments, the differential expression is dependent on aggressiveness. In some embodiments, the expression profile is determined by a method selected from the group consisting of RT-PCR, Northern blotting, ligase chain reaction, array hybridization, and a combination thereof.

In some embodiments, the system further comprises electronic memory for capturing and storing an expression profile. In some embodiments, the system further comprises a computer-processing device, optionally connected to a computer network. In some embodiments, the system further comprises a software module executed by the computer-processing device to analyze an expression profile. In some embodiments, the system further comprises a software module executed by the computer-processing device to compare the expression profile to a standard or control. In some embodiments, the system further comprises a software module executed by the computer-processing device to determine the expression level of the target. In some embodiments, the system further comprises a machine to isolate the target or the probe from the sample. In some embodiments, the system further comprises a machine to sequence the target or the probe. In some embodiments, the system further comprises a machine to amplify the target or the probe. In some embodiments, the system further comprises a label that specifically binds to the target, the probe, or a combination thereof. In some embodiments, the system further comprises a software module executed by the computer-processing device to transmit an analysis of the expression profile to the individual or a medical professional treating the individual. In some embodiments, the system further comprises a software module executed by the computer-processing device to transmit a diagnosis or prognosis to the individual or a medical professional treating the individual. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas.

EXAMPLES

Example 1. Validation Studies in Subjects with Prostate Cancer

Study Design

This study used a previously described case-control study for biomarker discovery and a case-cohort for independent validation.

The discovery study was a nested case-control described in detail in Nakagawa et al 2008. Archived formalin-fixed paraffin embedded (FFPE) blocks of tumors were selected from 621 patients that had undergone a radical prostatectomy (RP) at the Mayo Clinic Comprehensive Cancer Centre between the years 1987-2001 providing a median of 18.16 years of follow-up. The patients were randomly split into a training and test sets; the training set was used for biomarker discovery and classifier development and the testing set was used to measure performance and with model selection.

Patients were retrospectively classified into one of three outcomes: NED: No evidence of disease for those patients with no biochemical or other clinical signs of disease progression (at least 10 years follow-up); PSA: prostate-specific antigen biochemical recurrence for those patients with two successive increases in PSA measurements above an established cut-point of >0.2 ng/(with the subsequent measure 0.05 ng/mL above the first measurement) within 5 years of RP and no detectable metases up to 10 years after RP; METS: for those patients experience BCR within 5 years of RP and that developed metastases (confirmed by bone or CT scan) within 5 years of BCR. Patient selection for nested case-control design is outlined in Nakagawa.

On average, METS patients were diagnosed within 3.22 years following BCR and 5.79 years following RP, implying that this METS group experienced rapid onset of metastatic disease. Some PSA patients do experience metastatic disease (n=18, or 9.9% of all PSA patients in the discovery study), however, these patients have the event 10 years beyond RP and thus are outside the MET definition. Due to the condition that both PSA and MET groups had to experience BCR event within 5 years of RP, there is no statistically significant difference for the time to BCR between PSA (median: 1.70 years [IQR:0.65-3.44]) and MET (median: 2.26 years [IQR: 0.78-3.94]) groups. Patients in this study did not receive a consistent treatment regimen, and may be highly treated with adjuvant interventions compared to other cohorts.

Where possible we account for adjuvant interventions in analysis to mitigate its impact as a confounding factor (See Statistical Analysis).

We conducted a study that investigated the differences between NED, PSA and METS outcome groups and found there to be no statistically significant differences between the NED and PSA groups, with the largest difference in genomic and clinicopathologic variables to be found when comparing METS against NED or PSA groups. We have evidence to believe that NED and PSA groups may represent a less aggressive type of prostate cancer, and that these patients will likely not experience metastatic progression in their life-time, conversely METS patients represent rapid disease onset and more aggressive prostate cancer. To maximize discovery of biomarkers that identified oncogenic drivers of aggressive disease, we combined the NED and PSA groups into a unified Non-METS group to compare against the METS.

The discovery study included 621 patients who underwent RP at the Mayo Clinic between 1987-2001. Patients who received neo-adjuvant interventions were excluded. After chip quality control (www.affymetrix.com), 545 unique patients (209 with METS after RP and 336 with BCR only or NED) were available for the biomarker discovery study (median follow-up, 18.2 years). The study patients were further subdivided by random draw into training (n=359) and testing (n=186) subsets, balancing for the distribution of clinicopathologic variables as previously described.

Subjects for independent validation were identified from a population of 1,010 men prospectively enrolled in the Mayo Clinic tumor registry who underwent RP for prostatic adenocancinoma from 2000-2006 and were at high risk for disease recurrence. High-risk for recurrence was defined by pre-operative PSA>20 ng/mL, or pathological Gleason score ≥8, or seminal vesicle invasion (SVI) or GPSM (Gleason, PSA, seminal vesicle and margin status) score ≥10. Data was collected using a case-cohort design over the follow-up period (median, 8.06 years), 71 patients developed metastatic disease (METS) as evidenced by positive bone and/or CT scans. Data was collected using a case-cohort design, which involved selection of all 73 cases combined with a random sample of 202 patients (~20%) from the entire cohort. After exclusion for tissue unavailability and samples that failed microarray quality control, the independent validation cohort consisted of 219 (69 cases) unique patients.

RNA Extraction and Microarray Hybridization

Following pathological review of FFPE primary prostatic adenocancinoma specimens from patients in the discovery and validation cohorts, tumor was macrodissected from surrounding stroma from 3-4 10 µm tissue sections. Total RNA was extracted, amplified using the Ovation FFPE kit (NuGEN, San Carlos, Calif.), and hybridized to Human Exon 1.0 ST GeneChips (Affymetrix, Santa Clara, Calif.) that profiles coding and non-coding regions of the transcriptome using approximately 1.4 million probe selection regions, hereinafter referred to as features.

For the discovery study, total RNA was prepared as described herein. For the independent validation study, total RNA was extracted and purified using a modified protocol for the commercially available RNeasy FFPE nucleic acid extraction kit (Qiagen Inc., Valencia, Calif.). RNA concentrations were determined using a Nanodrop ND-1000 spectrophotometer (Nanodrop Technologies, Rockland, Del.). Purified total RNA was subjected to whole-transcriptome amplification using the WT-Ovation FFPE system according to the manufacturer's recommendation with minor modifications (NuGen, San Carlos, Calif.). For the discovery study the WT-Ovation FFPE V2 kit was used together with the Exon Module while for the validation only the Ovation® FFPE WTA System was used. Amplified products were fragmented and labeled using the Encore™ Biotin Module (NuGen, San Carlos, Calif.) and hybridized to Affymetrix Human Exon (HuEx) 1.0 ST GeneChips following manufacturer's recommendations (Affymetrix, Santa Clara, Calif.). Only 604 out of a total 621 patients had specimens available for hybridization.

Microarray Processing

Microarray Quality Control

The Affymetrix Power Tools packages provide an index characterizing the quality of each chip, independently, named "pos_vs_neg_AUC". This index compares signal values for positive and negative control probesets defined by the manufacturer. Values for the AUC are in [0, 1], arrays that fall under 0.6 were removed from analysis.

Only 545 unique samples, out of the total 604 with available specimens (inter- and intra-batch duplicates were run), were of sufficient quality for further analysis; 359 and 187 samples were available from the training and testing sets respectively. We re-evaluated the variable balance between the training and testing sets and found there to be no statistically significant difference for any of the variables.

Microarray Normalization, Probeset Filtering, and Batch Effect Correction

Probeset summarization and normalization was performed by fRMA, which is available through Bioconductor. The fRMA algorithm relates to RMA with the exception that it specifically attempts to consider batch effect during probeset summarization and is capable of storing the model parameters in so called 'frozen vectors'. We generated a custom set of frozen vectors by randomly selecting 15 arrays from each of the 19 batches in the discovery study. The frozen vectors can be applied to novel data without having to renormalize the entire dataset. We furthermore filtered out unreliable PSRs by removing cross-hybridizing probes as well as high PSRs variability of expression values in a prostate cancer cell line and those with fewer than 4 probes. Following fRMA and filtration the data was decomposed into its principal components and an analysis of variance model was used to determine the extent to which a batch effect remains present in the first 10 principal components. We chose to remove the first two principal components, as they were highly correlated with the batch processing date.

Non-Coding RNA Analysis

Sequence information from each probe in a PSR can be aligned and annotated against the human reference genome by xmapcore (Yates, et al., X:Map: Annotation and visualization of genome structure for Affymetrix exon array analysis, Nucleic Acids Res. (2008), Epub.) Using annotation data from the human genome version hg19/GRCh37 (Ensembl annotation release 62), we categorize the PSRs into coding, non-coding (UTR) and non-coding (intronic) as defined by xmapcore.

The PSRs that cannot be categorized in the groups above are further categorized as follows:

Non-coding (Non-unique): one or more probes don't align perfectly to the genome, or one or more probes align perfectly to multiple regions of the genome.

Non-coding (ncTranscript): PSR correspond to the exon of a non-coding transcript.

Non-coding (CDS_Antisense): PSR corresponds to a segment in the opposite strand of the coding sequence of a protein-coding transcript.

Non-coding (UTR_Antisense): PSR corresponds to a segment in the opposite strand of the UTR sequence (5'- or 3') of a transcript.

Non-coding (Intronic_Antisense): PSR correspond to a segment in the opposite strand of the intronic sequence of a protein-coding transcript.

Non-coding (ncTransciipt_Antisense): PSR correspond to the exon of a non-coding transcript in the opposite strand.

Non-coding (Intergenic): if the probes were not categorized under any of the groups above and it is annotated as 'intergenic' by xmapcore.

We additionally used xmapcore to annotate the gene symbol, gene synonym, Ensembl gene ID and biological description for any PSRs that overlapped with a transcript when necessary; this excludes alignments to non-coding (non-unique) and non-coding (intergenic) sequences.

Example 2: A 43-Biomarker Set for Prostate Cancer

Figure 3:
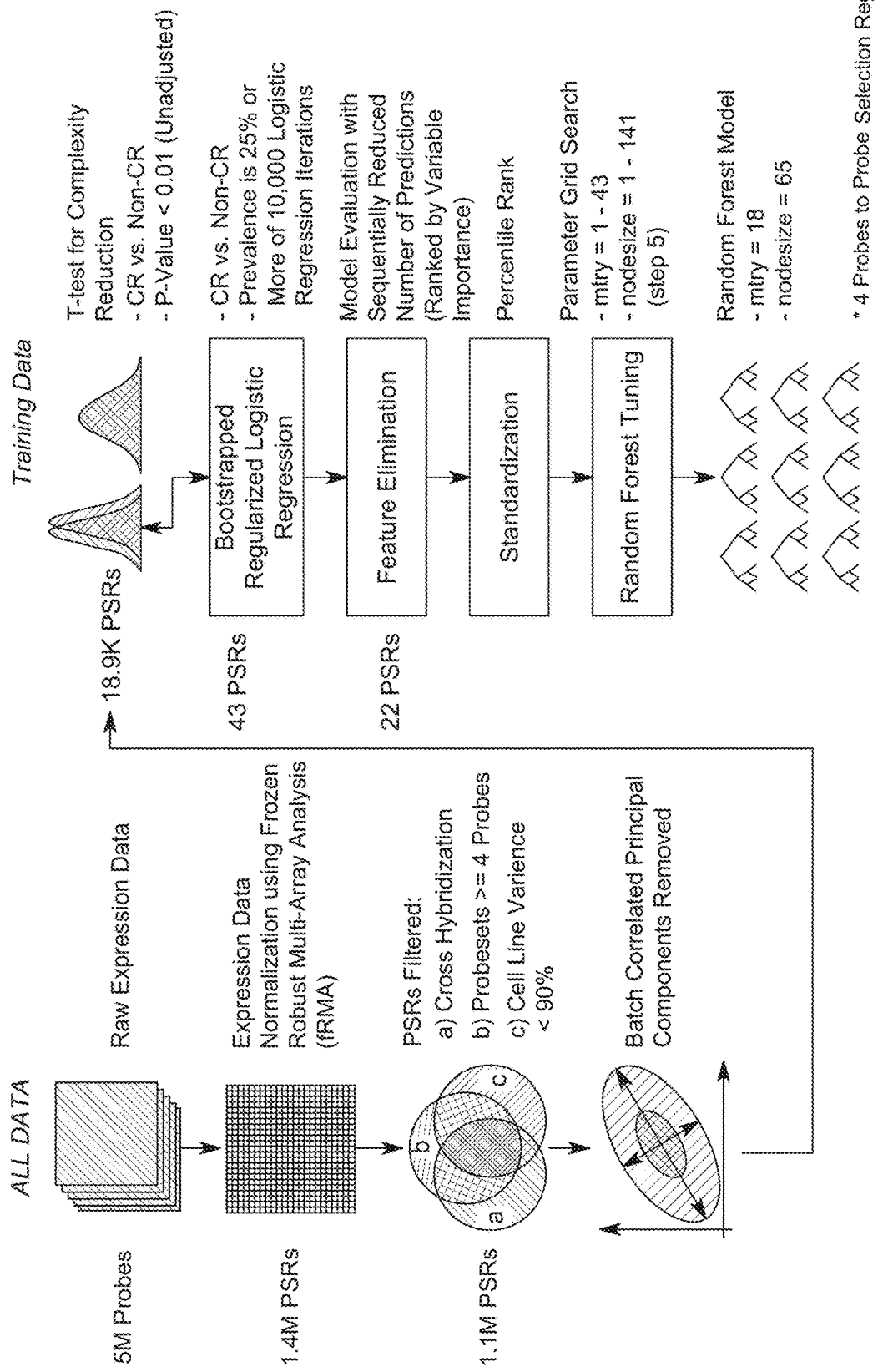
FIG. 3. shows 43-biomarker set methods.
Figure 4:
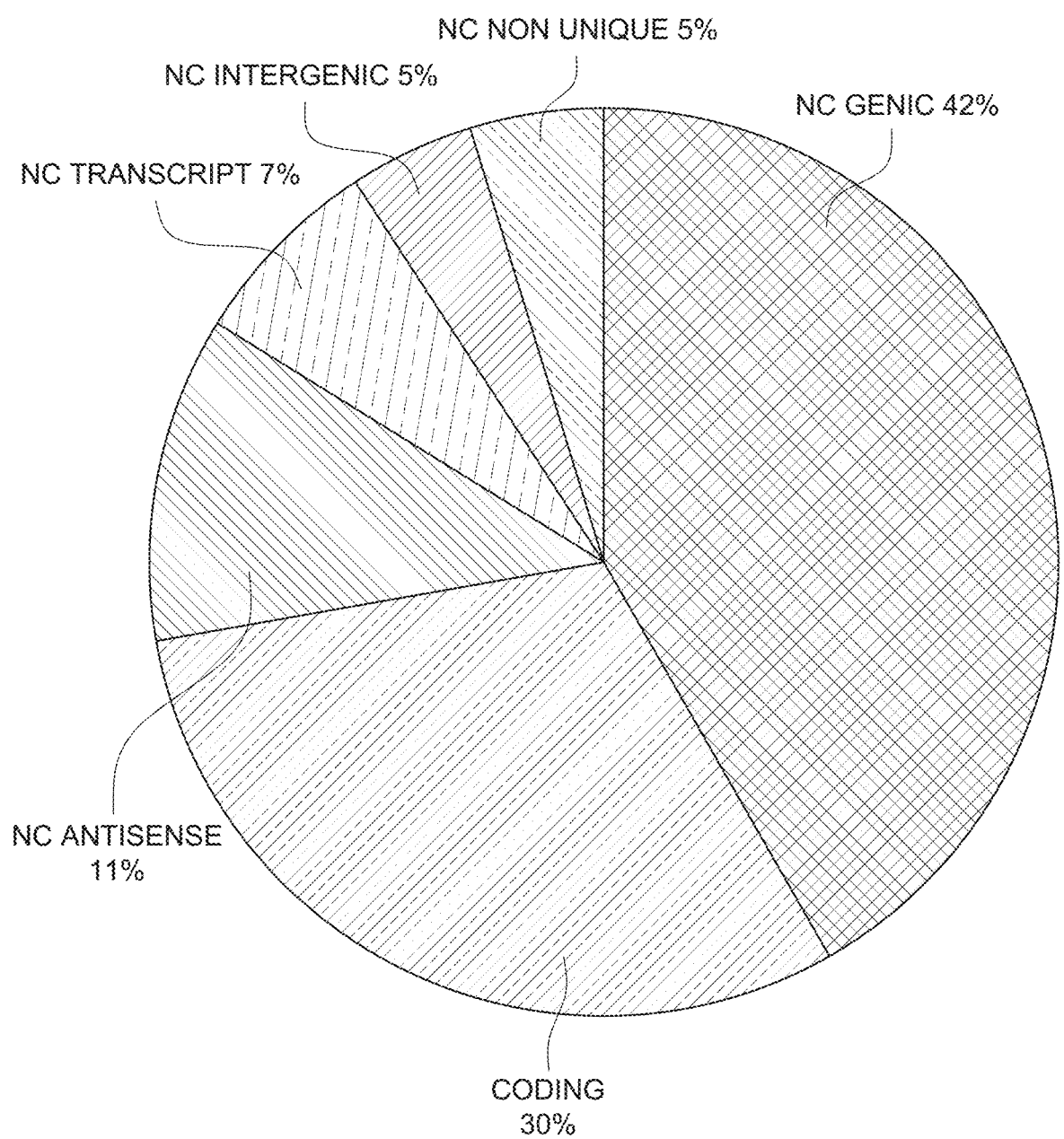
FIG. 4. shows annotation of the 43-biomarker set.

Overview of the entire microarray analysis pipeline is provided in FIG. 3.
Feature Selection The remaining features following the analysis in Example 1 were subjected to filtration by a t-test between the METS and non-METS samples in the training set (n=359). Using a p-value cut-off of 0.01, 18,902 features remain in analysis for further selection. Feature selection was performed by regularized logistic regression using the elastic-net penalty through the glmnet v1.7 package available in R with an alpha-value of 0.5 with three-fold cross validation. The regularized regression, with cross validation, was bootstrapped over 1000 times using all training data (n=359); with each iteration of bootstrapping we tabulated features that had a non-zero co-efficient. Features that were selected in at least 25% of the total runs were used for model building.
Non-Coding RNA Analysis We annotated the 43-biomarker set with labels described in Example 1 to identify the extent of non-coding features. We show the various labels within the 43-biomarker set in FIG. 4.

Figure 5:
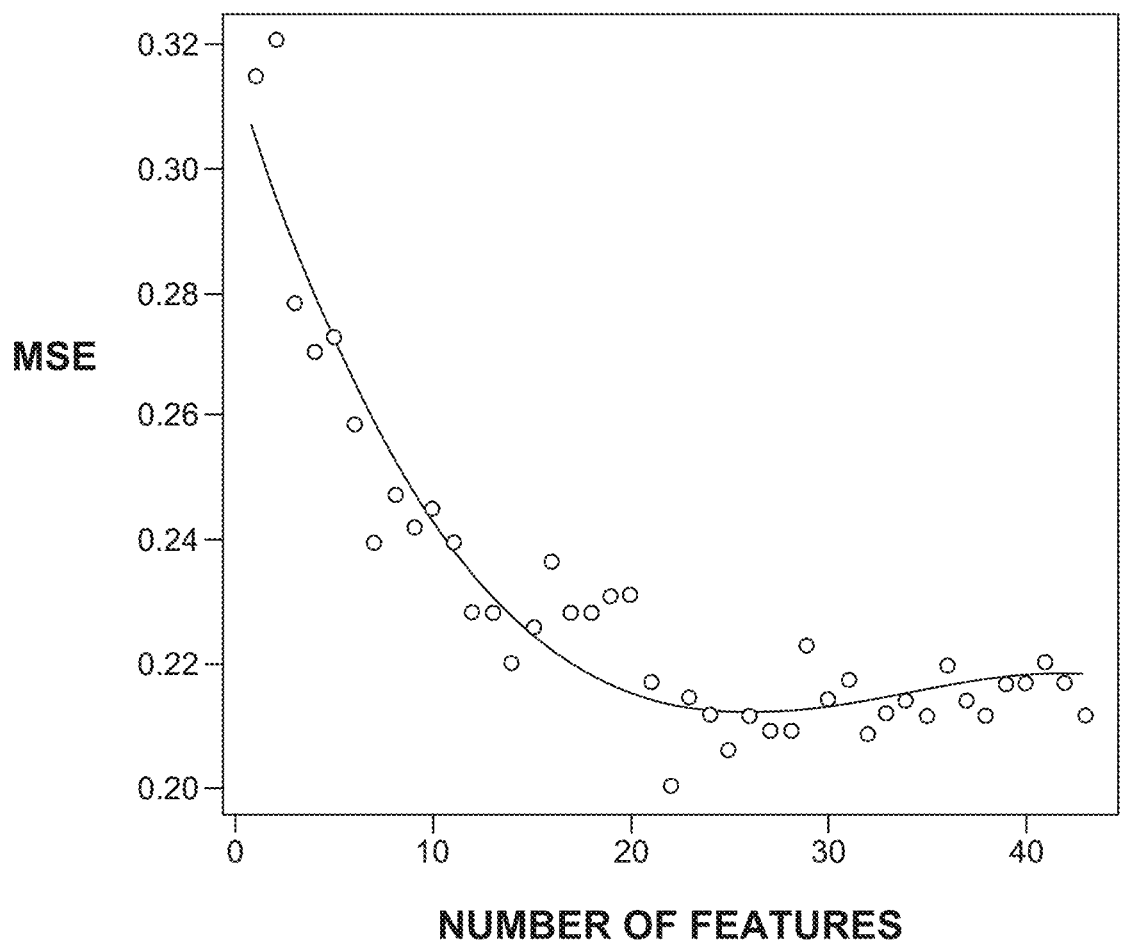
FIG. 5. shows a graph of biomarker variable mean squared error for selection of a 22-biomarker signature.
Figure 6A:
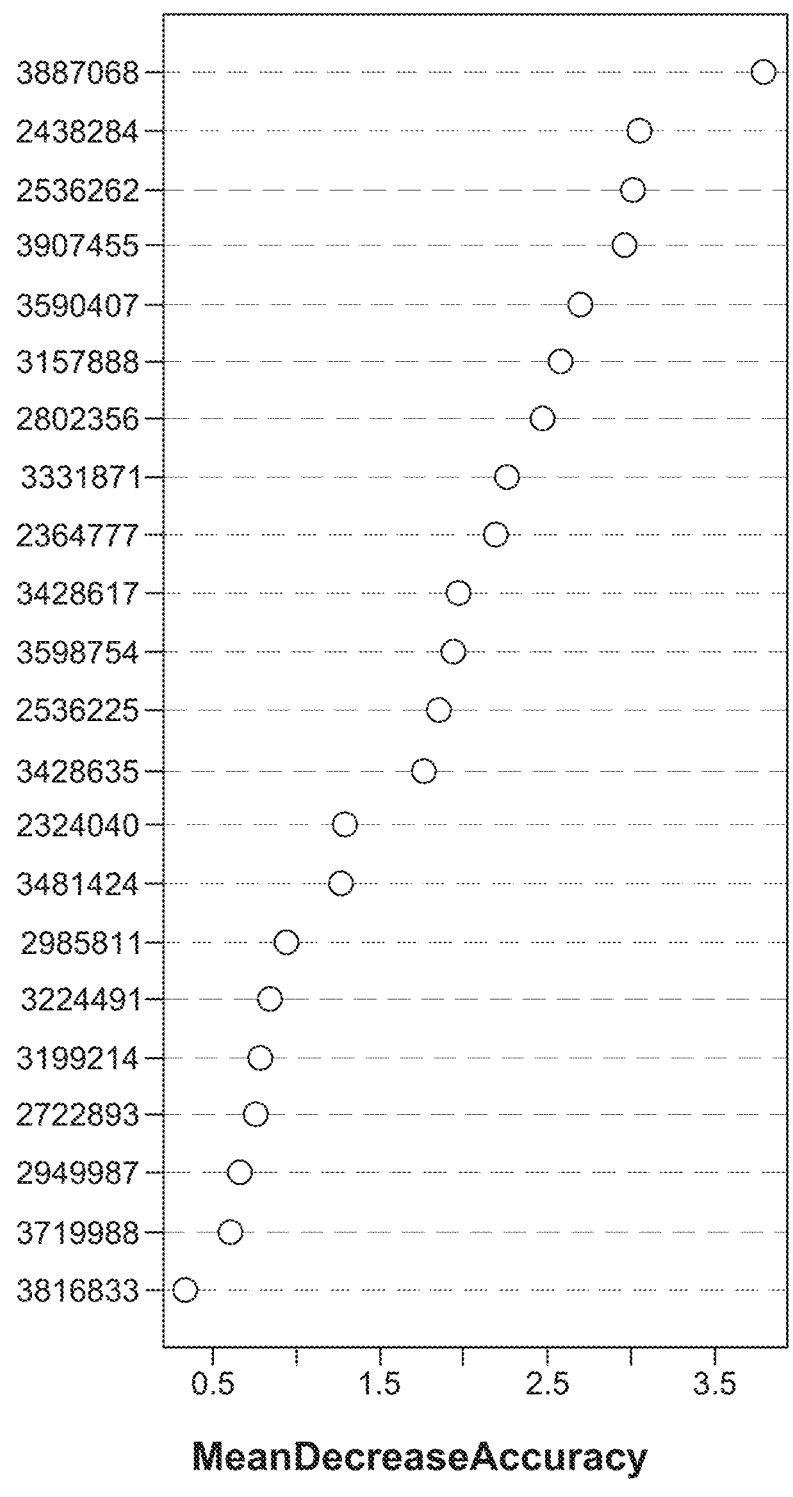
FIGS. 6A-6B show a biomarker signature variable importance plot.
Figure 6B:
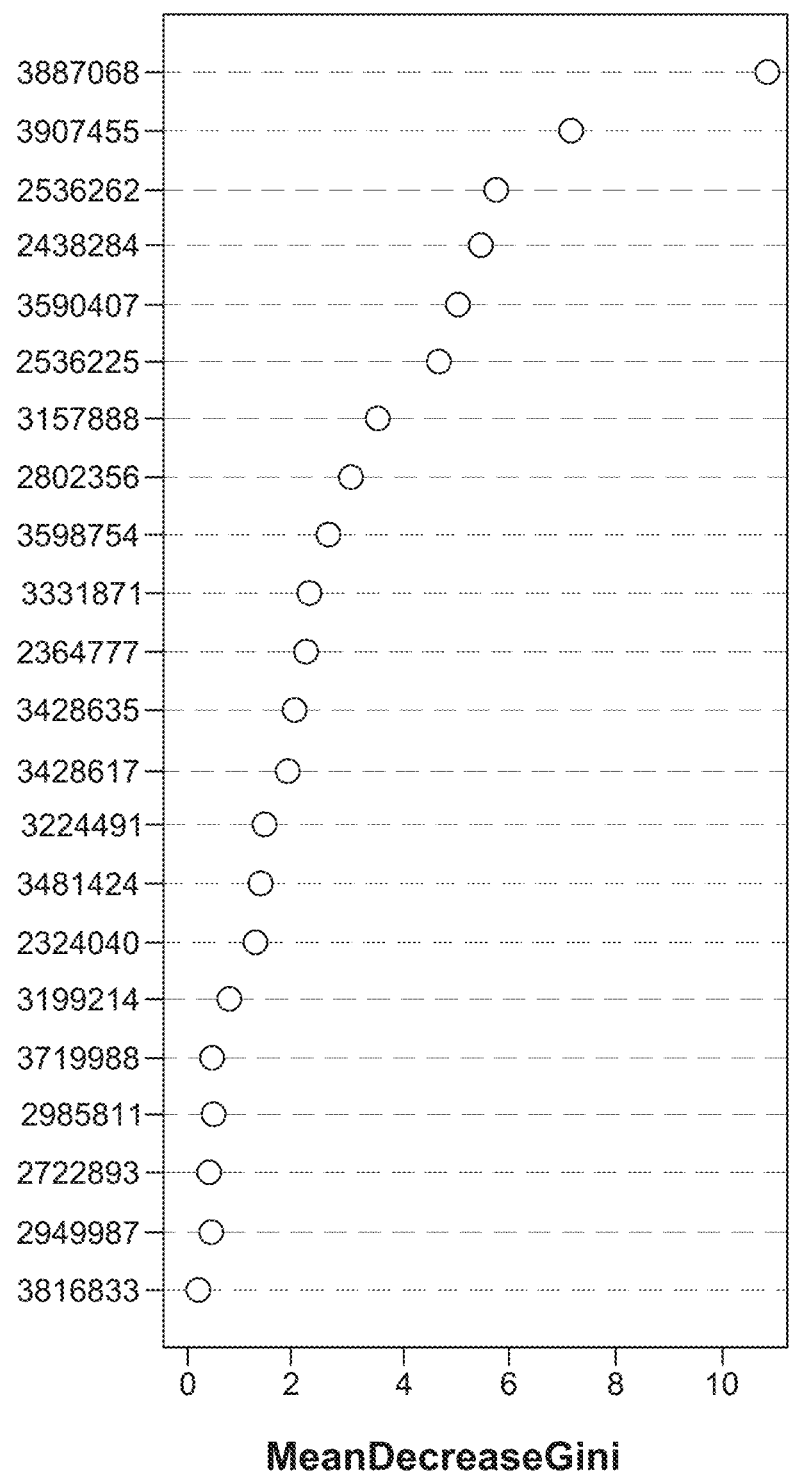
Figure 7:
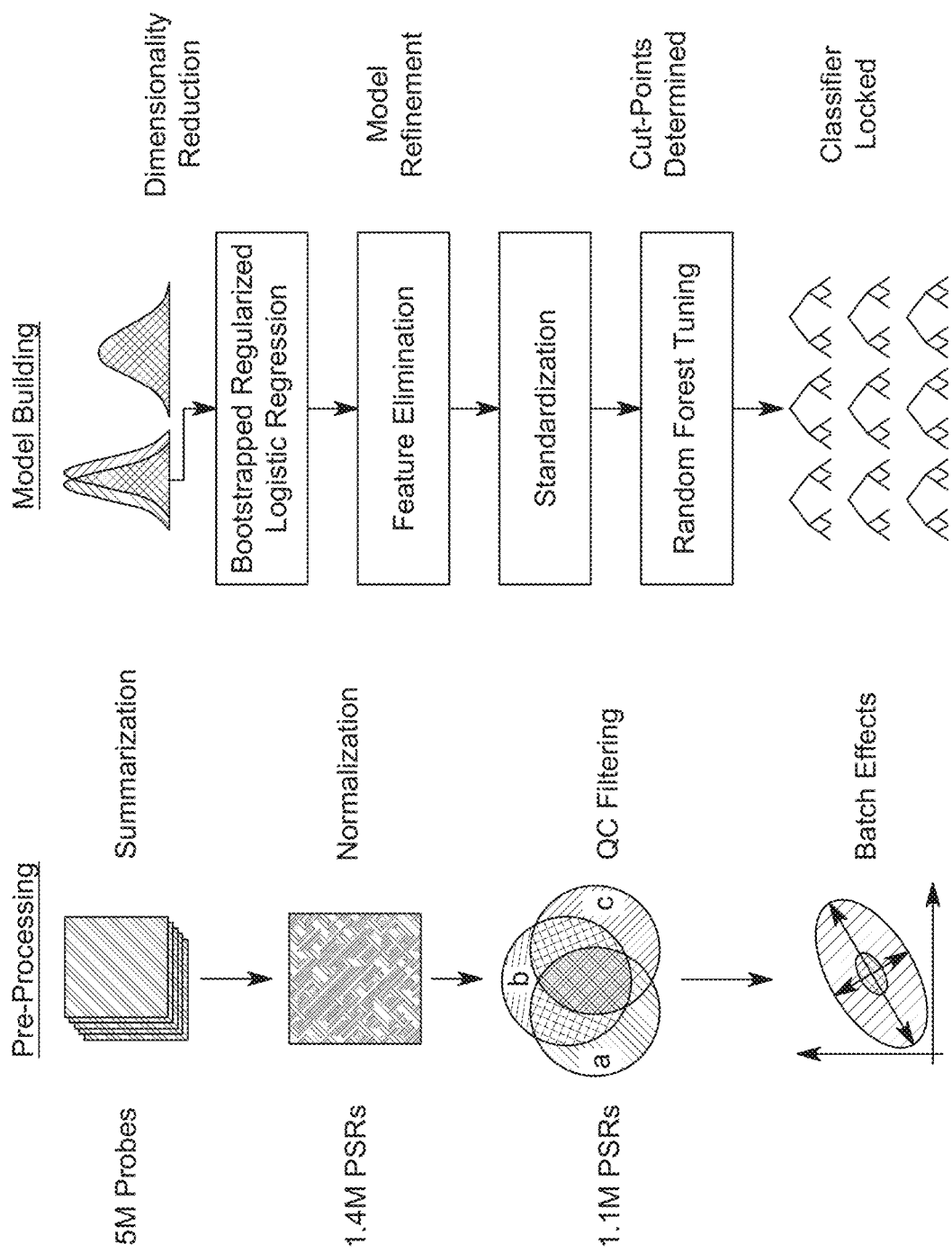
FIG. 7. shows development of a classifier.

Example 3: A 22-Biomarker Signature for Prostate Cancer and Comparison to Clinical and Intergrated Models To further ensure robustness of the features in the signature, we applied a final filtration method that would establish the minimal number of features required to minimize the mean squared error (MSE) of the model. To do this we used the rfcv function from the randomForest package, using 10-fold cross validation and a step value of 0.9. This method will order the features in accordance to their variable importance and iteratively remove 10% of lowest ranking features and measure the MSE at each step. We selected the number of features that were at the knee of the curve, shown in FIG. 5. At all features to the left of this knee have a highly variable MSE, which becomes more stable to the right of the knee of the curve. The knee of the curve occurs at approximately 22 features. FIG. 6 calculated the variable importance by ranking the features according to their mean decrease in accuracy (MDA) and mean decrease in gini (MDG). Some features have low MDA and MDG, which may warrant their removal from the marker set, however FIG. 5 shows that the inclusion of even some of the less differentiating features still contributed to a lower MSE. An overview of the feature selection and microarray methods is shown in FIG. 7.
Classifier Development We developed three classifiers using the aforementioned 22 features, clinicopathologic variables, and a combination of both. We referred to the classifiers as the genomic classifier (GC), clinical classifier (CC) and integrated genomic clinical classifier (GCC); they are described in detail below. The primary endpoint for classifier development was the METS event. Although it is typical to report probabilities of progression at 2, 5, 7 or 10 years after METS, the design of the discovery study prevents us from reporting probabilities that are meaningful outside of study. For this reason, the scores for all of the aforementioned models prognosticate whether a given individual will experience metastatic disease progression, as this endpoint is not subject to modeling disease prevalence or time to an event but rather the presence or absence of features that indicate disease aggression.
Genomic Classifier (GC)

A total of 22 features were used for model building. As a further method of standardization, the expression values for the 22 features were percentile ranked for each patient. We used a random forest from the randomForest package available in R for model building and used the tune function, from the e1071 package, to identify the optimal model parameters; the optimal parameters were established to be: nodesize=80, ntree=700, mtry=15. The tuning parameters were selected to optimize classification accuracy in the training set. The model built from the training data is frozen and stored for future application to novel data. The model for classification built from the 22-biomarker feature set is henceforth referred to as the genomic classifier (GC) when applied to novel data. Notable, the final feature set is such that most of the 22 features in GC were ncRNA and only three were from protein-encoding mRNA.

The GC outputs a score between [0,1], where 1 indicates higher metastatic potential. The score is derived as an output of the random forest, and rather than representing a probability it represents the total percentage of the trees in the forest that classified a new case as METS. Alternatively, it may also be said that each decision tree within the random forest decides whether the expression levels of the 22 features in a given tumor sample is more representative of MET disease or not. We used a 0.5 cutoff to classify patients as having METS or not because it is objective and used the simple Majority rule logic.
Clinical Classifier (CC)

A clinical classifier (CC) for predicting the METS end point was developed using the following clinicopathologic variables: Lymph node invasion status (LNI); Surgical Margin Status (SMS); Seminal Vesicle Invasion (SVI); Extra Capsular Extension (ECE); Pathological Gleason Score; and the pre-operative PSA. The first four clinical variables (LNI, SMS, SVI and ECE) are used as binary variables, indicating present or not; the pre-operative PSA values are taken to log 10. The clinical variables were assembled in a logistic regression and the trained model was used to predict METS in the testing set and validation study. CC produces a probability between 0 and 1, where 0 indicates low metastatic potential and 1 indicates a high metastatic potential.

Example 4: A 22-Marker Genomic Classifier (GC) Outperformed Previously Reported Genomic Signatures and Individual Gene Biomarkers As described in Example 3, a final set of 22 markers was selected for building a random forest classifier. The highdensity array used in this study permits measurement of the expression patterns of RNAs associated with multiple biological processes in prostate cancer progression. Also, this transcriptome-wide approach allowed interrogation of a much richer genomic dataset, including thousands of ncRNA. Furthermore, the genomic markers measure the biological potential of the tumor to metastasize. The biological processes represented in the 22 markers include cell cycle progression, cell adhesion, tumor cell motility, migration and immune system modulation. Multidimensional scaling analysis depicts clustering of cases and controls based on the expression of these 22 markers (FIGS. 1 and 2). Controls correspond to pooled NED and PSA patients since, at a fold-change threshold of 1.5 (after correcting for false-discovery), only 2 (out of ~1.4 million) features were found to be differentially expressed between these two groups, compared to 1187 and 887 in metastasis outcomes compared to NED and PSA groups. A random forest machine-learning algorithm was used to generate GC scores on the training and testing set after assembling the 22 markers with forest parameters to optimize for highest accuracy in the training set. The performance of GC was compared to that of previously published gene signatures: Agell et al 2012, Bibikova et al 2007, Bismar et al 2006, Cuzick et al 2011, Glinsky et al 2005, LaPointe et al 2004, Larkin et al 2012, Nakagawa et al 2008, Olmos et al 2012, Penney et al 2011, Ramaswamy et al 2003, Ross et al 2012, Talantov et al 2010, Varambally et al 2005 and Yu et al 2007 and individual genomic markers associated with prostate cancer progression including CHGA, DAB2IP, GOLPH2, PAP, ETV1 and ERG, KI-67, PSA, PSCA, PSMA, AMACR, GSTP1, PCA3, B7-H3, TOP2A and CAV1. Each genomic marker and gene in the signatures were mapped to its associated Affymetrix core transcript cluster (www.affymetrix.com/analysis/index.affx) where available, otherwise the extended transcript cluster was used. Based on the fRMA summarized expression values for the individual genes, the signatures were modeled in the training set using a random forest and tuned with the tune.randomForest function from the e1071 R package. Tuning involved performing a 20 by 20 grid search to find the optimal "mtry" and "nodesize" model parameters evaluated via 5-fold cross validation in order to maximize accuracy.

The performance of the classifiers and the individual genes was subsequently assessed in both training and testing sets. As expected, we observed high AUCs in training for nearly all the external signatures, similar to what was observed with GC. When applied to testing, the AUC for each model decreased. Among the 17 external signatures that were modeled, 12 were statistically significant predictors of metastasis (e.g., their 95% confidence intervals did not drop below a threshold random chance AUC of 0.5). The AUC of GC was 0.08 points higher than the top performing external signature, the 16-gene signature reported by Bibikova et al, which had an AUC of 0.68 (95% CI: 0.60-0.76). In contrast to the expression signature models, the performance of the 16 single genes tested were expected to be similar in the training and testing sets. These genomic markers showed an overall agreement in performance, with differences in significance possibly explained by the smaller sample size of the testing set compared to the training set. Of the 16 genomic markers, only B7-H3 (CD276), GSTP1 and PCA3 were statistically significant in both the training and testing sets. Again, none of the individual genomic markers outperformed GC or the top performing clinical predictor, GS (AUCs≤0.64).

Example 5: A 22-Marker Genomic Classifier (GC) Outperformed Individual Clinicopathologic Variables and was Prognostic within Different Gleason Scores Groups Clinical variables were calculated, categorized or transformed as follows. Pathological Gleason Score (GS, or pathGS) was dichotomized into groups with the threshold of ≥8; although convention is to segregate GS into three groups (≤6, 7, ≥8) the relative lack of patients with GS≤6 prompted the dichotomization of GS. The pre-operative PSA (pPSA), measured immediately prior to RP, was log 2-transformed. The following variables were binary: Extra-capsular Extension (ECE); Seminal Vesicle Invasion (SVI); Surgical Margins (SM+, or SMS) and Lymph Node Involvement (N+, or LNI). Hormone and radiation therapy were included as separate binary covariates if administered in an adjuvant (<90 days post RP) or salvage (following PSA rise) setting. Treatments administered subsequent to clinical metastasis were not included.

In the training set (see Example 1), ROC area-under the curve (AUC) values for GC, CC and GCC were 0.90, 0.76 and 0.91 respectively, outperforming all individual clinical variables: GSm N+, ECE, SVI, SM+, N+, pPSA and Tumor Volume. In the testing set, GC and GCC had the highest AUC of 0.75, and 0.74, respectively for predicting cases. The clinical-only CC had an AUC of 0.69, which was only marginally better than pathological Gleason score alone (0.65). The shape of the ROC curves for GC and GCC showed that these models had the highest specificity and sensitivity compared to clinical models above a threshold of ~50% specificity.

A blinded study independently validated GC for prediction of clinical metastasis (metastasis) following radical prostatectomy. The results showed that the GC model had improved performance over any individual clinicopathologic variable or multivariable prediction model. In this independent validation set, the AUC of 5-year survival ROC curves demonstrated that GC had higher discriminatory ability than individual clinicopathologic variables. The GC model had an AUC of 0.79 for predicting clinical metastasis at 5 years post RP with median follow up of 6.7 years. Furthermore, 5-year survival decision curve analysis on the independent validation set showed that GC had a higher net benefit over a wider range of 'decision-to-treat' probabilities than clinicopathologic factors.

Example 6: A 2,040 Biomarker Library for Prostate Cancer Progression

In order to define, from the entire set of 1.4 million features, a comprehensive library of biomarkers that presents prognostic ability, the Discovery Set (Training and Testing) presented in Example 1 was processed as follows. First, all features with a probe count lower than 4 or with cross-hybridizing probes as defined by affymetrix (www.affymetrix.com) were removed. Second, a background filter was applied in order to ensure signal in the expression capture for each feature. To achieve this, features that had a median expression value in the group of METS patients and in the group of non-METS patients (separately) lower than 1.2 times the background signal (captured by the control antigenomic probes defined by affymetrix (www.affymetrix.com)) were removed. Third, the statistical significance of the differential expression observed between the METS and non-METS groups was assessed using the Kolmogorov-Smirnov test for each feature. Those features with a p-value greater than 0.05 were removed. Last, a Random forest variable importance was calculated by building a random forest with 450,000 trees. Features with Mean Decrease Gini (or MDG)<=0 were discarded and features with MDG>6.5e-3 and Mean Decrease in Accuracy (or MDA) >0 were selected, reducing the feature set to 2,040 features. MDA is defined as the average difference in accuracy of the true variable vs the variable randomized for trees in the forest. MDG is defined as the mean of the change in gini between a parent node and a child node when splitting on a variable across the whole forest.

These represent the most important features (based on MDG and MDA) that are statistically significant (based on Kolmogorov-Smirnov Test) for the differential expression between METS and non-METS patients and provides a biomarker library for prostate cancer progression.

What is claimed is:

1. A system for facilitating cancer-related prediction accuracy of a trained model, without requiring renormalization of the entirety of a given training dataset for training the model for novel data, by arranging preprocessing vectors and a trained random forest model, that are derived from the same training dataset, to respectively preprocess sample target data and generate predictions with the preprocessed data, the system comprising:
   one or more processors and non-transitory machine-readable media storing instructions that, when executed by the one or more processors, cause operations comprising:
      accessing a random forest machine learning model comprising features that are derived from a training dataset and selected for the random forest machine learning model;
      obtaining target data derived from a target sample;
      normalizing, using frozen vectors derived from randomly-selected subsets of the training dataset, the target data to generate processed data; and
      after generating the processed data using the frozen vectors, generating, using the random forest machine learning model on the processed data and without requiring renormalization of the entirety of the training dataset, a likelihood score related to cancer occurrence by inputting the processed data into nodes of the random forest machine learning model, wherein the nodes and the frozen vectors are both derived from the training dataset.

2. The system of claim 1, wherein the features are selected for the random forest machine learning model based on the features having a non-zero co-efficient less than or equal to a p-value threshold in multiple bootstrapping processes performed on different subsets of the training dataset.

3. A method for facilitating cancer-related prediction accuracy of a trained model without requiring renormalization of the entirety of a given training dataset for training the model for novel data, the method comprising:
   accessing a machine learning model comprising features that are derived from a training dataset and selected for the machine learning model;
   obtaining target data derived from a target sample;
   normalizing, using frozen vectors derived from randomly-selected subsets of the training dataset, the target data to generate processed data; and
   after generating the processed data using the frozen vectors, generating, using the machine learning model on the processed data and without requiring renormalization of the entirety of the training dataset, a likelihood score related to cancer occurrence by inputting the processed data into nodes of the machine learning model, wherein the nodes and the frozen vectors are both derived from the training dataset.

4. The method of claim 3, wherein the machine learning model comprises a random forest having decision trees.

5. The method of claim 3, wherein the features have a non-zero co-efficient satisfying a predetermined threshold in multiple bootstrapping processes performed on different subsets of the training dataset.

6. The method of claim 3, further comprising:
   randomly selecting a plurality of subsets of the training dataset for the randomly-selected subsets for deriving the frozen vectors that are used to normalize the target data to generate the processed data.

7. The method of claim 3, wherein:
   obtaining the target data comprises obtaining one or more expression patterns derived from the target sample;
   normalizing the target data comprises normalizing the one or more expression patterns to generate one or more processed expression patterns; and
   generating the likelihood score comprises generating, using the machine learning model on the one or more processed expression patterns, the likelihood score related to the cancer occurrence.

8. The method of claim 3, wherein generating the processed data comprises removing cross-hybridizing probes from the target data.

9. The method of claim 3, wherein generating the likelihood score comprises generating, using the machine learning model on the processed data, a score indicating a probability of a stage of a plurality of stages of the cancer occurrence.

10. The method of claim 3, wherein generating the likelihood score comprises generating, using the machine learning model on the processed data, a score indicating a probability of recurrence of the cancer occurrence.

11. One or more non-transitory machine-readable media storing instructions, that when executed by one or more processing devices, cause operations comprising:
   accessing a machine learning model comprising features that are selected for the machine learning model and derived from a training dataset;
   obtaining target data derived from a target sample;
   generating, using frozen vectors derived from randomly-selected subsets of the training dataset, processed data from the target data; and
   after generating the processed data using the frozen vectors, generating, using the machine learning model on the processed data and without requiring renormalization of the entirety of the training dataset, a likelihood score related to cancer occurrence by inputting the processed data into nodes of the machine learning model.

12. The media of claim 11, wherein the machine learning model comprises a random forest having decision trees.

13. The media of claim 11, wherein the target data is derived via an array on which probes specific to targets are attached.

14. The media of claim 11, wherein each feature of the features of the machine learning model has a non-zero co-efficient greater than a predetermined threshold in multiple bootstrapping processes performed on different subsets of the training dataset.

15. The media of claim 11, the operations further comprising:
   randomly selecting a plurality of subsets of the training dataset for the randomly-selected subsets for deriving the frozen vectors that are used to normalize the target data to generate the processed data.

16. The media of claim 11, wherein:
obtaining the target data comprises obtaining one or more expression patterns derived from the target sample;
normalizing the target data comprises normalizing the one or more expression patterns to generate one or more processed expression patterns; and
generating the likelihood score comprises generating, using the machine learning model on the one or more processed expression patterns, the likelihood score related to the cancer occurrence.

17. The media of claim 11, wherein generating the processed data comprises removing cross-hybridizing probes from the target data.

18. The media of claim 11, wherein generating the likelihood score comprises generating, using the machine learning model on the processed data, a score indicating a probability a stage of a plurality of stages of the cancer occurrence.

19. The media of claim 11, wherein generating the likelihood score comprises generating, using the machine learning model on the processed data, a score indicating a probability of recurrence of the cancer occurrence.

* * * * *